US008721686B2

(12) United States Patent
Gordon et al.

(10) Patent No.: US 8,721,686 B2
(45) Date of Patent: May 13, 2014

(54) SPINOUS PROCESS FUSION IMPLANTS AND INSERTION, COMPRESSION, AND LOCKING INSTRUMENTATION

(75) Inventors: Charles Gordon, Tyler, TX (US); Marc Yap, The Colony, TX (US); Daniel J. Triplett, Providence, UT (US); Darin Ewer, Providence, UT (US); Nathan Nelson, Hyde Park, UT (US); Andrew Fauth, River Heights, UT (US); M. Mary Sinnott, Logan, UT (US)

(73) Assignee: OsteoMed LLC, Addison, TX (US)

( * ) Notice: Subject to any disclaimer, the term of this patent is extended or adjusted under 35 U.S.C. 154(b) by 94 days.

(21) Appl. No.: 13/188,325

(22) Filed: Jul. 21, 2011

(65) Prior Publication Data
US 2011/0319936 A1 Dec. 29, 2011

Related U.S. Application Data

(63) Continuation-in-part of application No. 12/853,689, filed on Aug. 10, 2010, which is a continuation-in-part of application No. 12/820,575, filed on Jun. 22, 2010, now Pat. No. 8,377,097.

(60) Provisional application No. 61/219,687, filed on Jun. 23, 2009, provisional application No. 61/232,692, filed on Aug. 10, 2009, provisional application No. 61/366,755, filed on Jul. 22, 2010.

(51) Int. Cl.
*A61B 17/70* (2006.01)
(52) U.S. Cl.
USPC ........................................ 606/248; 606/86 A
(58) Field of Classification Search
USPC ......... 606/246–279, 99, 102, 104, 105, 86 A, 606/86 B, 282, 71; 623/17.11, 17.16
See application file for complete search history.

(56) References Cited

U.S. PATENT DOCUMENTS

| 4,066,082 | A | * | 1/1978 | Arcan et al. ............... 606/102 |
| 5,836,948 | A | | 11/1998 | Zucherman |
| 6,238,397 | B1 | | 5/2001 | Zucherman |
| 6,312,431 | B1 | | 11/2001 | Asfora |
| 6,330,883 | B1 | | 12/2001 | Berger |
| 6,379,355 | B1 | | 4/2002 | Zucherman |
| 6,695,842 | B2 | | 2/2004 | Zucherman |
| 6,712,819 | B2 | | 3/2004 | Zucherman |

(Continued)

FOREIGN PATENT DOCUMENTS

WO    WO2003007829    1/2003

*Primary Examiner* — Mary Hoffman
*Assistant Examiner* — Michelle C Eckman
(74) *Attorney, Agent, or Firm* — Fulbright & Jaworski LLP

(57) ABSTRACT

A bone plate assembly including at least one bone plate, polyaxially adjustable fixation elements and a polyaxially adjustable locking mechanism. A first plate includes at least one polyaxial element for lockable connection with a fixation pad, and a connection feature which allows the plate to translate and polyaxially rotate relative to the locking mechanism. A second plate includes at least one polyaxial element for connection with a fixation pad and a connection feature for non-rotatable connection with the locking mechanism. The locking mechanism allows translation and polyaxial adjustment of the first plate relative to the second plate and locks the first and second plates via a taper lock. The fixation pad includes a deflectable spacer configured to prevent premature locking of the pad. Methods for implantation of the bone plate assembly between bone structures are disclosed. Instrumentation for implantation, compression and locking of the bone plate assembly is disclosed.

18 Claims, 56 Drawing Sheets

(56) References Cited

U.S. PATENT DOCUMENTS

| | | |
|---|---|---|
| 6,796,983 B1 | 9/2004 | Zucherman |
| 7,048,736 B2 | 5/2006 | Robinson |
| 7,588,592 B2 | 9/2009 | Winslow |
| 7,727,233 B2 | 6/2010 | Blackwell |
| 8,128,659 B2 | 3/2012 | Ginsberg |
| 2004/0193272 A1* | 9/2004 | Zubok et al. ............... 623/17.11 |
| 2006/0247623 A1 | 11/2006 | Anderson |
| 2006/0247634 A1 | 11/2006 | Warner |
| 2007/0270812 A1 | 11/2007 | Peckham |
| 2007/0270840 A1 | 11/2007 | Chin |
| 2008/0021471 A1 | 1/2008 | Winslow |
| 2008/0140125 A1* | 6/2008 | Mitchell et al. ............... 606/279 |
| 2008/0183211 A1 | 7/2008 | Lamborne |
| 2008/0183218 A1 | 7/2008 | Mueller |
| 2009/0062918 A1* | 3/2009 | Wang et al. ............... 623/17.16 |
| 2009/0216273 A1* | 8/2009 | Cox ............... 606/246 |
| 2009/0264927 A1* | 10/2009 | Ginsberg et al. ............... 606/246 |
| 2010/0087860 A1* | 4/2010 | Chin et al. ............... 606/249 |
| 2010/0241167 A1 | 9/2010 | Taber et al. |
| 2011/0224740 A1* | 9/2011 | Smisson et al. ............... 606/86 A |
| 2012/0310292 A1* | 12/2012 | Smisson et al. ............... 606/86 A |

* cited by examiner

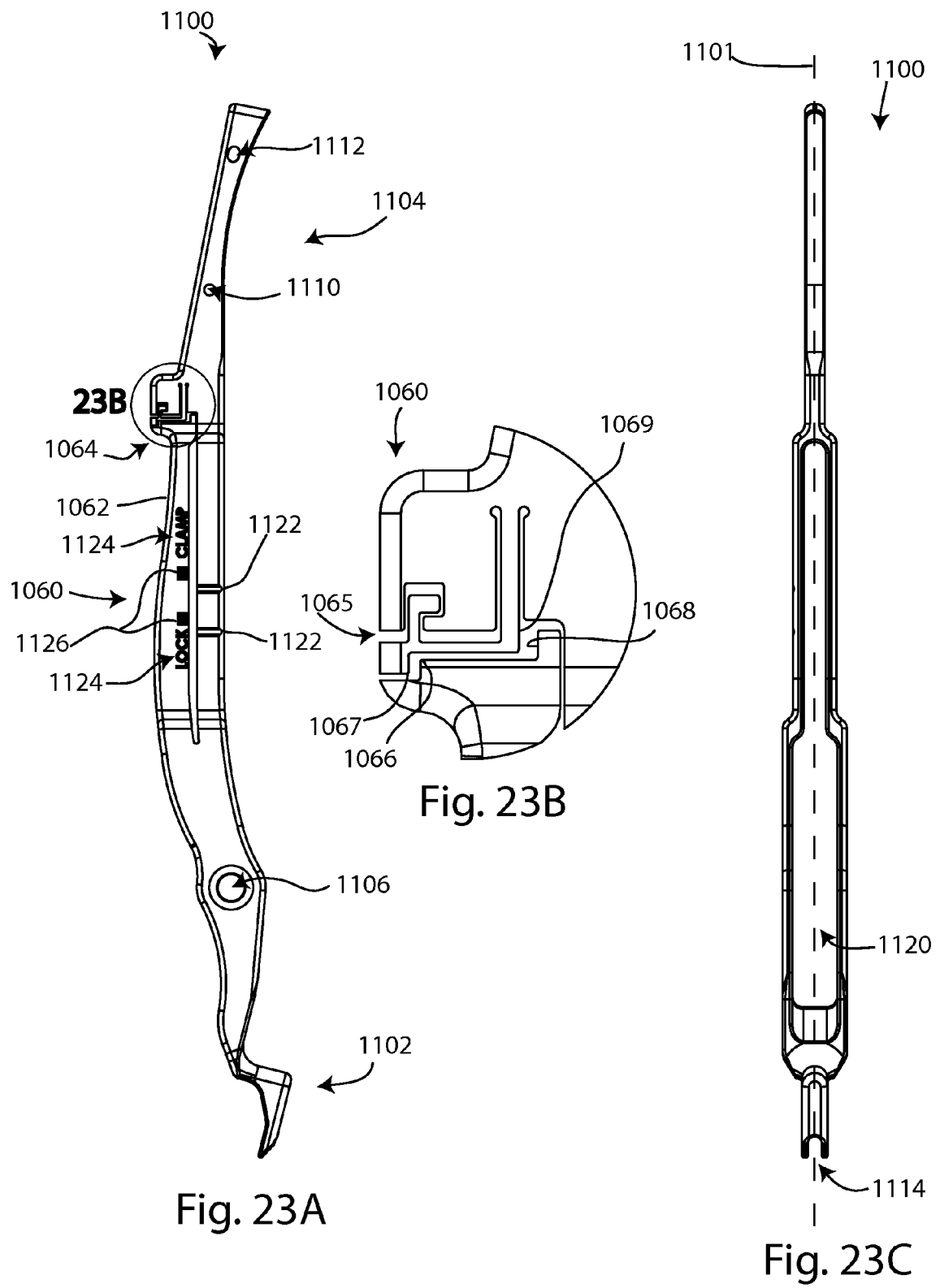

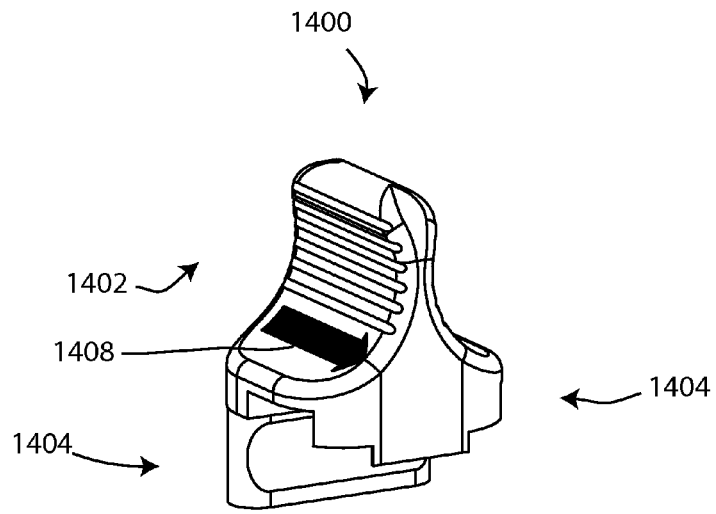
Fig. 26A
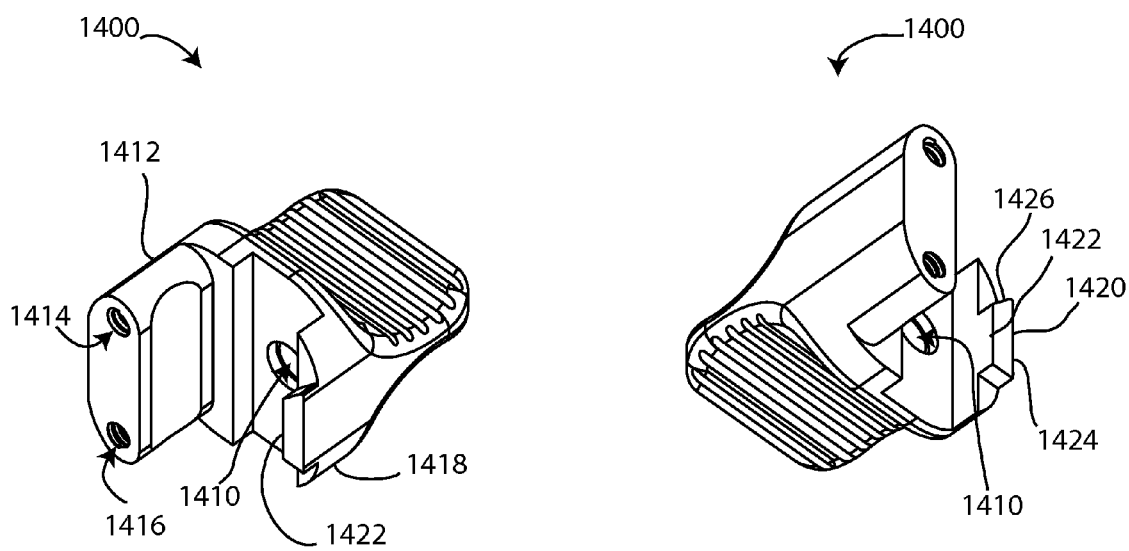
Fig. 26B
Fig. 26C

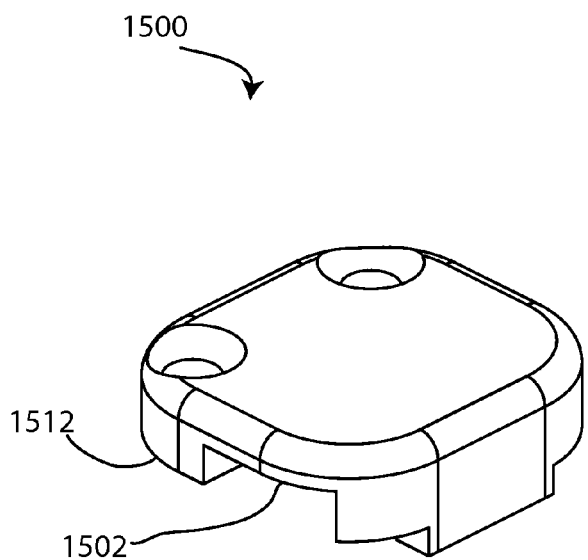
Fig. 27A
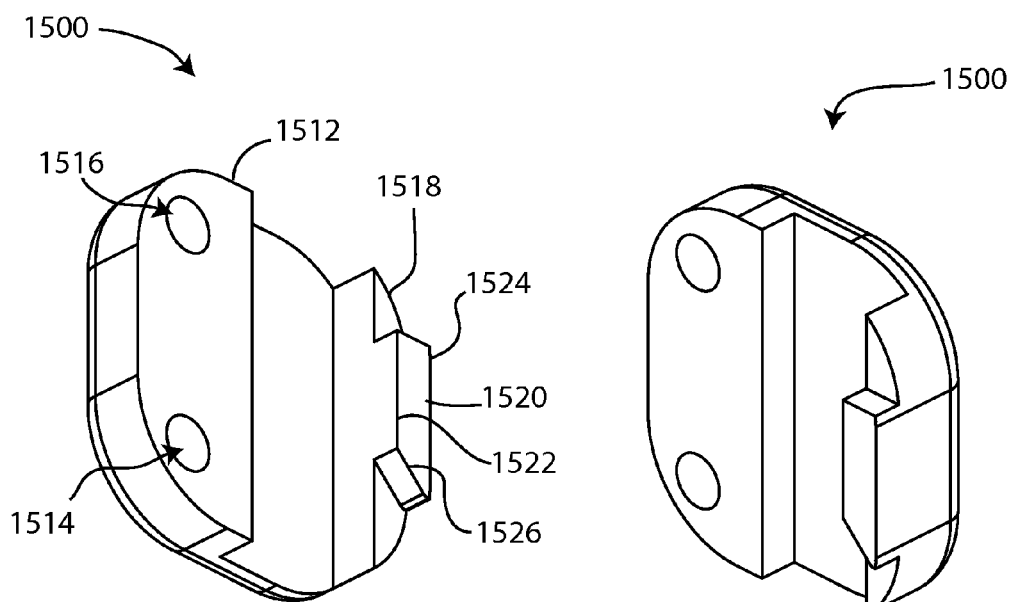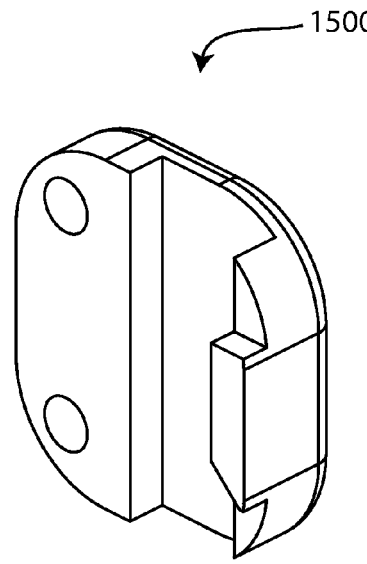
Fig. 27B
Fig. 27C

SPINOUS PROCESS FUSION IMPLANTS AND INSERTION, COMPRESSION, AND LOCKING INSTRUMENTATION

CROSS-REFERENCE TO RELATED APPLICATIONS

This application is a continuation-in-part of:

pending prior U.S. patent application Ser. No. 12/853,689 filed Aug. 10, 2010 and entitled SPINOUS PROCESS FUSION IMPLANTS.

U.S. patent application Ser. No. 12/853,689 is a continuation-in-part of:

pending prior U.S. patent application Ser. No. 12/820,575 filed Jun. 22, 2010 and entitled BONE TISSUE CLAMP.

U.S. patent application Ser. No. 12/820,575 claims the benefit of:

expired U.S. Provisional Patent Application Ser. No. 61/219,687, filed Jun. 23, 2009 and entitled BONE TISSUE CLAMP.

U.S. patent application Ser. No. 12/853,689 also claims the benefit of:

expired U.S. Provisional Patent Application No. 61/232,692, filed Aug. 10, 2009, entitled SPINOUS PROCESS FUSION IMPLANTS; and pending U.S. Provisional Patent Application No. 61/366,755, filed Jul. 22, 2010, entitled INSERTION, COMPRESSION AND LOCKING INSTRUMENTATION.

The above-referenced documents are hereby incorporated by reference in their & entirety.

FIELD OF THE INVENTION

The present invention relates generally to bone plates, and more specifically to bone fusion procedures in which two or more bone portions are stabilized in order to promote the development of a bony fusion mass.

BACKGROUND OF THE INVENTION

A normal, healthy bone typically has complex surface geometry which is dictated by the function of the bone in the body. The surface of a bone rarely forms a regular geometric shape, such as a plane, cylinder, cone, or sphere. This phenomenon is exacerbated in diseased, damaged, or deformed bones. Even when a portion of a bone is removed, or resected, the cut surface may be irregular. When a bone is fractured, the potential for irregular fragments is high. Similar surfaces on adjacent bones may be a different shape and size, and are often not precisely aligned. For all these reasons, it can be challenging to fit a bone plate to bone surfaces securely enough to stabilize a developing fusion mass. This is especially true if the bone plate is designed as a regular geometric shape, such as a rectangular solid. The present invention provides an apparatus that automatically adjusts itself to fit congruently on irregular bone surfaces.

Bone plates are often secured to bone with screws, pegs, or other fixation elements. A common characteristic of these fixation elements is that they invasively penetrate the surface of the bone in order to achieve fixation. When removed, or revised, they leave behind defects which may limit the surgical options for subsequent procedures. These types of fixation elements usually rely at least in part on cancellous bone for their fixation strength. However, cancellous bone is notoriously variable in quality. Cortical bone is a superior load bearing material compared to cancellous bone. However, in many locations on the skeleton, cortical bone is distributed in a relatively thin layer. Furthermore, precisely because cortical bone is a strong load bearing material, it can be difficult to seat a cortical fixation element unless the fixation element is aligned with the cortical surface. The present invention provides an apparatus that achieves fixation in cortical bone without collateral damage to cortical or cancellous bone.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear.

FIG. 23A is a front view of the lock leg of FIG. 21; FIG. 23B is an enlarged detail view of a portion of the lock leg, as indicated by the circle 23B in FIG. 23A; and FIG. 23C is a side view of the lock leg of FIG. 23A;

FIG. 26A is a perspective view of the selector body of FIG. 21; FIG. 26B is another perspective view of the selector body of FIG. 26A from a different angle; and FIG. 26C is yet another perspective view of the selector body of FIG. 26A from another different angle;

FIG. 27A is a perspective view of the selector back plate of FIG. 21; FIG. 27B is another perspective view of the selector back plate of FIG. 27A from a different angle; and FIG. 27C is yet another perspective view of the selector back plate of FIG. 27A from another different angle;

DETAILED DESCRIPTION

Figure 1:
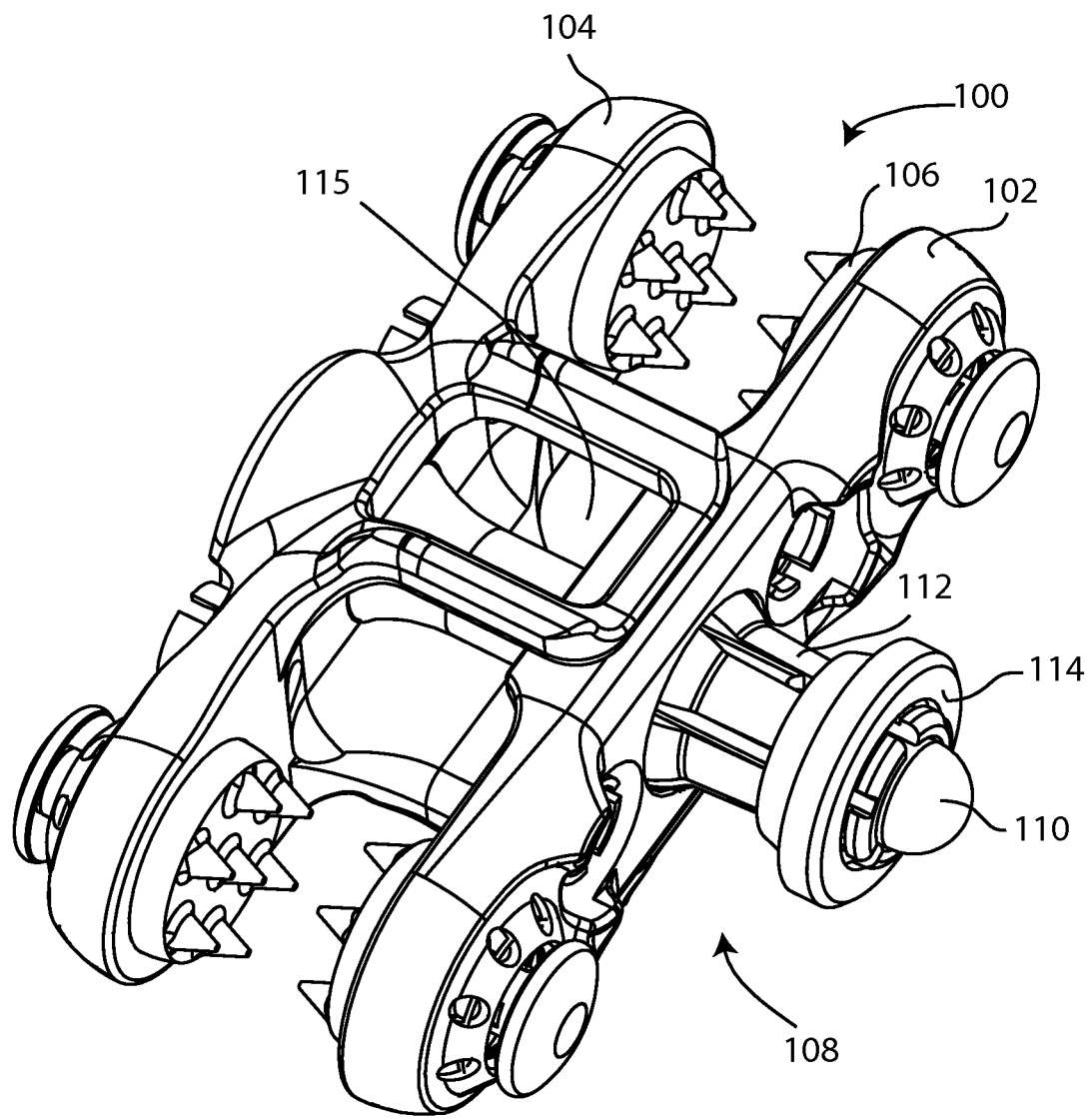
FIG. 1 is an isometric view of a spinous process fusion implant including a first plate, a second plate, a plurality of fixation pads and a locking mechanism, the implant in an unlocked configuration.

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention.

In the following Detailed Description, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

Standard medical planes of reference and descriptive terminology are employed in this specification. While these terms are commonly used to refer to the human body, certain terms are broadly applicable to physical objects in general. A sagittal plane divides a body into right and left portions. A mid-sagittal plane divides a body into equal right and left halves. A coronal plane divides a body into anterior and posterior portions. A transverse plane divides a body into superior and inferior portions. Anterior means toward the front of a body. Posterior means toward the back of a body. Superior or cephalad means toward the head. Inferior or caudal means toward the feet. Medial means toward the midline of a body. Lateral means away from the midline of a body. Axial means toward a central axis of a body. Abaxial means away from a central axis of a body. Generally parallel means an angle of 0 degrees, plus or minus 45 degrees. Generally perpendicular means an angle of 90 degrees, plus or minus 45 degrees. Oblique means an angle between 0 degrees and 90 degrees, i.e., neither perpendicular nor parallel.

In this application, polyaxial rotation is rotation that can occur about at least two axes that are not parallel to each other. Triaxial rotation is rotation about three perpendicular axes. Triaxial rotation is equivalent to rotation about a point, because free rotation about any axis of a 3D coordinate system is the same as rotation that is not limited to any axis in the system. A polyaxial connection permits a component to be rotated with respect to another component around more than one axis. Polyaxial may be synonymous with multiaxial, a multiaxial joint being a joint in which movement occurs in a number of axes. Examples of polyaxial connections include a ball-and-socket joint such as a hip, and ellipsoid joint such as the humerus/glenoid or the wrist, a universal joint, a two axis gimbal set, and a Canfield joint, among other polyaxial connections known in the art. A swivel is a connection that allows the connected object, such as a gun or chair, to rotate horizontally and/or vertically.

A pad is a component of a clamping device designed to directly contact a surface of a workpiece to transfer pressure from the clamp to the workpiece. A swivel pad is a component of a clamping device designed to rotate to congruently contact a surface of a workpiece when pressure is applied with the clamp.

A great circle of a sphere is a circle that runs along the surface of that sphere so as to cut it into two equal halves. Great circle, major diameter, and equator may all be synonymous.

An obverse side is the more conspicuous or significant of two sides of an object. For example, in numismatics, the obverse of a coin is the front, main, top, or "heads" side, usually bearing a portrait. A reverse side is the corresponding less conspicuous or significant side. For example, the reverse of a coin is the back, bottom, or "tails" side. In this application, a side may be considered significant because it faces toward a surgical attachment site, such as a bony structure.

Undercut means to cut away material from the underside of an object or feature so as to leave an overhanging portion in relief.

Elastic deformation means a deformation of a body in which the applied stress is small enough so that the object retains its original dimensions once the stress is released.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

According to a first aspect, a system includes an implant and a primary instrument. The implant includes a first portion, a second portion opposite the first portion, and a locking mechanism coupling the first portion to the second portion. The system has an insertion configuration, a clamped configuration, and a first locked configuration. In the insertion configuration, the primary instrument holds the first portion apart from the second portion. The primary instrument urges the first portion toward the second portion to change the system from the insertion configuration to the clamped configuration. The primary instrument permits the first portion to polyaxially rotate relative to the second portion as the first portion is urged toward the second portion. In the clamped configuration, the primary instrument holds the first portion fixed relative to the second portion. The primary instrument urges at least a first component of the locking mechanism from an unlocked position to a first locked position to change the system from the clamped configuration to the first locked configuration. The primary instrument a maintains the first portion fixed relative to the second portion as the first component is urged from the unlocked position to the first locked position. In the first locked configuration, the first component maintains the first portion fixed relative to the second portion.

In an embodiment, the primary instrument includes first and second opposing jaws, wherein the first jaw is pivotable relative to the second jaw about first and second axes, wherein the second axis is perpendicular to the first axis, wherein the first jaw holds the first portion, wherein the first portion is pivotable relative to the first jaw about a third axis, wherein the third axis is perpendicular to the second axis, wherein the second jaw holds the second portion, wherein the second portion is pivotable relative to the second jaw about a fourth axis, wherein the fourth axis is parallel to the first axis.

In another embodiment, the primary instrument includes a force indicator which indicates when a predetermined locking force has been applied by the primary instrument to urge the first component from the unlocked position to the first locked position.

In yet another embodiment, the primary instrument avoids contact with the locking mechanism in the insertion configuration and the clamped configuration, yet contacts at least the first component in the first locked configuration.

In yet another embodiment, the primary instrument includes a selector. In the insertion and clamped configurations, the selector is in a first position. In the first locked configuration, the selector is in a second position. When the selector is in the first position, the system is prevented from changing to the first locked configuration. When the selector is in the second position, the system is permitted to change to the first locked configuration.

In yet another embodiment, the system includes a secondary instrument. The system has a second locked configuration. The secondary instrument urges at least a second component of the locking mechanism from an unlocked position to a second locked position to change the system from the first locked configuration to the second locked configuration. The secondary instrument avoids contact with the first and second portions as the second component is urged from the unlocked position to the second locked position. In the second locked configuration, the first and second components of the locking mechanism maintain the first portion fixed relative to the second portion.

In yet another embodiment, the secondary instrument includes a force indicator, which indicates when a predetermined locking force has been applied by the secondary instrument to urge the second component from the unlocked position to the locked position.

According to a second aspect, a system includes an implant and a primary instrument releasably securable to the implant. The implant includes first and second plates coupled together by a locking mechanism so that the second plate faces the first plate. The primary instrument includes rigid, lock, and pivot jaws hinged together at a main pivot element so that each jaw is independently rotatable relative to the other jaws about a center longitudinal axis of the pivot element, and the rigid jaw faces the lock and pivot jaws. The lock jaw is releasably fixed to the pivot jaw. The pivot jaw is releasably connected to the rigid jaw. The connection permits one way motion of the pivot jaw toward the rigid jaw. The pivot jaw is rotatable relative to the rigid and lock jaws about a second axis. The second axis forms a non-zero angle with the center longitudinal axis. The primary instrument picks up, inserts, compresses, and locks the implant while remaining continuously secured to the implant.

In an embodiment, the first plate is releasably securable to the pivot jaw and the second plate is releasably securable to the rigid jaw.

In another embodiment, the first plate and second plate each include cup shaped pockets and the pivot jaw and the rigid jaw each include spherical tips. The cup shaped pockets releasably receive the spherical tips. The cup shaped pockets are pivotable on the spherical tips.

In yet another embodiment, the system includes a caddy, which supports the implant with the first plate separated from the second plate. The primary instrument is releasably securable to the implant while the implant is supported by the caddy. The primary instrument picks the implant up out of the caddy after the primary instrument is releasably secured to the implant.

In yet another embodiment, the primary instrument holds the first plate separated from the second plate while the implant is inserted into an implantation site.

In yet another embodiment, the lock jaw applies no compressive force to the implant when the lock jaw is releasably fixed to the pivot jaw while the primary instrument compresses the first and second plates together.

In yet another embodiment, the lock jaw applies a compressive force to the implant when the lock jaw is released from the pivot jaw while the primary instrument locks the first and second plates together.

According to a third aspect, an insertion, compression, and locking instrument includes a rigid leg, a lock leg, a pivot leg, and a selector. The rigid leg includes a handle portion and a tip portion opposite the handle portion. The lock leg includes a handle portion and a tip portion opposite the handle portion. The pivot leg includes a rear portion and a tip portion opposite the rear portion. The pivot leg tip portion swivels relative to the pivot leg rear portion. The rigid leg, the lock leg, and the pivot leg are pivotally attached together. The rigid leg tip portion faces the lock leg tip portion and the pivot leg tip portion. When the selector is in a first position, the lock leg and the pivot leg pivot as one relative to the rigid leg. When the selector is in a second position, the lock leg and the pivot leg pivot separately relative to the rigid leg.

In an embodiment, the rigid leg tip portion includes a pair of spherical protrusions and the pivot leg tip portion includes a pair of spherical protrusions. The rigid leg protrusions face the pivot leg protrusions.

In another embodiment, the rigid leg includes a central slot. At least a portion of the pivot leg is within the rigid leg slot. The pivot leg includes a central slot. At least a portion of the rigid leg is within the pivot leg slot.

In yet another embodiment, the instrument includes a force indicator, which indicates when a predetermined force has been applied between the rigid leg tip portion and the lock leg tip portion.

In yet another embodiment, the pivot leg is releasably connectable to the rigid leg. When the pivot leg is connected to the rigid leg, the pivot leg tip portion can move toward the rigid leg tip portion and the pivot leg tip portion is prevented from moving away from the rigid leg tip portion.

In yet another embodiment, the instrument includes a first configuration, in which the selector is in the first position, the rigid leg tip portion is at a first distance from the lock leg tip portion, and the lock leg tip portion is at an initial distance from the pivot leg tip portion; a second configuration, in which the selector is in the first position, the rigid leg tip portion is at a second distance from the lock leg tip portion, and the lock leg tip portion is at the initial distance from the pivot leg tip portion, and a third configuration, in which the selector is in the second position, the rigid leg tip portion is at a third distance from the lock leg tip portion, and the lock leg tip portion is at a final distance from the pivot leg tip portion. The second distance is less than the first distance, the third distance is less than the second distance, and the final distance is greater than the initial distance.

Referring to FIG. 1, an isometric view shows a spinal fusion implant according to one embodiment of the invention, in an unlocked configuration. Spinal implant 100 includes two plates 102, 104, a plurality of pads 106, and a locking mechanism 108. Plate 102 may be a first plate or a flat plate, and plate 104 may be a second plate, or an extension plate. Locking mechanism 108 may rigidly lock the positions of plates 102, 104 relative to one another. Locking mechanism 108 includes post 110, collet 112, and ring 114. At least one of the two plates may polyaxially rotate relative to the other before the locking mechanism is actuated to lock the plates in a fixed relationship. Additionally, each pad is lockable to a plate, and may polyaxially rotate relative to the plate before being locked to the plate in a fixed relationship. A pad may be also termed a fixation pad, foot, or grip. The spinal fusion implant may be termed a bone plate assembly. A bone plate assembly may also include a bone plate in combination with any of the fixation or locking features disclosed herein.

Figure 2:
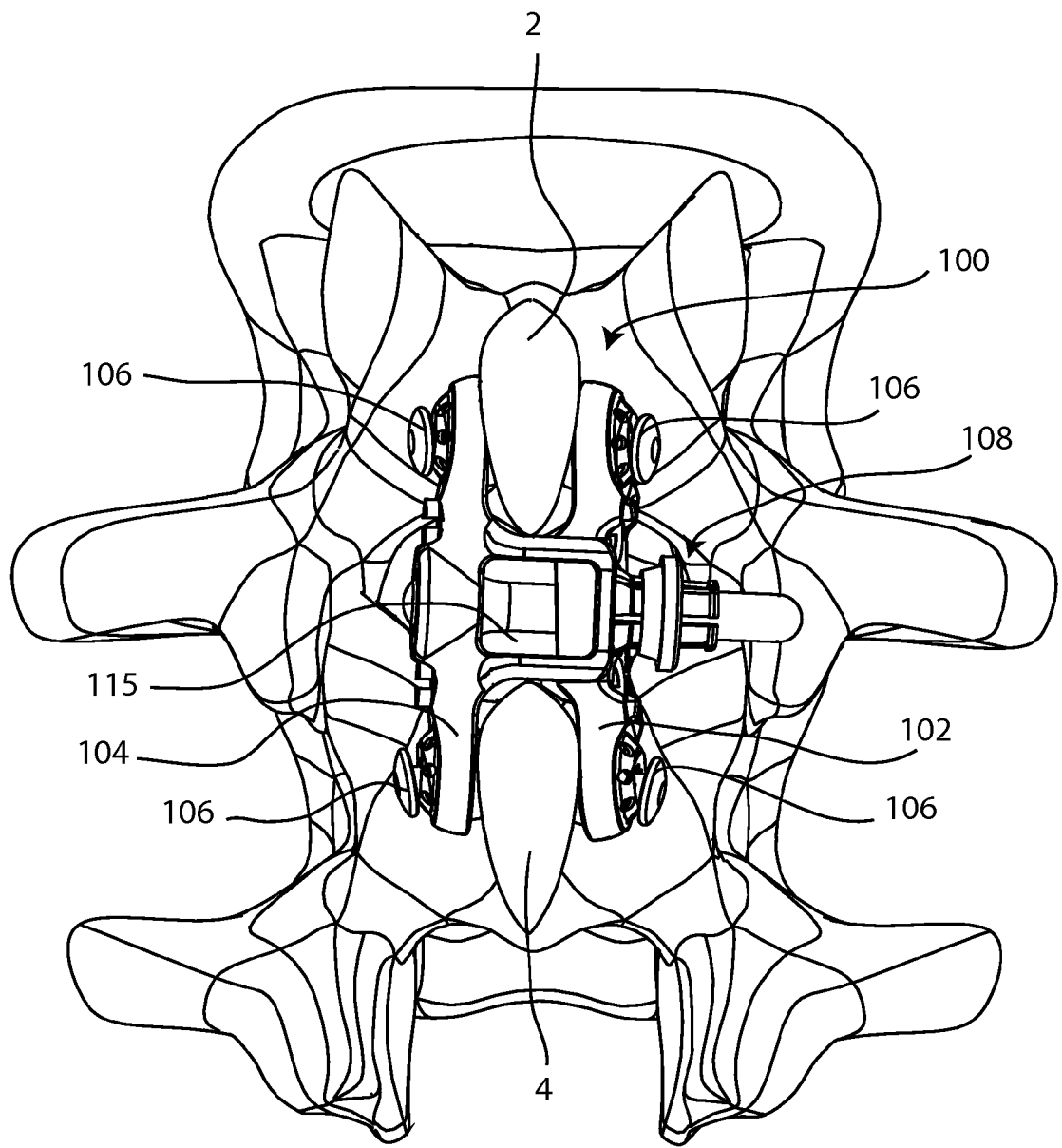
FIG. 2 is a posterior view of the spinous process fusion implant of FIG. 1 implanted between two spinous processes, the implant in a locked configuration, the first plate and the fixation pads polyaxially adjusted to match the spinal anatomy.

As shown in FIG. 2, spinal implant 100 may be implanted in a portion of a spine to promote fusion between two spinous processes 2, 4. Each plate 102, 104 may be positioned to extend cephalad-caudally from a superior, or first spinous process to an inferior, or second spinous process, along a lateral side of the two spinous processes. Each pad 106 may be positioned to extend through an aperture in one of the plates and bear against a lateral side of one of the spinous process. Selective forces may be applied to compress the pads toward the spinous processes, and lock the pads to the plates. The locking mechanism 108 extends transversely between the two spinous processes and couples the plates together, and when a selected force is applied, locks the plates together. An opening in at least one plate provides a window for introduction of bone graft material into a chamber 115 formed between the plates and the spinous processes to further promote fusion between the spinous processes. Although one implant is shown coupled to two spinous processes, it is appreciated that other embodiments may a be coupled to multiple processes, providing fusion across multiple spinal segments. In an alternative embodiment, one or more of the plates may be sized and shaped to extend along at least three spinous processes, and accommodate at least three pads and two locking mechanisms. In another embodiment, multiple spinal implants 100 may be coupled to a series of spinous processes; at least one of the implants 100 may be angled to allow room for more than one implant to be coupled to a single spinous process. It is also appreciated that spinal implant 100 or an alternate embodiment may be coupled to adjacent transverse processes, inferior or superior facets, vertebral bodies, or two other bony structures such as ribs, within the scope of the invention.

Figure 3:
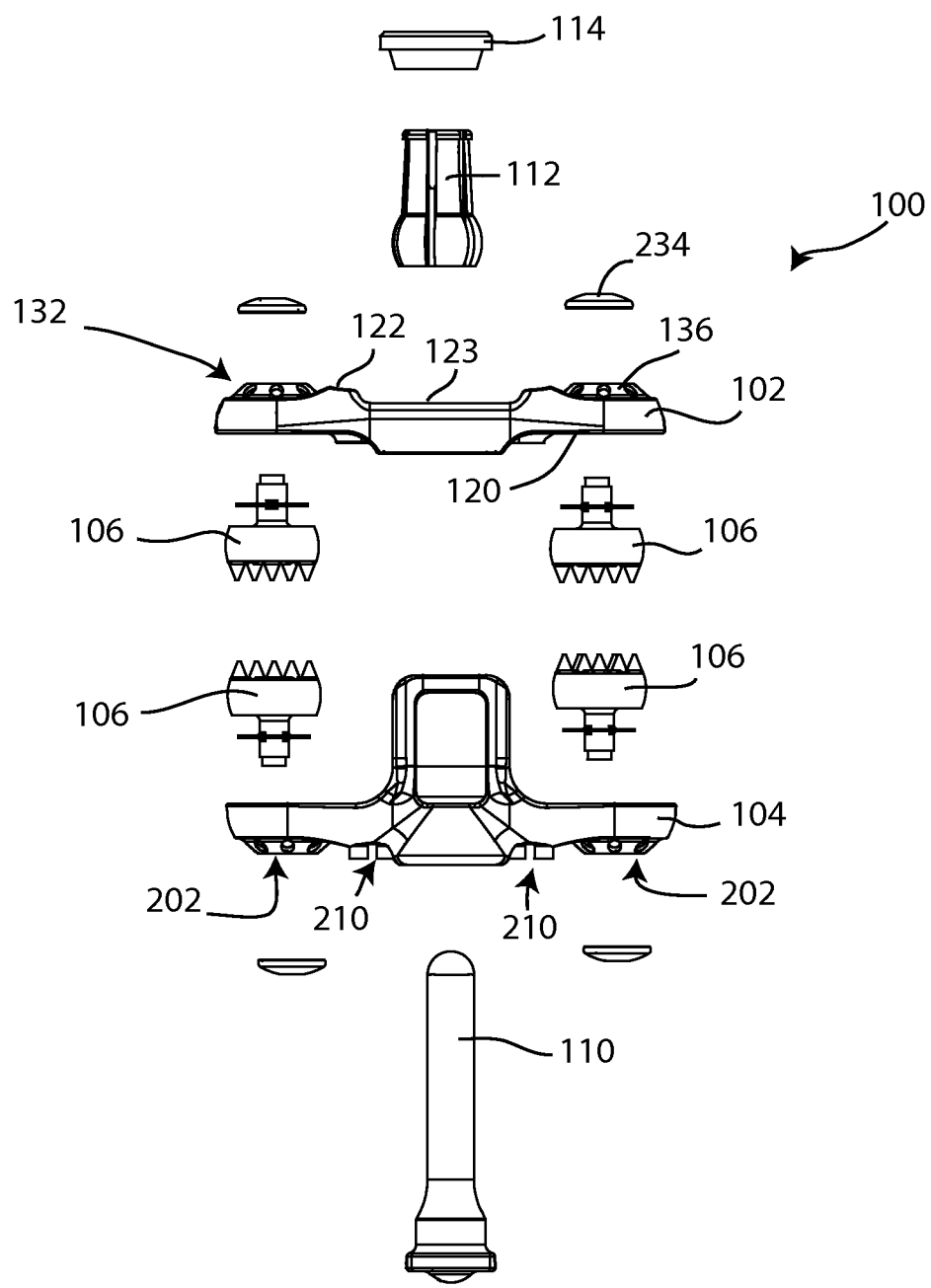
FIG. 3 is an exploded view of the spinous process fusion implant of FIG. 1.

FIG. 3 provides an exploded view of spinal implant 100 to show the relative arrangement of the component parts. Although four fixation pads 106 are depicted in the embodiment shown, it is appreciated that in other embodiments fewer or more fixation pads may be included. Additionally, other embodiments may include other types of fixation, including but not limited to bone screws, pedicle screws, hooks, and clamps. Types of fixation may be mixed within a single embodiment.

Figure 4A:
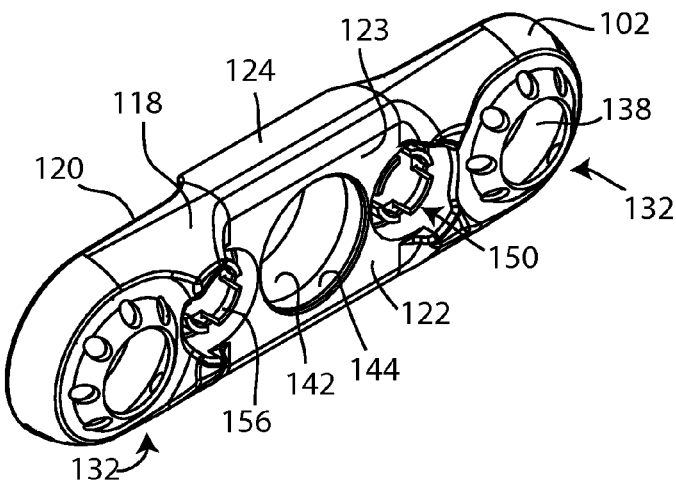
FIG. 4A is an isometric view of the first plate of the spinous process fusion implant of FIG. 1.
Figure 4B:
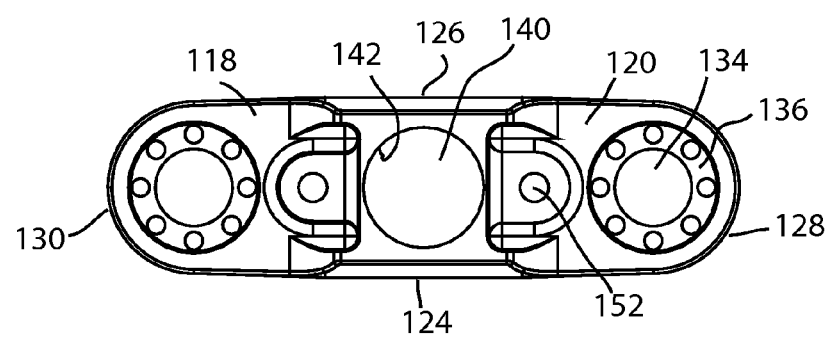
FIG. 4B is a view of an obverse side of the plate of FIG. 4A.
Figure 4C:
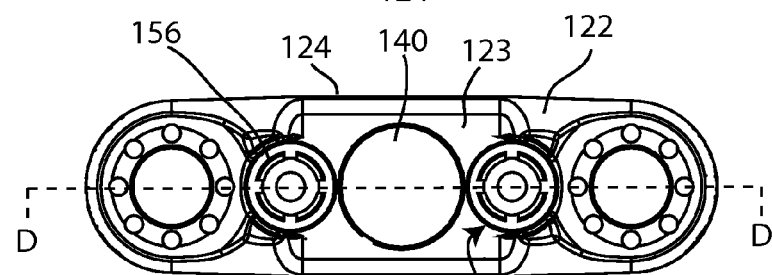
FIG. 4C is a view of a reverse side of the plate of FIG. 4A.
Figure 4D:
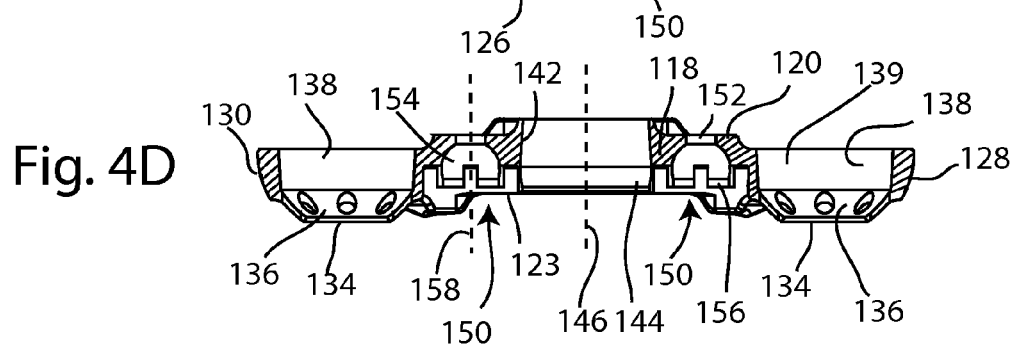
FIG. 4D is a cross-sectional view of the plate of FIG. 4C taken along section line D-D.

FIG. 4A is an isometric view of plate 102, while FIG. 4B is an obverse side view of plate 102; FIG. 4C is a reverse side view of the plate 102; and FIG. 4D is a cross-sectional view taken along section line D-D shown in FIG. 4C. Plate 102, which may be a supporting structure, includes a generally elongated plate body 118 having a first, or obverse side 120, and a second, or reverse side 122, opposite the obverse side. When implanted according to one embodiment of the invention as shown in FIG. 2, the obverse side 120 is a bone-facing side. A portion of the reverse side 122 is occupied by a recess 123. The recess 123 may advantageously afford more room for the collet 112 and ring 114 when the implant 100 is implanted in a portion of a spine, than if the reverse side were not recessed. Plate 102 is bounded by a first plate edge 124, a second plate edge 126, a first plate end 128 and a second plate end 130. It is appreciated that in the embodiment shown, plate 102 is bilaterally symmetrical; however in other embodiments the positioning of features of the plate may vary to provide a symmetrical or a non-symmetrical plate.

Plate 102 includes at least one polyaxial element which may provide for pivoting or polyaxial connection of a pad 106 to the plate, wherein the pad may be positioned at any of a continuum of positions relative to the plate upon locking attachment to the plate. Each polyaxial element 132, which may also be termed a pivot element, includes an aperture 134 extending through an annular flange 136. In the embodiment shown, flange 136 is domed such that it protrudes convexly on the reverse side 122 of the plate, and is recessed concavely on the obverse side 120 of the plate. Adjacent the flange 136 on the obverse side 120 is an annular tapered, or frustoconical surface 138, the widest diameter of the cone opening toward the obverse side 120 of the plate. The taper of the frustoconical surface 138 may preferably range from 1 to 7 degrees so that the taper is self-locking. More specifically, the taper may range from 2 to 5 degrees. Yet more specifically the taper may be 3 degrees. When a spherical surface of a pad 106 is compressed against the frustoconical surface 138 at a selected level of force, an interference taper mechanical lock is provided between the pad 106 and the plate 102. In other embodiments of the invention, surface 138 could be spherical, or flat. Each frustoconical surface 138 and surrounding plate body may also be termed a conical socket 139.

A second aperture or bore 140 extends through the plate body 118 from the obverse side 120 to the reverse side 122. A portion of the bore 140 is bounded by a frustoconical bore surface 142, the widest diameter of the cone opening toward the reverse side 122. A rim surface 144 surrounds the remainder of the bore adjacent the reverse side of the plate, and may be smaller in diameter than the widest diameter of the frustoconical bore surface. The rim surface may also be smaller in diameter than a portion of the collet 112. Bore 140 is tapered, sized and shaped to retain a portion of the collet 112 when the locking mechanism is actuated to lock the plates 102, 104 together. Bore 140 may be a polyaxial connection feature, and with collet 112 a may form a polyaxial connection wherein plate 102 is polyaxially rotatable relative to the locking mechanism prior to actuating the locking mechanism to lock out further movement between the plate and the locking mechanism. Bore 140 further includes a rotation axis 146 about which plate 102 is polyaxially rotatable prior to lock out, the bore centered about the rotation axis.

At least one instrument connection feature, or element 150, may be formed on plate 102 to provide a site for connection to insertion, compression, and/or locking instrumentation. Connection element 150 may be generally annular and may include an opening 152 which is situated in a spherical socket or cup 154. Cup 154 includes a first end toward the reverse side 122 of the plate, a second end toward the obverse side 120 and a middle portion between the first and second ends. The middle portion may be wider than the first end so that the middle portion undercuts the first end. The middle portion may also be wider than the second end. A plurality of tabs 156 protrude from the first end of the cup 154 on the reverse side 122. The tabs 156 may be curved, and each may project slightly toward a center axis 158 of the cup. When a corresponding spherical connection feature on an instrument is advanced into the cup 154, the tabs 156 may elastically deform to grip the instrument spherical connection feature. Cup 154 and the corresponding connection feature of the instrument may have shapes other than spherical, so long as the connection feature fits in the cup 154 and provides a knob end corresponding to the undercut middle portion of the cup 154.

Figure 5A:
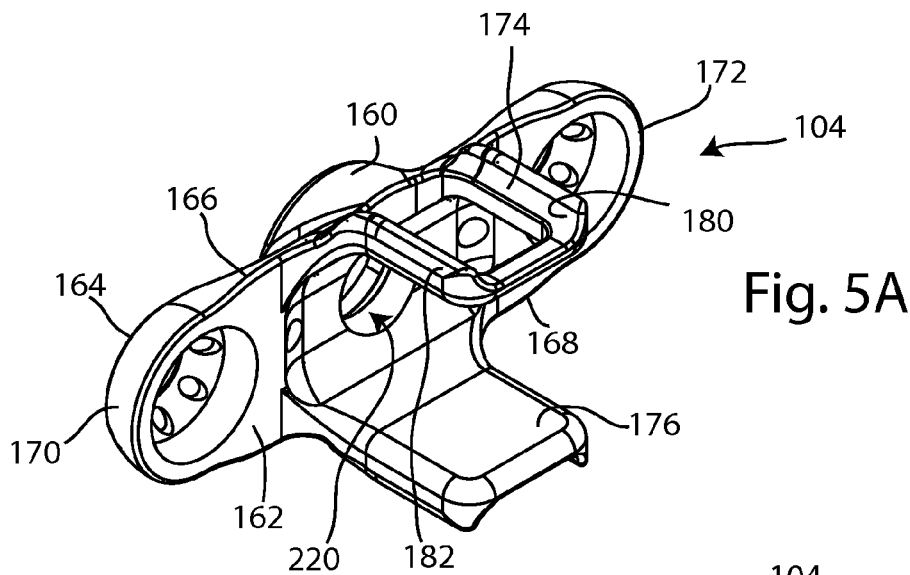
FIG. 5A is an isometric view of the second plate of the spinous process fusion implant of FIG. 1.
Figure 5B:
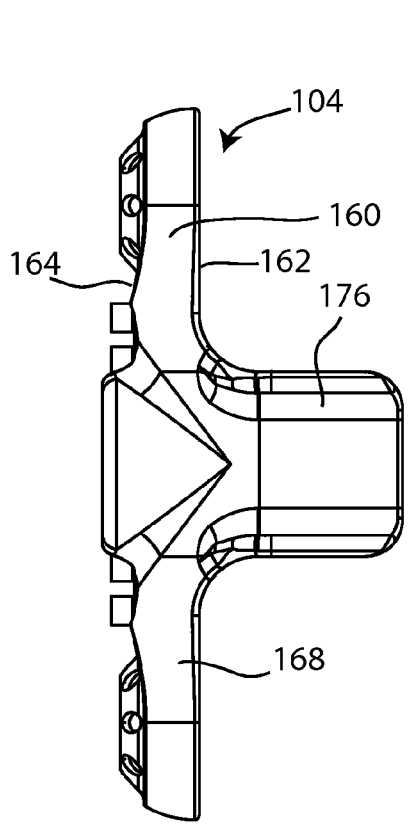
FIG. 5B is a side view of the second plate of FIG. 5A.
Figure 5C:
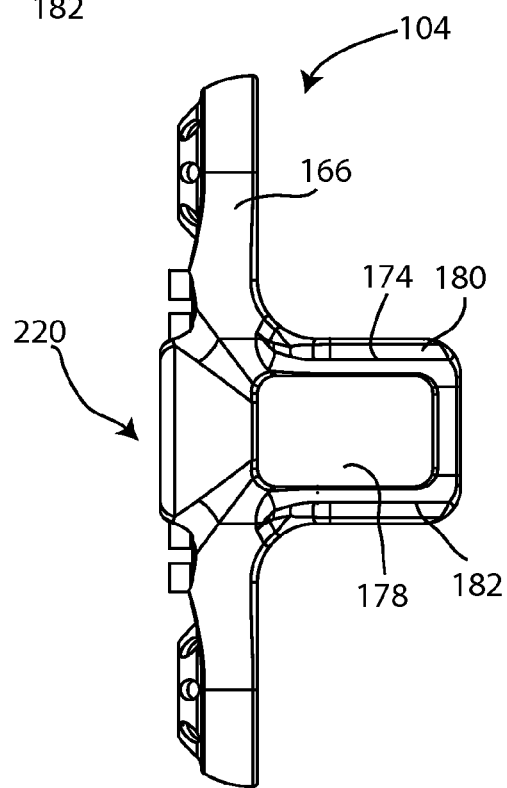
FIG. 5C is an opposite side view of the second plate of FIG. 5B.
Figure 6A:
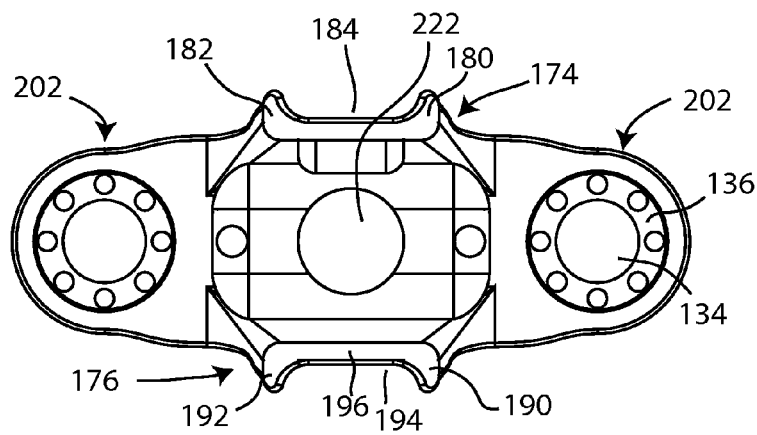
FIG. 6A is a view of an obverse side of the second plate of the spinous process fusion implant of FIG. 1.
Figure 6B:
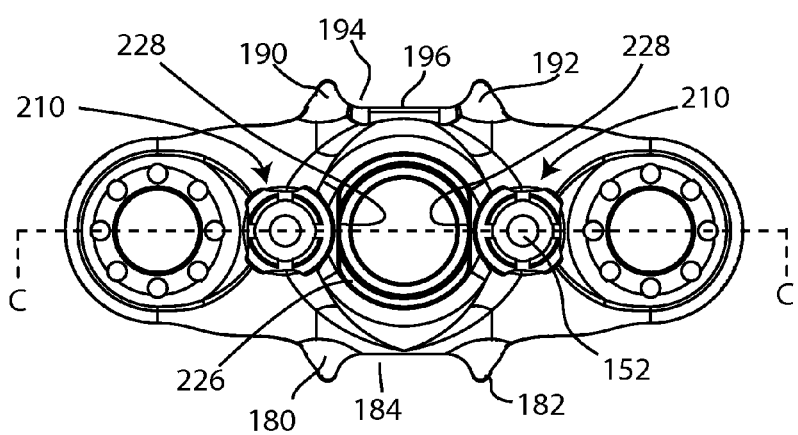
FIG. 6B is a view of a reverse side of the plate of FIG. 6A.
Figure 6C:
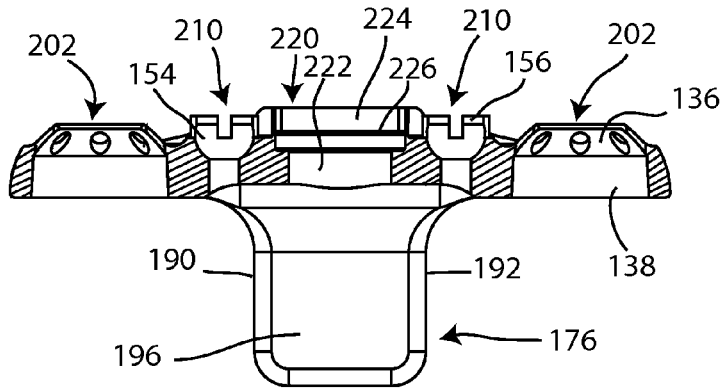
FIG. 6C is a cross-sectional view of the plate of FIG. 6B taken along section line C-C.
Figure 7A:
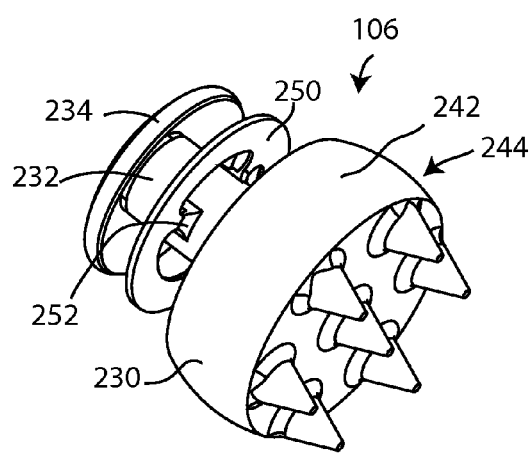
FIG. 7A is an isometric view of a fixation pad of the spinous process fusion implant of FIG. 1.
Figure 7B:
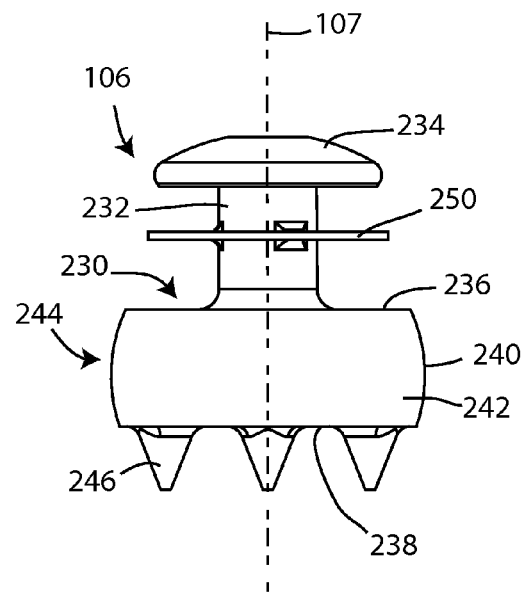
FIG. 7B is a side view of the fixation pad of FIG. 7A.
Figure 7C:
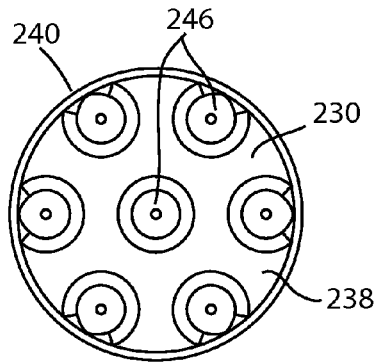
FIG. 7C is a view of a bone-facing end of the fixation pad of FIG. 7A.
Figure 7D:
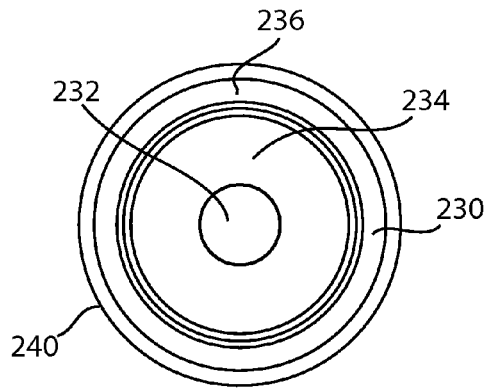
FIG. 7D is a view of an opposite end of the fixation pad of FIG. 7C.

Referring to FIGS. 5A-5C, isometric and side views of the extension plate, or plate 104, are shown. FIG. 6A shows the obverse side of extension plate 104, FIG. 6B shows the reverse side, and FIG. 6C is a cross-sectional view of extension plate 104 taken along line C-C in FIG. 6B.

Extension plate 104, which may be a supporting structure, includes a generally rectangular plate body 160 having a first, or obverse side 162, and a second, or reverse side 164, opposite the obverse side. When implanted according to one embodiment of the invention as shown in FIG. 2, the obverse side 162 is a bone-facing side. Extension plate 104 has a first extension plate edge 166, a second extension plate edge 168, a first extension plate end 170 and a second extension plate end 172. A first wall 174 extends substantially perpendicularly to the plate body 160 from the first extension plate edge 166, and a second wall 176 extends substantially perpendicularly to the plate body 160 from the second extension plate edge 168. First wall 174 includes a window 178. First and second protruding edges 180, 182 project perpendicularly from the first wall 174, forming a first open channel 184 between them.

Similarly, second wall 176 includes first and second protruding edges 190, 192 which project perpendicularly from the second wall, forming a second open channel 194 between them. A wall body 196 spans between the first and second protruding edges. When extension plate 104 is implanted in a portion of a spine as seen in FIG. 2, the protruding edges 190, 192 of the second wall may contact first and second spinous processes, as seen in FIG. 2. The thicker profile of the protruding edges 190, 192 may present more surface area for contact with the spinous processes than would the thinner wall body 196. The thicker protruding edges, providing greater surface area, may be less likely to damage surrounding tissues such as the spinous processes than would a thinner edge presenting less surface area.

Extension plate 104 further includes at least one polyaxial element 202 which may provide for polyaxial connection of a pad 106 to the plate, wherein the pad may be positioned at any of a continuum of positions relative to the plate upon locking attachment to the plate. Each polyaxial element 202, which may be termed a pivot element, may include features identical to those previously set forth for polyaxial element 132 on plate 102, to at least include aperture 134, domed flange 136, and frustoconical surface 138. Similarly, extension plate 104 may further include at least one instrument connection element 210, to provide a site for connection to insertion, compression, and/or locking instrumentation. Each connection element 210 may include features identical to those previously set forth for connection element 150 on plate 102, at least including opening 152, spherical cup 154, and tabs 156.

A pin connection feature 220 which retains a pin or post in a fixed rotational alignment may occupy a central position on extension plate 104. Pin connection feature 220 includes an aperture or bore 222 which extends through the plate from the obverse side to the reverse side, and a counterbore 224 situated at the end of the bore on the reverse side 164 of the plate 104. A protrusion 226 forms a step in the counterbore 224. The bore 222, counterbore 224 and protrusion 226 are generally annular; however one or more flattened portions 228 may be formed on the inner sides of the bore, counterbore, and/or protrusion to prohibit rotation of a pin or post coupled to the plate 104 to extend through the pin connection feature 220.

Referring to FIGS. 7A-D and 8A and 8B, one or more pads 106 may be lockingly coupled to plate 102 and/or extension plate 104. Pad 106 is generally radially symmetrical about a rotation axis 107 and includes a pad body 230, stem 232, and a cap 234. The cap 234 may be formed separately from the pad body and stem, and frictionally or snap fitted onto stem 232 to facilitate assembly of the pad with the plate. Cap 234 may function as a retaining feature, preventing unintentional disassembly of the pad from the plate once assembled together as in FIGS. 8A and 8B. Pad body 230 may be integrally formed with stem 232, and includes a first side 236, a second side opposite the first side comprising a bearing face 238, and a spherical wall 240 extending between the first side and the bearing face. The exterior of the spherical wall 240 is an annular bearing surface 242 which is inherently spherical, as it provides the exterior of the spherical wall. The outer diameter of the first side 236 may be less than the outer diameter of the bearing face 238 as in FIG. 7B; in other embodiments the outer diameters may be equal. The major diameter of the spherical wall 240 is greater than the outer diameters of the first side 236 and the bearing face 238. The spherical wall 240 and its surface 242 form a polyaxial feature 244 for locking with a polyaxial element, including polyaxial elements 132, 202 of plates 102, 104. The polyaxial feature may also be termed a pivot feature as it allows the pad to pivot and/or rotate relative to a pivot element. On the bearing face 238, a plurality of protrusions, or teeth 246 project away from the bearing face. The protrusions and/or bearing face 238 may further include treatments including but not limited to surface roughening, porous coating, knurling, and other treatments to enhance engagement with bony structures. In other embodiments of the invention, the protrusions may include spikes, barbs, pins, prongs, teeth, ridges, tines, pegs, and knurling, among others. In the embodiment shown the teeth 246 are advantageously sized to engage the cortical bone of the spinous process without penetrating cancellous bone, when implanted. In other embodiments of the invention, a pad 106 may not include any teeth or protrusions but instead have a relatively smooth bearing face 238.

Encircling the stem 232 between the pad body 230 and the cap 234 is a thin, generally flat spacer 250. Spacer 250 is joined to stem 232 by at least one stalk 252, and can prevent unintentional locking between the polyaxial feature of the pad 106 and a plate 102, 104. The spacer 250 is deflectable relative to the pad body 230 and stem 232 under a relatively low spacer deflecting force. The spacer 250 may break free of the stem 232 if a sufficient force is applied to it to break the stalks 252.

Figure 8A:
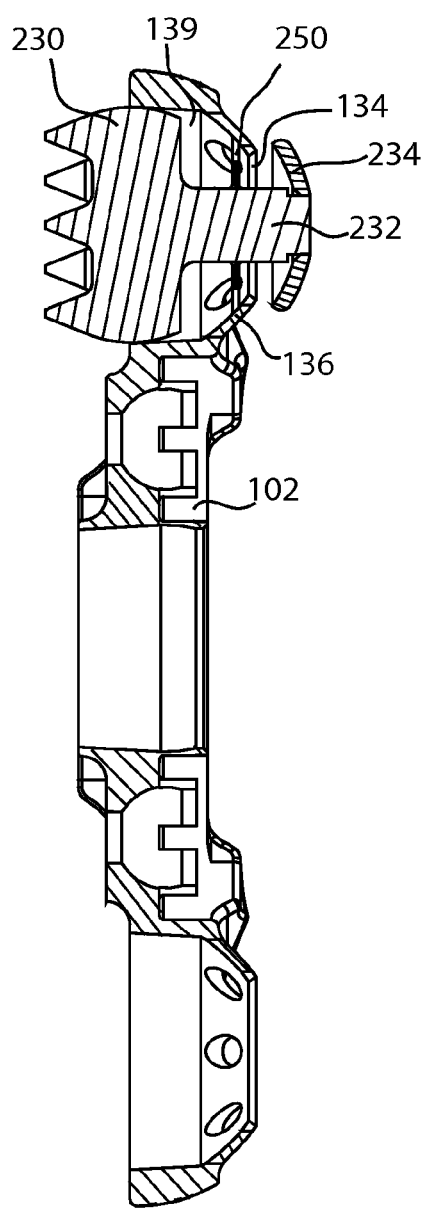
FIG. 8A is a cross-sectional side view of the first plate of the spinous process fusion implant of FIG. 1 with a fixation pad in an unlocked configuration.
Figure 8B:
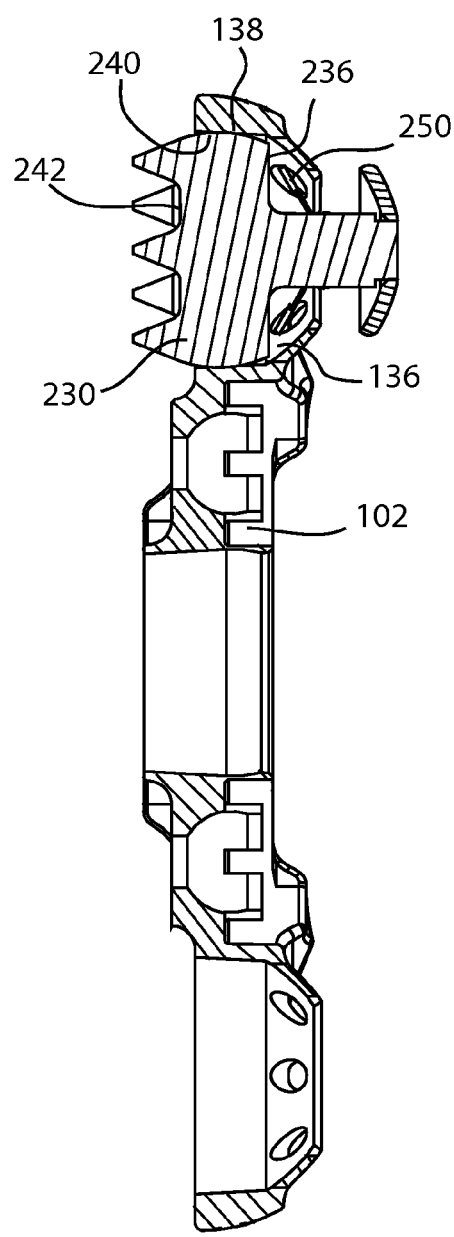
FIG. 8B is a cross-sectional side view of the plate and pad of FIG. 8B with the fixation pad in a locked configuration.
Figure 9A:
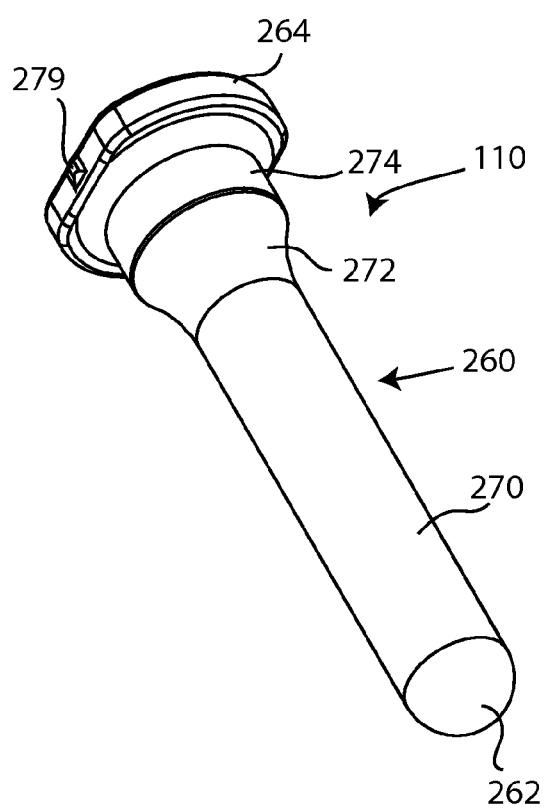
FIG. 9A is an isometric view of a post of the locking mechanism of the spinous process fusion implant of FIG. 1.
Figure 9B:
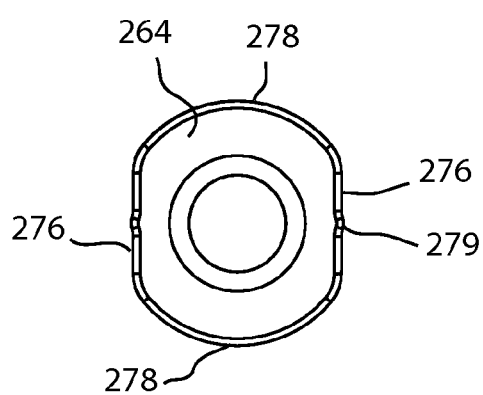
FIG. 9B is an end view of a head of the post of FIG. 9A.

Referring to FIGS. 8A and 8B, a pad 106 is shown captive to a plate 102 in unlocked and locked configurations. In the unlocked configuration shown in FIG. 8A, pad body 230 is partially received within conical socket 139, and stem 232 extends through plate aperture 134. Intact spacer 250 is touching the obverse side of flange 136, which functions as a retainer to retain the pad and prevent unintentional disassembly of the plate from the pad. In this configuration, pad 106 can pivotably and/or rotationally move within conical socket 139 relative to plate 102. However, with the spacer touching the obverse side of the flange, the pad body 230 is held spaced apart from conical socket 139 to prevent unintentional or premature locking between the pad and the plate. The spacer must deform or break in order to position the pad body for locking with the conical socket 139. This arrangement permits the pad to automatically adjust its orientation so that bearing face 238 is aligned with a bone surface before the pad is locked to the plate. In FIG. 8B, pad 106 is in a locked configuration relative to plate 102. Pad body 230 is captured within conical socket 139, with spherical wall 240 in a wedged relationship or frictional lock with frustoconical surface 138, and first side 236 relatively closer to the domed flange 136. Spacer 250 has been deflected toward pad body 230 and is captured between flange 136 and the pad body. In FIG. 8B, pad 106 is shown in a neutral or unrotated position relative to plate 102 in which the first 236 and bearing 242 sides are generally parallel to the obverse side of the plate and axis 107 is generally perpendicular to the obverse side of the plate; however pad 106 could also in a tilted or rotated position relative to plate 102 in the locked configuration, as seen in at least FIG. 2. Pad 106 may also be neutral or tilted relative to the plate while in the unlocked configuration. When in a tilted position relative to the plate, the bearing face 238 may be oblique to the obverse side, as demonstrated in FIG. 2. It is appreciated that one plate 102 may be locked with one or more pads 106, each pad in an independent rotational position relative to the plate. Similarly, extension plate 104 may be locked with one or more pads 106, each pad in an independent rotational position relative to the plate.

A locking mechanism may advantageously lock plates 102 and 104 together in a plate assembly. Referring to FIGS. 1 and 9-11, an embodiment of a locking mechanism 108 may include the pin or post 110, collet 112, and ring 114. As seen at least in FIG. 9A, post 110 includes a shaft 260 extending between a first end 262 and a second end which includes a head 264. First end 262 may be rounded, which may prevent cutting or damage to body tissue in the adjacent environment when implanted. Shaft 260 may further include a straight portion 270, a shoulder 272, and a collar 274 disposed between the straight portion and the head 264, the shoulder providing an increase in shaft diameter between the straight portion 270 and the collar 274. The post head 264 is generally circular; however two straight, or flattened sections 276 are disposed on opposite sides of the head interspersed by two rounded sections 278. The engagement of flattened sections 276 with flattened portions 228 when post 110 is coupled with extension plate 104 prevents rotation of post 110 relative to the plate. Additionally, at least one protusion 279 on the post head 264 frictionally engages the counterbore 224 to rigidly connect the post with the extension plate 104 and prevent rotation. On another embodiment of the invention, the protrusion may be located on the counterbore and engage the post head for connection and/or prevention of rotation. The protrusion may alternately be formed on the head 264, collar 274, shoulder 272, or shaft 260 of the post 110 or on the flattened portions 228 or bore 222 of pin connection feature 220. On yet other embodiments, other features providing a rotation resistant coupling between the post and the plate may be present. One example of a rotation resistant coupling is the coupling between a driver tip and a screw head, of which many are known in the art. Others include keyways, snap fittings, tongue in groove fittings and any other rotation resisting couplings known in the art.

Figure 10A:
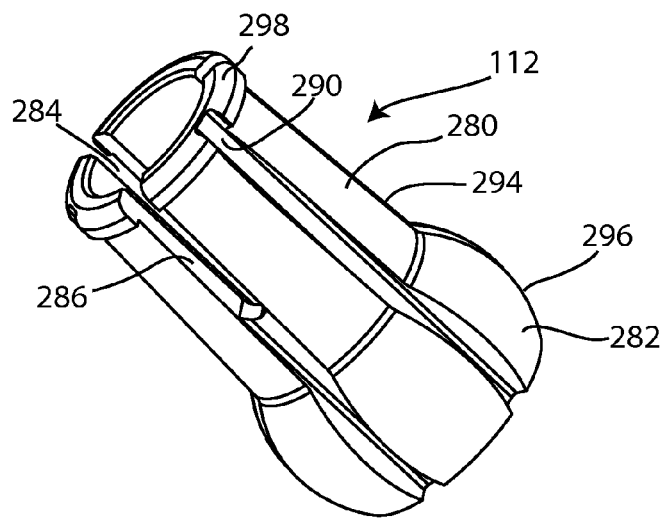
FIG. 10A is an isometric view of a collet of the locking mechanism of the spinous process fusion implant of FIG. 1.
Figure 10B:
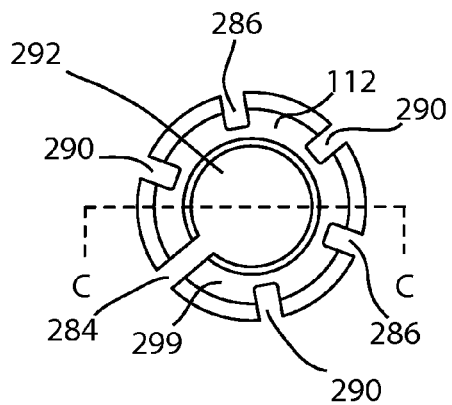
FIG. 10B is an end view of a first end of the collet of FIG. 10A.
Figure 10C:
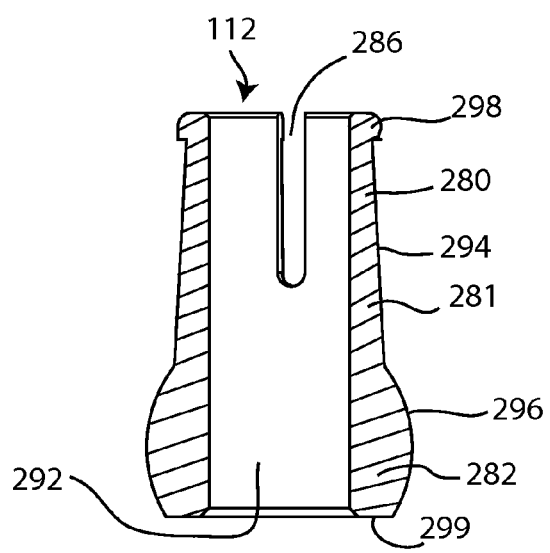
FIG. 10C is a cross-sectional side view of the collet of FIG. 10B taken along section line C-C.

Referring to FIGS. 10A-10C, collet 112 includes a collet body 281 having a a frustoconical shaft portion 280 and a sphere portion 282. The collet 112 is split, having a longitudinal gap 284 extending the entire length of the collet and radially through the collet body, and at least one partial gap 286 extending through the collet body partially along the length of the collet. The longitudinal gap provides flexibility to the collet. The partial gap may selectively increase the flexibility of the collet in the vicinity of the partial gap. A plurality of grooves 290 also extend longitudinally along the length of the collet, but do not extend radially through the collet body 281. The grooves may selectively increase the flexibility of the collet in the vicinity of the grooves, but to a lesser degree than that provided by the partial gap. The collet 112 has a neutral state in which it is relaxed, or undeformed, as seen in FIGS. 10A-10C. In this state, a central bore 292 of the collet has a constant diameter. When acted upon by a force from the inside such as a post in the central bore or a force from the outside such as a ring encircling the collet, the collet may deform and the diameter of the central bore may increase or decrease. The outer surface of the shaft portion is a collet frustoconical surface 294, and the outer surface of the sphere portion 282 is a collet spherical surface 296. The taper of the frustoconical surface 294 may preferably range from 1 to 7 degrees so that the taper is self-locking. More specifically, the taper may range from 2 to 5 degrees. Yet more specifically the taper may be 3 degrees. When the collet is assembled with the plate 102, the rim surface 144 of the plate may engage with the sphere portion 282 to retain collet 112 within bore 140. A collet lip 298 forms one end of the collet adjacent the shaft portion 280. An opposite end of the collet 112 may include a collet flat end 299.

Figure 11A:
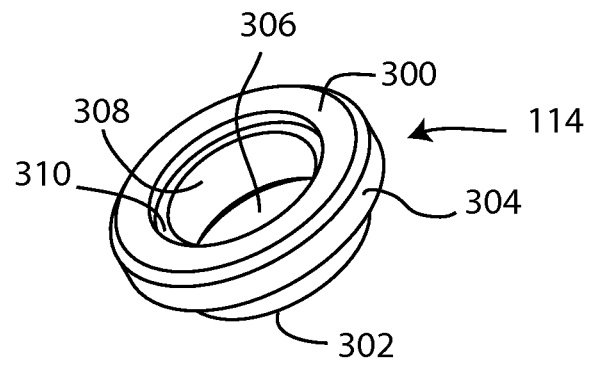
FIG. 11A is an isometric view of a locking ring of the locking mechanism of the spinous process fusion implant of FIG. 1.
Figure 11B:
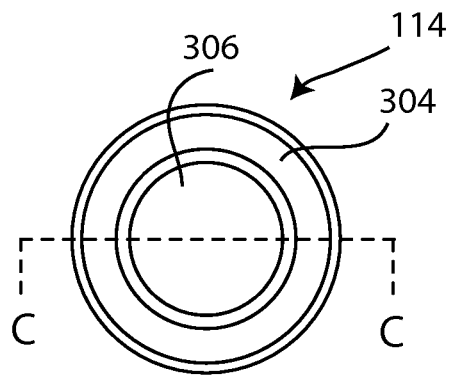
FIG. 11B is an end view of a first end of the ring of FIG. 11A.
Figure 11C:
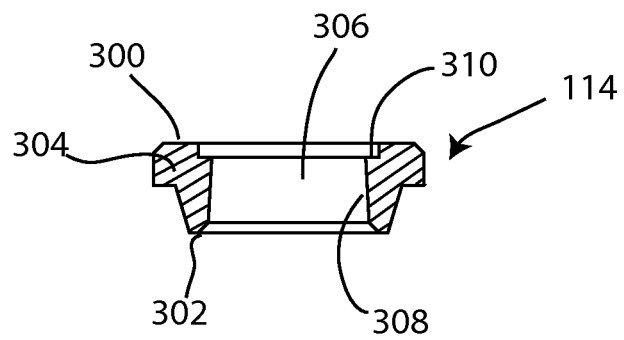
FIG. 11C is a cross-sectional side view of the ring of FIG. 11B taken along section line C-C.

Referring to FIGS. 11A-11C, ring 114 is annular, having a first end 300 and a second end 302. A ring body 304 extends between the two ends, and a ring bore 306 extends through the ring body 304 between the first and second ends. A frustoconical bore wall 308 bounds the bore. A taper or angle of the frustoconical bore wall 308 may be the same as a taper or angle of the collet frustoconical surface 294. The taper of the frustoconical bore wall 308 may preferably range from 1 to 7 degrees so that the taper is self-locking. More specifically, the taper may range 9 from 2 to 5 degrees. Yet more specifically the taper may be 3 degrees. An annular step 310 is adjacent the ring bore 306 at the first end 300. When the ring 114 is assembled with the collet 112, the collet lip 298 may engage with the step 310 to retain ring 114 about the collet 112.

In one embodiment, spinal implant 100 may be provided entirely pre-assembled, with pads 106 in an unlocked configuration and the locking mechanism also unlocked, as seen in FIG. 1. In another embodiment, the implant may be provided in two pre-assembled combinations. In the first combination, plate 102 is assembled with two pads 106 captive to the plate, the intact spacers 250 preventing premature locking of the pads to the plates. Collet 112 is captured in bore 140, but not locked, and ring 114 is retained on collet 112. In the second combination, extension plate 104 is assembled with two pads 106 captive to the plate, the intact spacers 250 preventing premature locking of the pads to the plates. Post 110 is inserted through bore 222 on extension plate 104. An advantage of providing the implant in the two combinations is that different length posts 110 may be substituted intraoperatively as desired to match patient anatomy.

Figure 12:
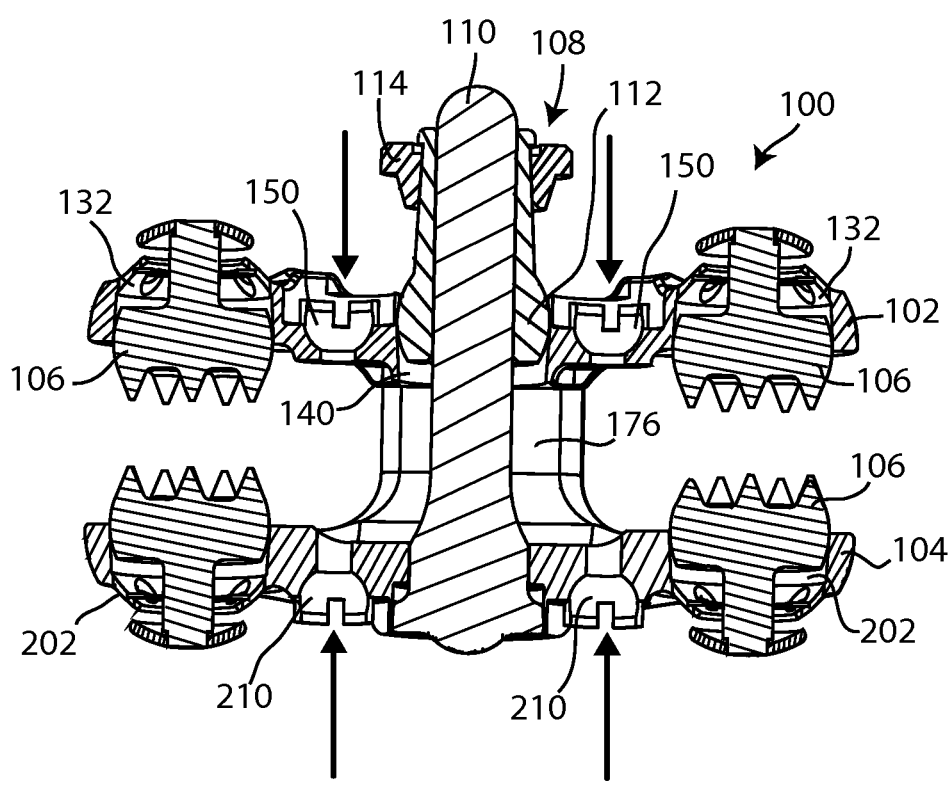
FIG. 12 is a cross-sectional side view of the spinous process fusion implant of FIG. 1 with the fixation pads and locking mechanism in unlocked configurations.
Figure 13:
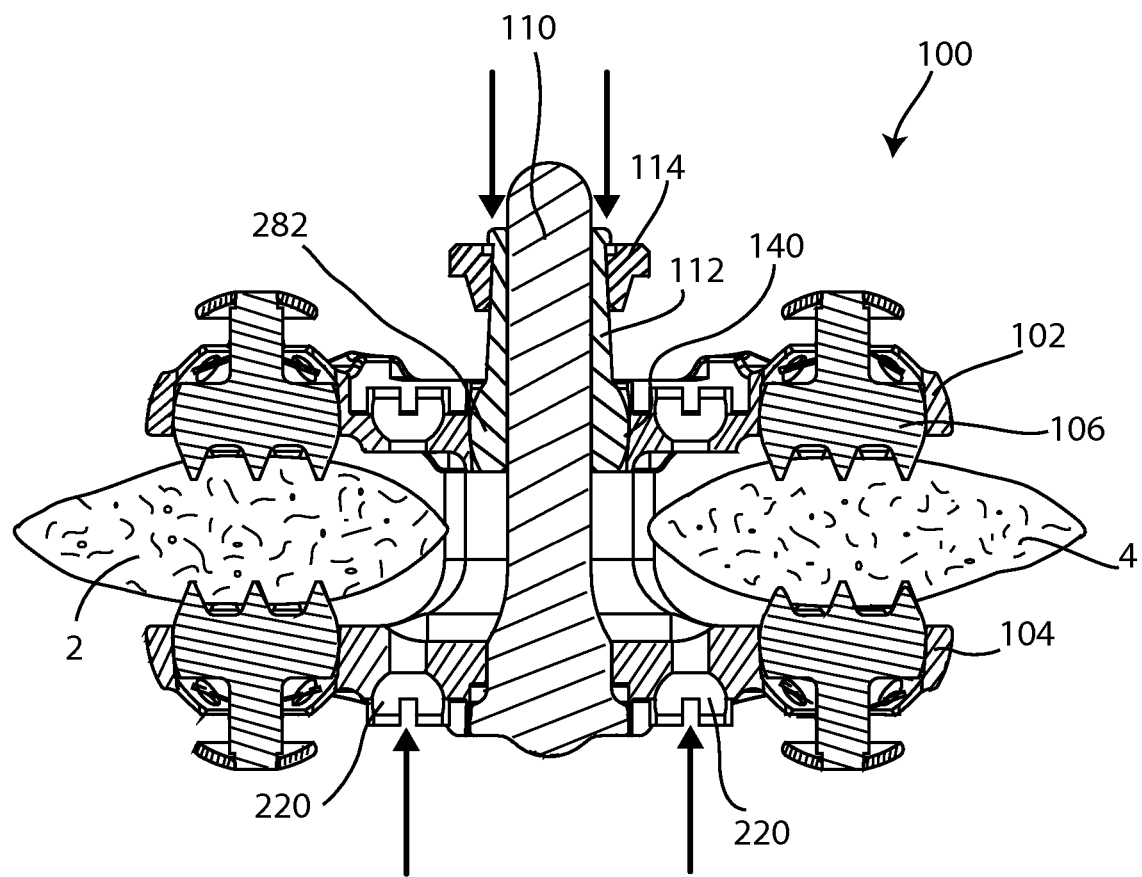
FIG. 13 is a cross-sectional side view of the spinous process fusion implant of FIG. 1 with the fixation pads in a locked configuration and the locking mechanism in a provisionally locked configuration.
Figure 14:
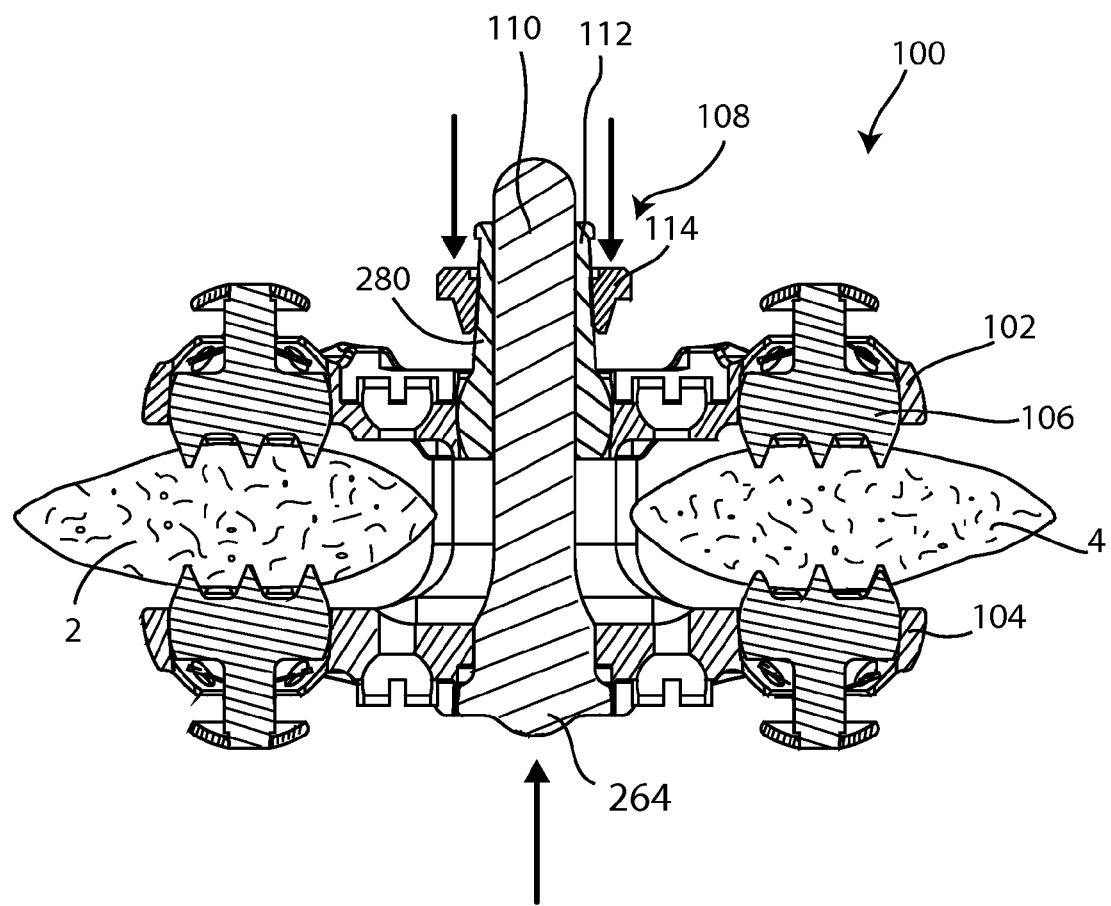
FIG. 14 is a cross-sectional side view of the spinous process fusion implant of FIG. 1 with the fixation pads in a locked configuration and the locking mechanism in a locked configuration.

Referring to FIGS. 12-14, an assembled spinal implant 100 includes plate 102, extension plate 104, a plurality of pads 106, and the locking mechanism 108. FIG. 12 shows a cross-sectional view of implant 100 in an unlocked configuration. In this configuration, a pad 106 is received in each plate polyaxial element 132, 202, but the pads are not yet frictionally locked with the plates. Similarly, collet 112 is received in bore 140, but is not yet frictionally locked within the bore. It is appreciated that although plate 102 is depicted as generally parallel to extension plate 104, the polyaxial connection including sphere portion 282 and bore 140 allows for polyaxial rotation, or tilting, of plate 102 relative to the locking mechanism 108 and extension plate 104. Plate 102, collet 112 and ring 114 may also translate relative to extension a plate 104 in the unlocked configuration. Similarly, each pad 106 can polyaxially rotate or tilt relative to its corresponding polyaxial element 132, 202. This polyaxiality allows for individualized fit of each of the pads 106 against the lateral surfaces of the spinous processes, and of the plates 102, 104 relative to one another and the spinous processes. By way of non-limiting example, if the medial-lateral widths of the spinous processes vary from one another, plate 102 can tilt and be locked in the tilted orientation to provide an individualized fit to the spinous process anatomy. In the same way, the bearing surfaces of the individual pads 106 can advantageously tilt to fit the contour of the specific bony structure, or spinous process surface. This may be advantageous over systems with fixed position plates and/or bearing surfaces by conforming to the natural contours of the bony structures, potentially providing a more conforming fit, reduced implant prominence and reduced interaction or interference with the adjacent body environment. It can be appreciated that, in the final implanted position, plate 104 may be tilted with respect to standard medical planes of reference in order to provide a conforming fit against the spinous processes or other bony surface. However, in the limited context of the spinal implant 100, plate 104 is fixed with respect to the post 110 and thus serves as a frame of reference for movable portions of the spinal implant.

Referring to FIG. 12, the arrows show an initial compression, or pad locking force which, when applied, compresses the two plates 102, 104 together. When the implant 100 is positioned as shown in FIG. 2 with plates 102 and 104 on opposite sides of spinous processes, this compression presses the plates 102, 104 medially toward the spinous processes and seats the pads into the bone of the spinous processes. Initially, when the compression force is low, the plate 102 body and pads are free to rotate in order to align properly to the bone, but as the load is increased, the pads are rigidly and permanently locked to the plate via a spherical taper lock. This initial compression force may be applied gradually by a compression instrument which engages in instrument connection elements 150, 210. As the compression force increases, a spacer deflecting level of force may be reached, followed by a pad locking level of force greater than the spacer deflecting force. In a preferred embodiment, the pad locking level of force may be calibrated so that the pads lock to the plate after the protrusions 246 have sunk into the bone surface, but before the complete bearing faces 238 have indented, or crushed, the bone surface. In other words, the protrusion seating force is lower than the pad locking force, which is lower than the indentation, or crushing force.

Referring to FIG. 13, a cross-sectional view is shown of implant 100 inserted between two spinous processes 2, 4. The initial compression force described with reference to FIG. 12 has been applied, and the pads 106 are wedged, or taper locked, to the plates 102, 104 and seated in the spinous processes 2, 4. In addition, a first locking compression force indicated by the arrows in FIG. 13 has also been applied to press the spherical collet 112 into the tapered bore 140 of the plate body 118. This action wedges the sphere portion 282 of the collet between the bore 140 and the post 110, which locks out the plate polyaxiality and thereby the position of the plate 102. This action also secures the spherical collet 112 to the post 110 to maintain the initial compression between the two opposing plates and the spinous processes. This compressive first locking, or provisional locking force may be applied by a locking instrument which engages the instrument connection elements 210 on extension plate 104, and the collet 112.

Referring to FIG. 14, a cross sectional view shows spinal implant 100 in a second, or final locked configuration. In this second locked configuration, the force indicated by the arrows in FIG. 14 has been applied between post head 264 and the locking ring 114. This final or second locking compression force presses the locking ring 114 along the conical taper of the spherical collet 112, further securing the collet to the post 110. The frustoconical shaft portion 280 of the collet is wedged between the ring 114 and the post 110. This step also advantageously isolates the compression force to the tapered locking mechanism 108 so that no additional or unintentional compression is placed on the spinous processes. The plate 102 and collet 112 are now completely rigidly locked into position. At this point, no rotation or relative movement can a occur between the two plates, or between the plates and the pads.

In a first embodiment of a method of implantation, the entire implant is assembled in the unlocked configuration as seen in FIGS. 1 and 12. The implant, biased in the unlocked configuration, may be connected to an implantation/compression instrument. The instrument may be used to insert the implant between two spinous processes, and pad and plate lockout are carried out as described previously with reference to the description of FIGS. 12-14.

In another embodiment, a first combination of plate 102 with captive pads 106 and captive collet 112 and ring 14 may be connected to one instrument. A second combination of extension plate 104 with pads 106 and post 110 may be connected to a separate instrument. The combinations are inserted into the interspinous area separately, and post 110 is inserted into collet 112 in situ to connect the two combinations. Pad and plate lockout are then carried out as described previously with reference to the description of FIGS. 12-14. An advantage of this embodiment is the ability to preserve important soft tissue structures such as the supraspinous ligament.

Prior to or following the implantation process, natural or synthetic bone graft material, a bone block, bone morphogenic protein, and/or other therapeutic agents may be inserted into the chamber 115. These materials may be inserted through window 178, or packed around post 110 before final assembly of the implant.

Implant members according to exemplary embodiments may be manufactured from suitable medical-grade materials, including, but not limited to, titanium and stainless steel, other a metals, polymers, or ceramics.

Figure 15:
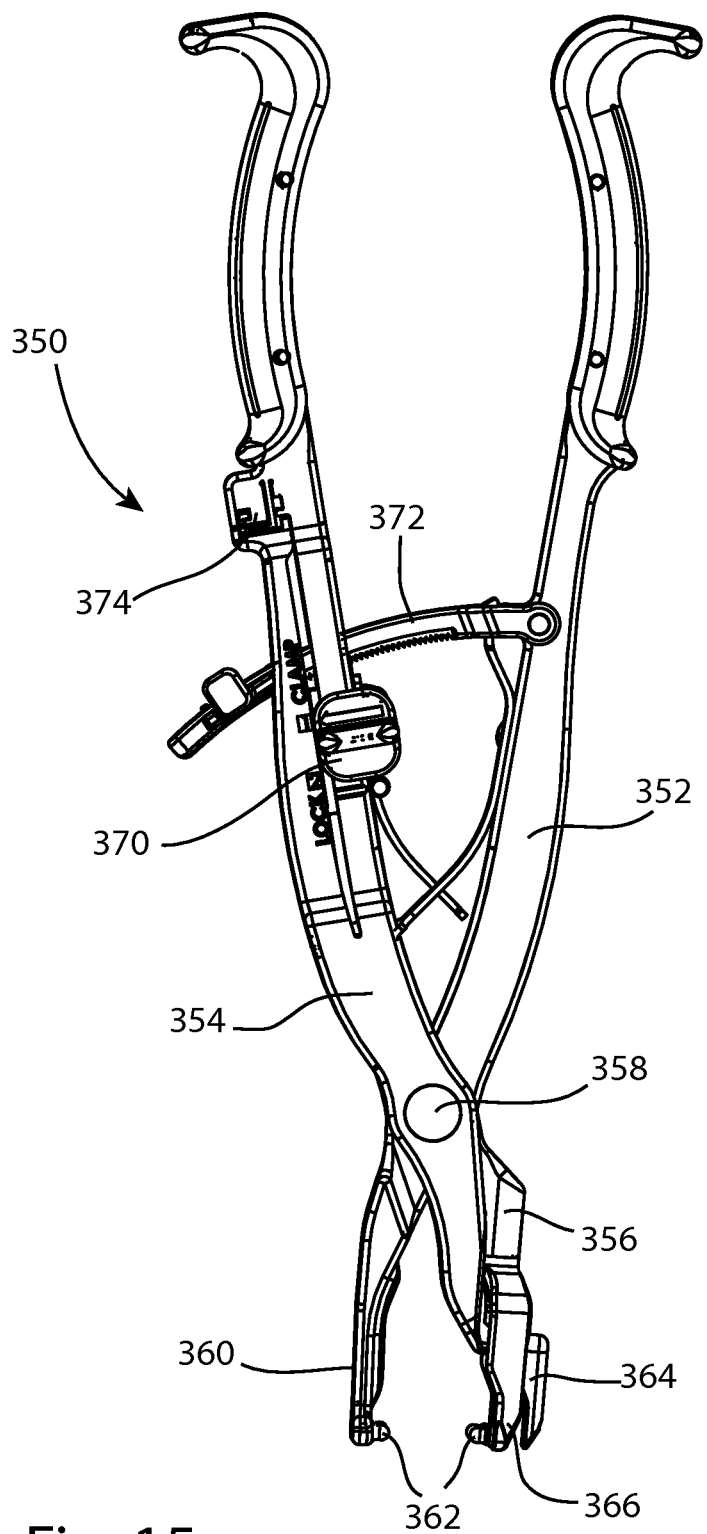
FIG. 15 is a side view of a first, or primary, instrument for providing insertion, compression and locking.
Figure 16:
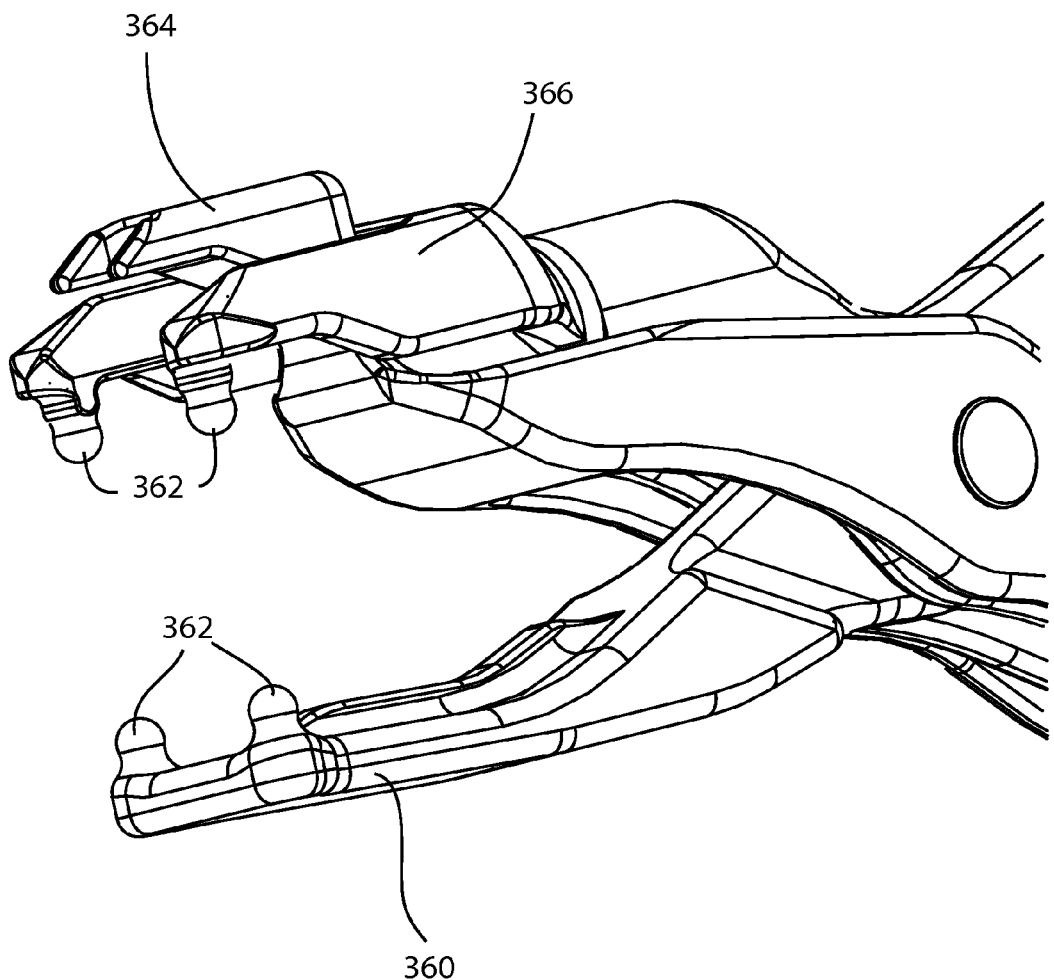
FIG. 16 is an isometric view of a working end of the first instrument of FIG. 15.
Figure 17:
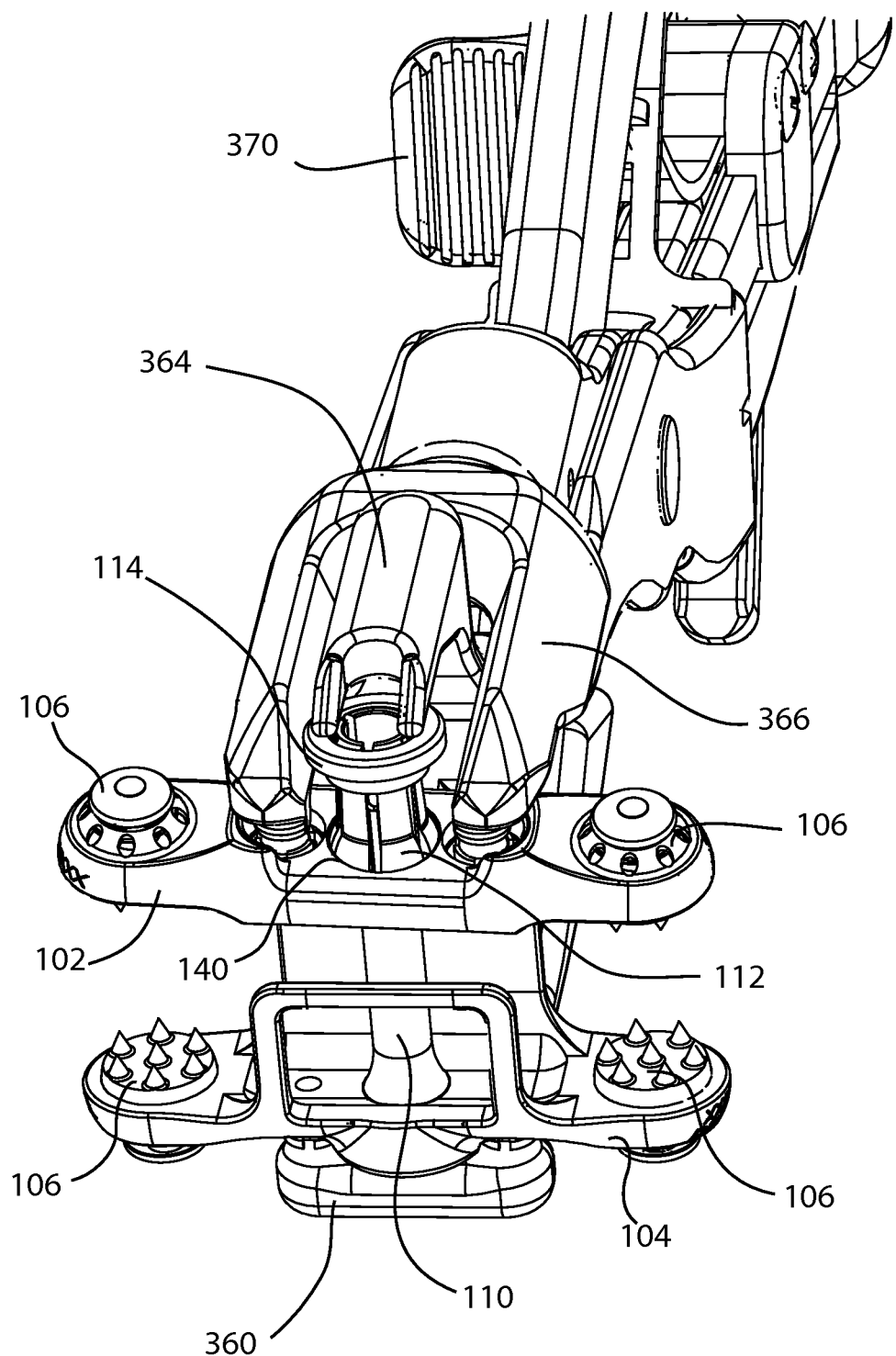
FIG. 17 is an isometric view of the working end of the first instrument of FIG. 16, the instrument holding the spinous process fusion implant of FIG. 1 in an unlocked configuration.

FIGS. 15, 16 and 17 illustrate a first instrument 350 which may be used to provide insertion, compression and locking of spinal implant 100 or other related embodiments. The first instrument 350 may also be described as a primary instrument 350. This instrument and its operation are described in detail in U.S. Provisional Patent Application Ser. No. 61/366,755, the entirety of which is incorporated by reference in this document.

First instrument 350 includes a first leg 352, second leg 354 and third leg 356 which are pivotable relative to one another about a pivot point 358. A first leg working end 360 includes spherical tips 362 which may engage instrument connection elements on an implant, such as instrument connection elements 150, 220 on spinal implant 100. A second leg working end 364 is forked, and the fork may be sized to engage a portion of collet 112 on spinal implant 100. A third leg working end 366 also includes spherical tips 362 which may engage instrument connection elements on an implant. Third leg working end 366 is rotatable relative to the first 360 and second 364 working ends, which allows for polyaxial adjustment of spinal implant 100 prior to locking the fixation pads 106 and central locking mechanism 108. The spherical tips 362, instrument connection elements 150, 222, and rotatable working end 366 allow the implant to align itself to the anatomy of the patient along multiple axes as compression is applied, providing the best possible surface contact area between the implant and the bone.

A selector switch 370 is actuable between a first position and a second position. When the selector switch is in the first position and the instrument is actuated by moving the handles toward one another, the second 364 and third 366 leg working ends move together, the third leg working end 366 applying a compressive force in opposition to the first leg working end 360. The third leg working end 364 may rotate or pivot to allow the implant to properly orient itself to the geometry of the bone as the compressive force is applied. The second leg working end 364 remains in a position where it is not applying any compressive force. The compressive force between the first and third legs is maintained by a ratcheting arm 372. When the switch is moved to the second position and the instrument is actuated by moving the handles toward one another, the second 364 and third 366 leg working ends become disengaged. The second leg working end 364 is then free to move independently of the third leg working end 366 and can apply a compressive locking force to a central member 108 of the implant, locking it in place.

As shown in FIG. 17, first instrument 350 may be used to grip implant 100, with spherical tips 362 on the instrument engaging in socket-like cups 154 on plates 102, 104. The first leg working end may be connected to extension plate 104, and third leg working end connected to plate 102. The instrument may be used to lift the implant 100 from packaging or a table, and insert into the interspinous space between the spinous processes. With the selector switch 370 in the first position, the instrument handles may then be compressed together, clamping plates 102, 104 toward one another and the spinous processes as seen in FIG. 12. The third leg working end 366 may pivot to allow pivoting adjustment of plate 102 relative to the spinous processes. Also, plate 102 may translate along post 110 toward extension plate 104. As compression force is applied, a first force level sufficient to deform the spacers 250 may be reached, followed by a second force level, greater than the first force level, sufficient to lock the pads 106 relative to the plates 102, 104. The switch 370 may then be moved to the second position, disengaging the second and third leg working ends from one another. The instrument handles may then be compressed together again, with a locking force now being applied between the extension plate 104 and the collet 112, as seen in FIG. 13. This locking force is isolated so that no additional force is applied between extension plate 104 and plate 102. Collet 112 is wedged into bore 140 of plate 102, locking out movement between the collet 112, post 110, and plate 102. A force indicator 374 may provide an indication such as an audible signal when selected levels of force are reached. Other embodiments of the invention may include other force indicators known in the art including but not limited to markings or stops.

Figures 18A, 18B:
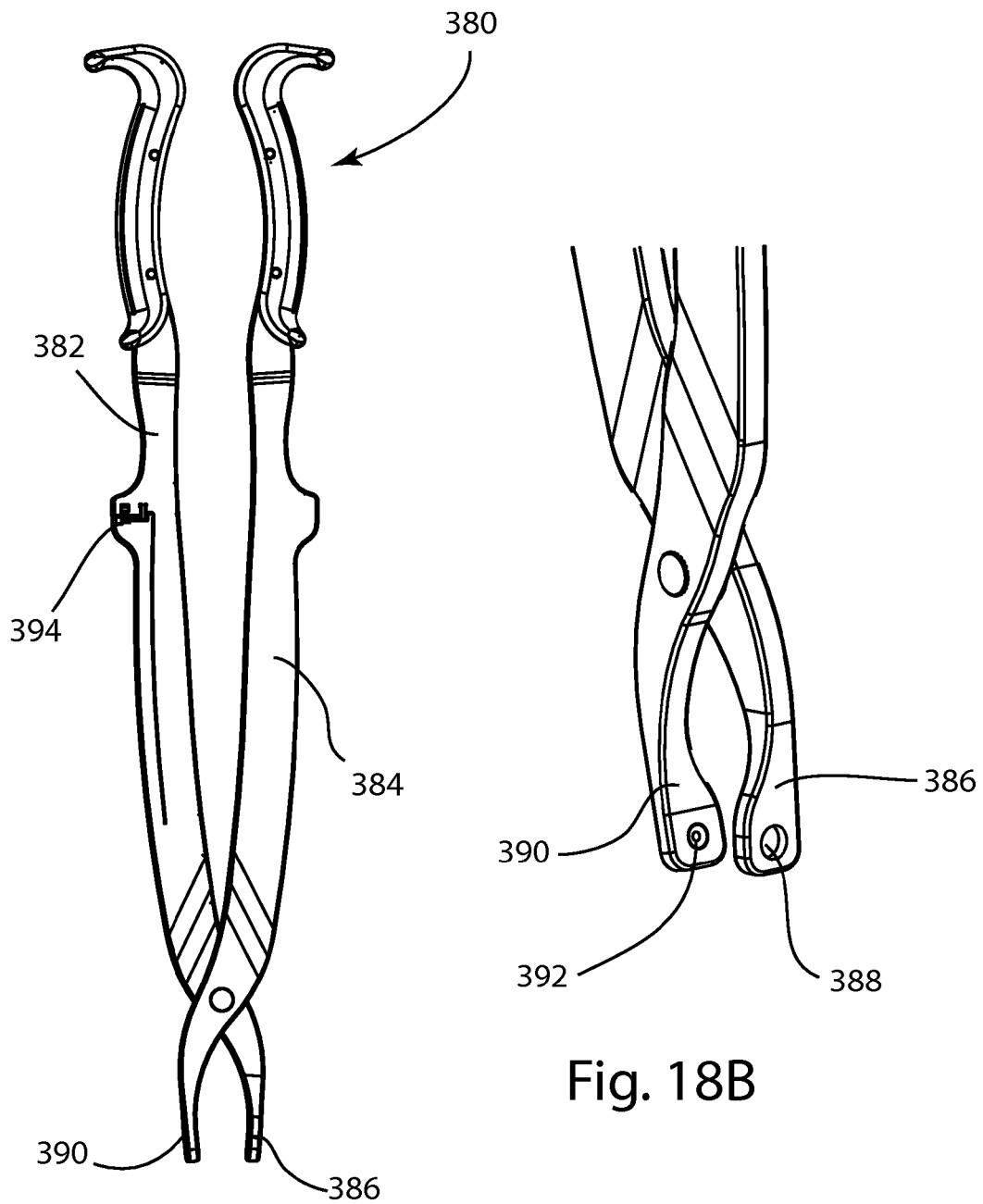
FIG. 18A is a side view of a secondary instrument for providing locking force.
FIG. 18B is an isometric view of a working end of the instrument of FIG. 18A.
Figure 19:
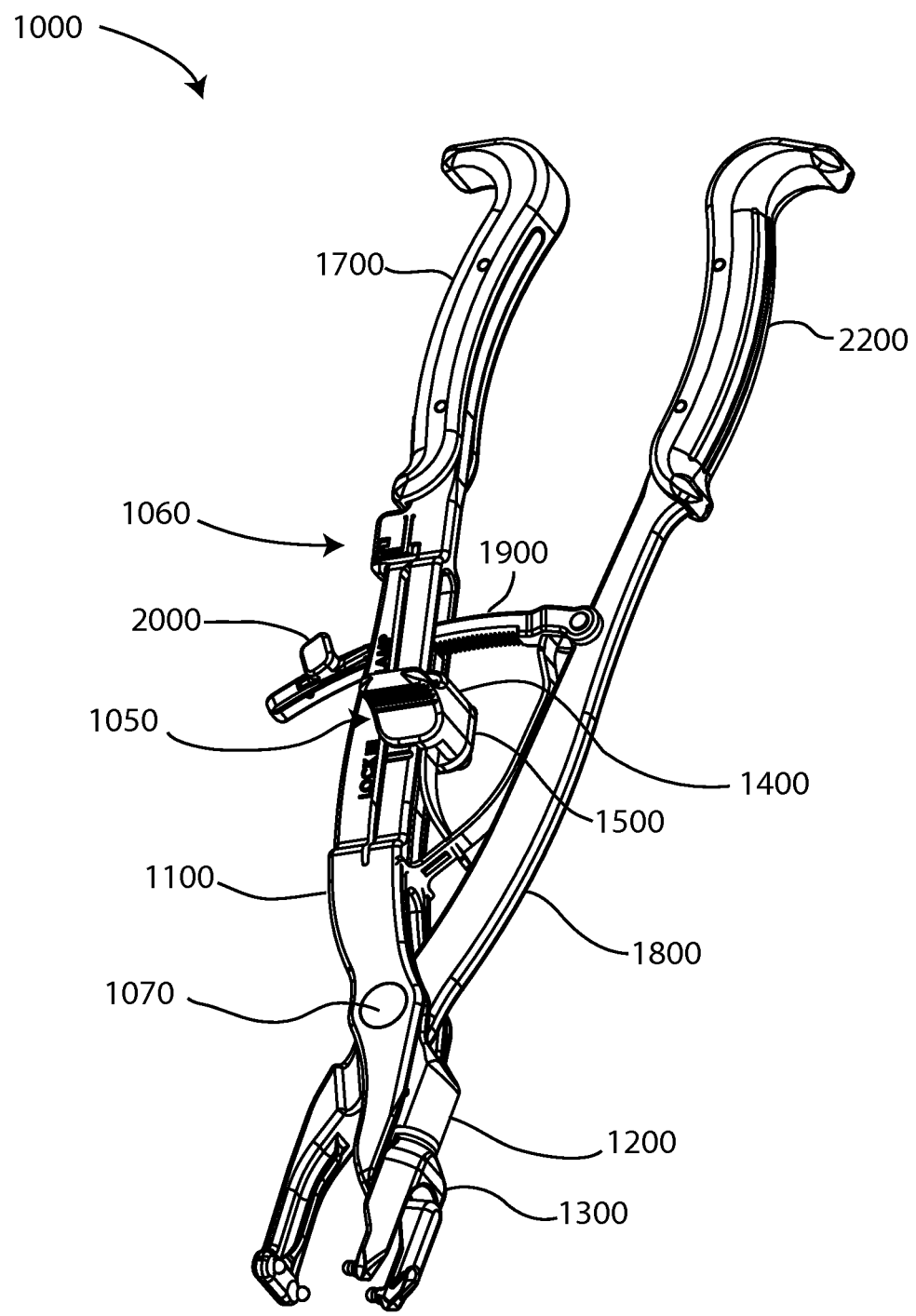
FIG. 19 is a perspective view of a second example of a first, or primary, instrument.

Referring to FIGS. 18A and 18B, a second instrument 380 may be used to move locking ring 114 relative to the collet 112 on spinal implant 100 to provide an additional or final lockout of the locking mechanism 108. Second instrument 380 includes a first leg 382 pivotably connected to a second leg 384. A first leg working end 386 includes a first feature to engage ring 114 of implant 100. In an embodiment, the first feature is an opening 388 sized fit around post 110 and engage ring 114 without engaging collet 112, allowing the instrument to urge the ring 114 to move relative to the collet 112. A second leg working end 390 includes a second feature to engage post 110. In an embodiment, the second feature is a recess 392 sized to receive a portion of post head 264. The instrument 380 may be positioned with spinal implant 100 so that the first leg working end 386 engages the ring 114 and the second leg working end 390 engages the post 110. The handles may be moved toward one another to provide a force to move ring 114 along collet 112, further locking the locking mechanism 108, as seen in FIG. 14. A force indicator 394 may provide an indication such as an audible signal when a selected level of force is reached.

Referring to FIGS. 19-37, a second example of a first, or primary, instrument 1000 is illustrated. Primary instrument 1000 may be used to provide insertion, compression and locking of spinal implant 100 or other related embodiments, and may resemble first instrument 350. Primary instrument 1000 may include a lock/pivot leg sub-assembly 1010, a rigid leg sub-assembly 1040, a clamp/lock selector sub-assembly 1050, a force indicator 1060, and a main pivot fastener 1070 to secure the lock/pivot leg sub-assembly and the rigid leg sub-assembly so that the lock/pivot leg sub-assembly is rotatable relative to the rigid leg sub-assembly about a center longitudinal axis of the fastener 1070.

Figure 20:
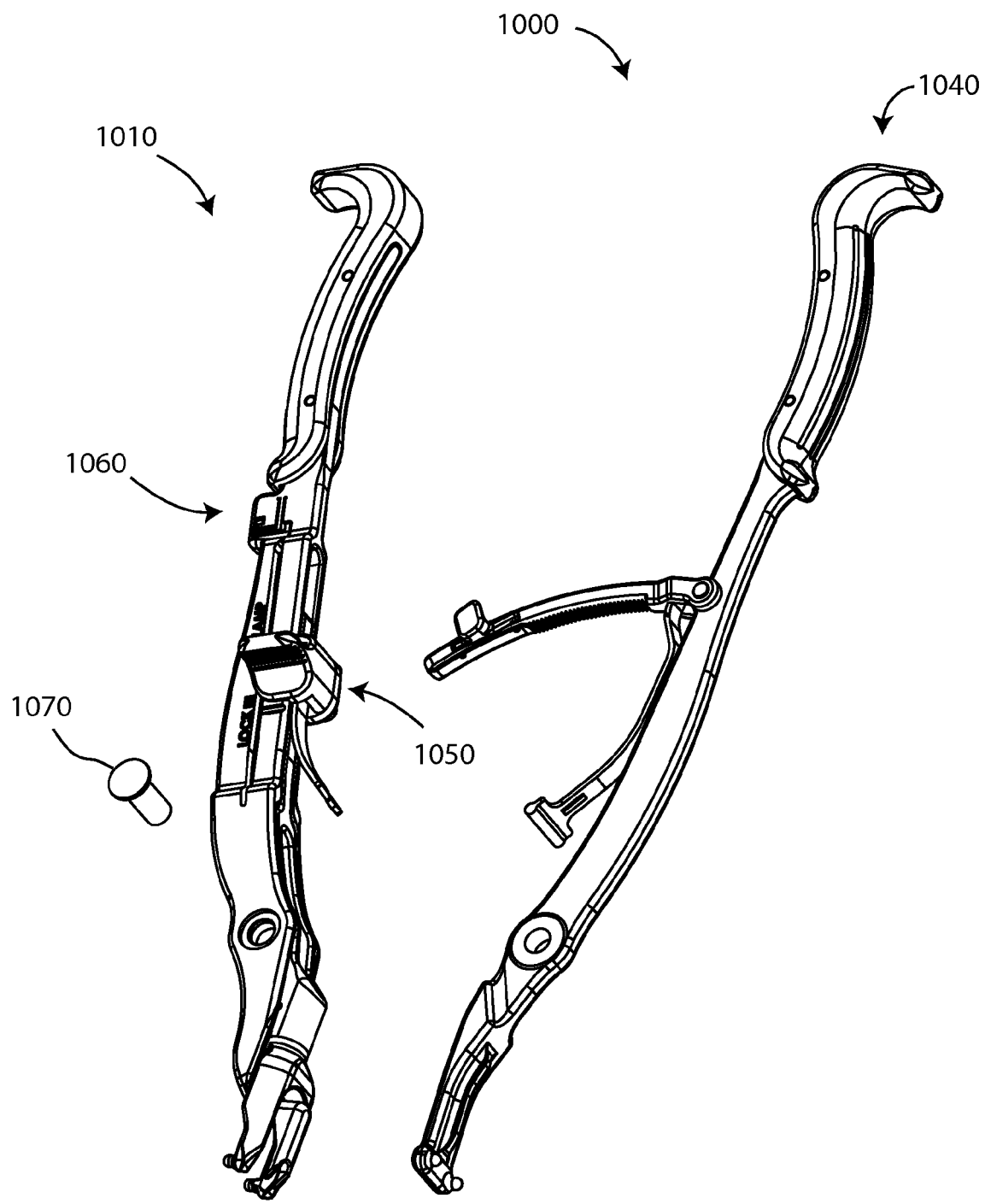
FIG. 20 is an exploded perspective view of the primary instrument of FIG. 19, illustrating a lock/pivot leg sub-assembly, a rigid leg sub-assembly, and a main pivot fastener.
Figure 21:
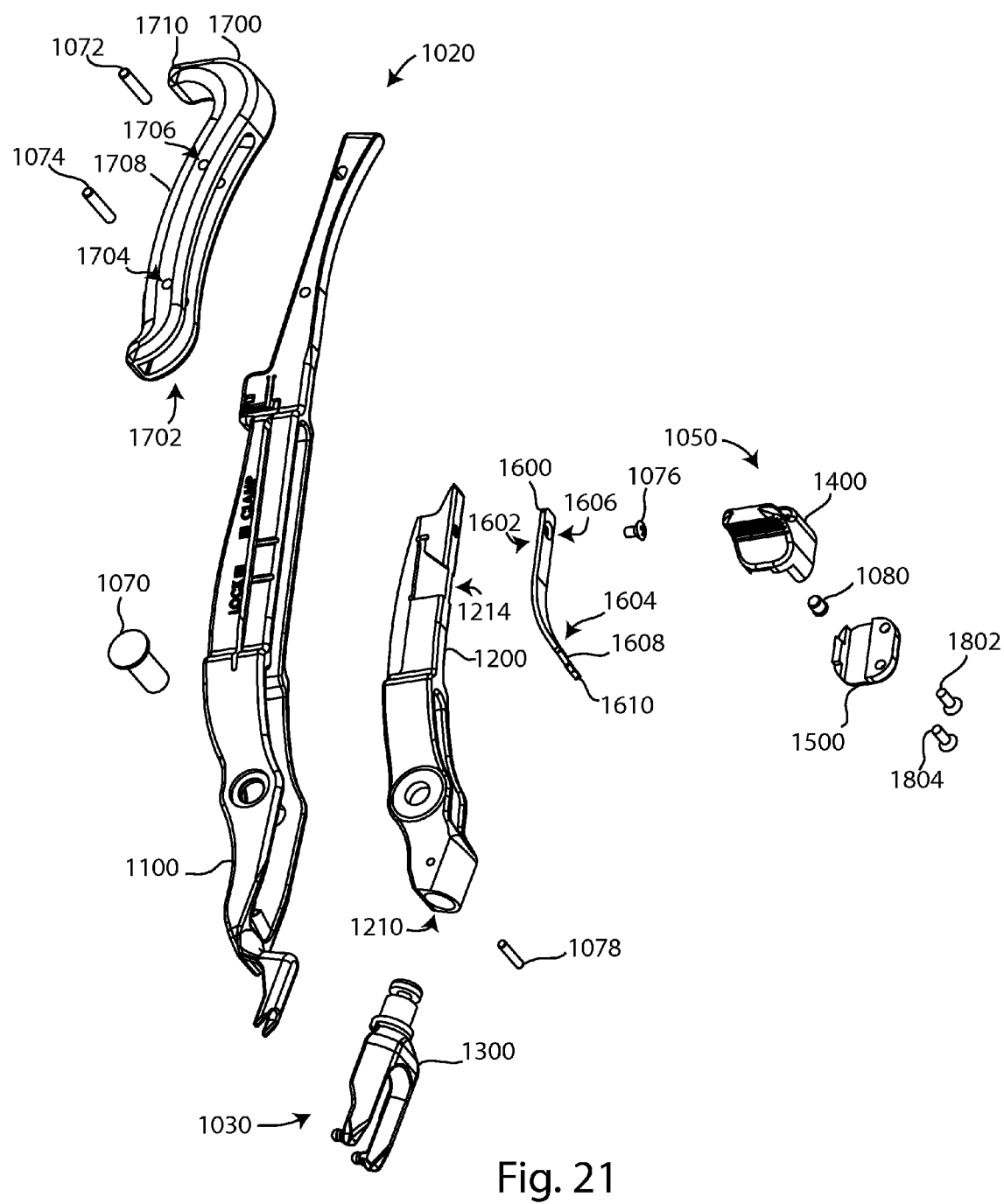
FIG. 21 is an exploded perspective view of the lock/pivot leg sub-assembly and the main pivot fastener of FIG. 20, illustrating a lock leg, a pivot leg, a pivot head, a selector body, a selector back plate, a short spring, and a grip.

Referring to FIGS. 20-21, the lock/pivot leg sub-assembly 1010 may include a lock leg sub-assembly 1020, a pivot leg sub-assembly 1030, the clamp/lock selector sub-assembly 1050, and the force indicator 1060.

The lock leg sub-assembly 1020 may include a lock leg 1100, a grip 1700, the force indicator 1060, and fasteners 1072, 1074 to secure the grip to the lock leg.

The pivot leg sub-assembly 1030 may include a pivot leg 1200, a pivot head 1300, a short spring 1600, a fastener 1076 to secure the short spring to the pivot leg, and fastener 1078 to secure the pivot head to the pivot leg so that the pivot head is rotatable relative to the pivot leg about at least one axis. The pivot leg sub-assembly may resemble third leg 356.

The clamp/lock selector sub-assembly 1050 may include a selector body 1400, a selector back plate 1500, a ball detent 1080 carried by the selector body, and fasteners 1082, 1084 to secure the selector back plate to the selector body. The clamp/lock selector sub-assembly 1050 may resemble selector switch 370.

Figure 22:
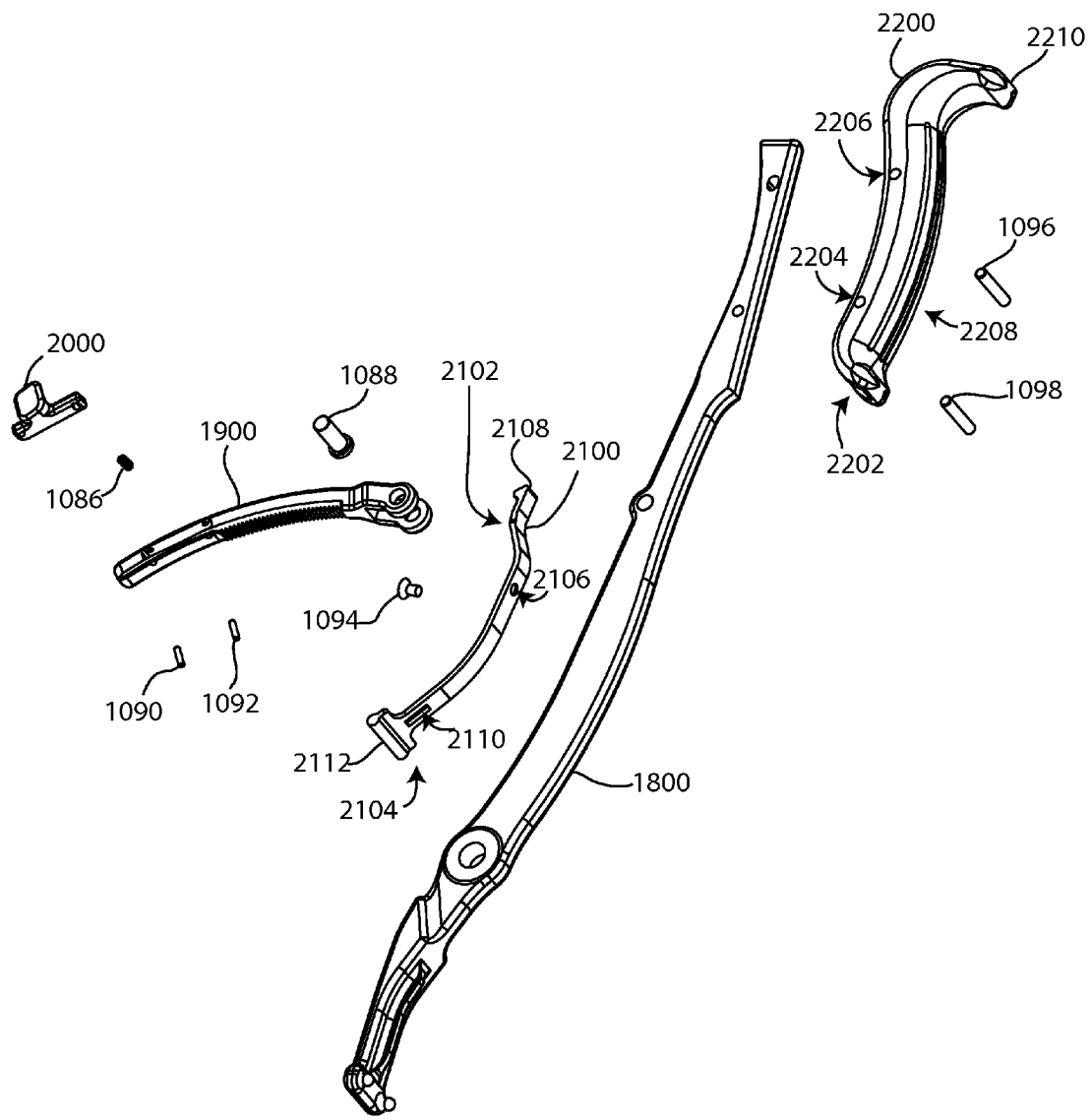
FIG. 22 is an exploded perspective view of the rigid leg sub-assembly of FIG. 20, illustrating a rigid leg, a ratchet arm, a button, a long spring, and a grip.

Referring to FIGS. 20 and 22, the rigid leg sub-assembly 1040 may include a rigid leg 1800, a ratchet arm 1900, a button 2000, a long spring 2100, a grip 2200, spring 1086 to bias the button to protrude from the ratchet arm, fastener 1088 to secure the ratchet arm to the rigid leg so that the ratchet arm is rotatable relative to the rigid leg about at least a center longitudinal axis of the fastener 1088, fasteners 1090, 1092 to secure the button to the ratchet arm, fastener 1094 to secure the long spring to the rigid arm, and fasteners 1096, 1098 to secure the grip to the rigid arm.

Referring to FIGS. 23A-C, the lock leg 1100 may be an elongated member with a working portion 1102, a grip portion 1104 opposite the working portion, a first hole 1106 between the working portion and the grip portion, and second and third holes 1110, 1112 in the grip portion. The lock leg 1100 may resemble the second leg 354. The lock leg 1110 may be a bilaterally symmetric about a center plane 1101. The working portion 1102 may also be described as a jaw. The grip portion 1104 may also be described as a handle portion. The working portion 1102 may terminate in a fork 1114, which may also be described as a bifurcation. The fork 1114 may be wide enough to receive end 262 of post 110 with little clearance. The fork 1114 may be laterally offset relative to the remainder of the lock leg 1100. The lock leg 1100 may include an aperture 1120 transverse to the holes 1106, 1110, 1112. The aperture may intersect the hole 1106. The lock leg 1100 may include two or more grooves 1122 between the holes 1106 and 1110. Bilateral grooves 1122 may be present. Text 1124 and/or other indicia 1126 may be included proximate the grooves.

Figures 36A, 36B:
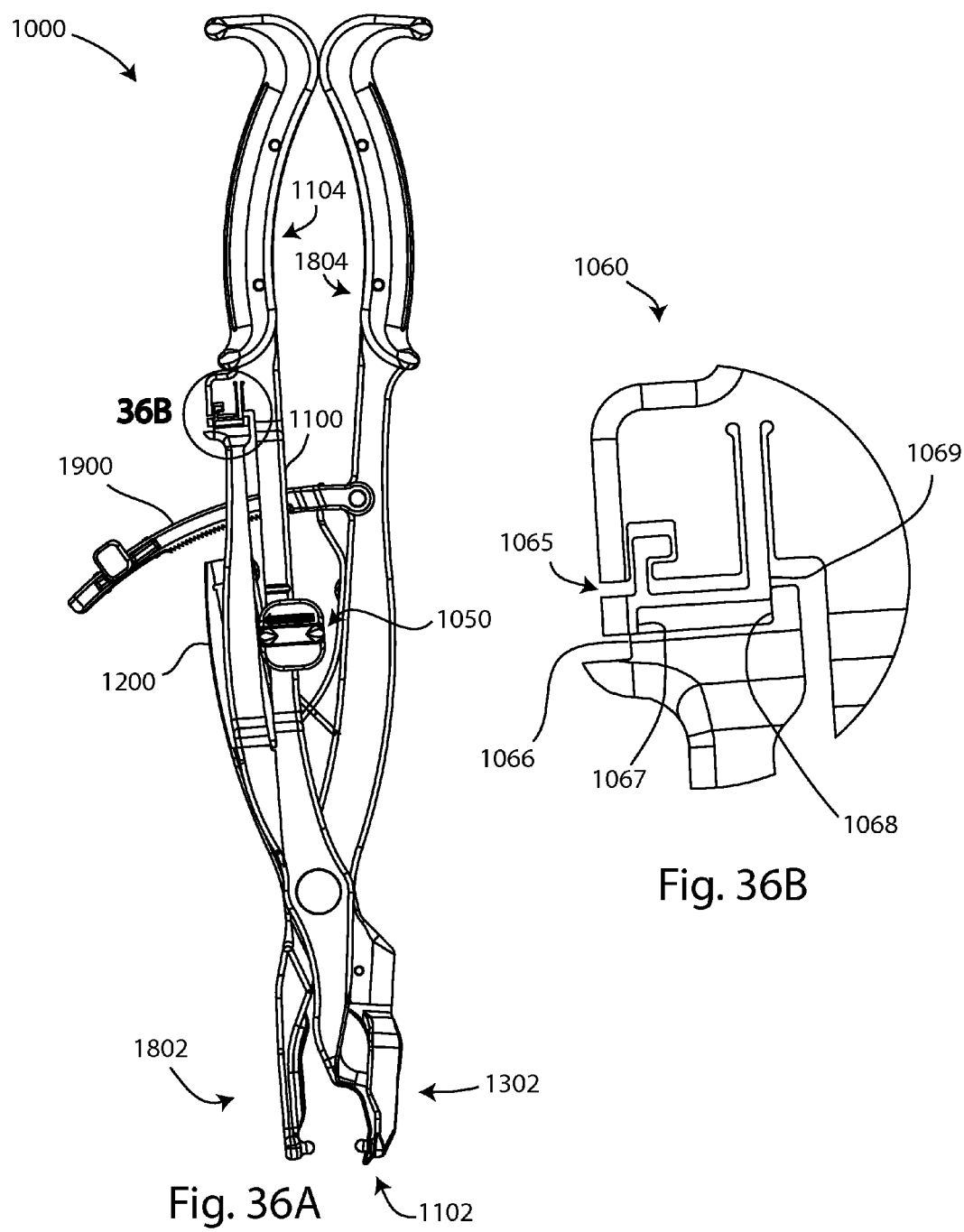
FIG. 36A is a front view of the primary instrument of FIG. 19 in a configuration in which the lock and rigid legs are fully closed and the force indicator is in an actuated position.
FIG. 36B is an enlarged detail view of a portion of the primary instrument, as indicated by the circle 36B in FIG. 36A.

The lock leg 1100 may include the force indicator 1060. In this example, the force indicator 1060 is integrally formed as part of the lock leg 1100, although non-integral examples are contemplated. The force indicator 1060 may resemble the force indicator 374. FIG. 23B shows the force indicator 1060 in a free state, while FIG. 36B shows the force indicator 1060 in a deployed state. The force indicator 1060 may include at least one arm 1062 which protrudes from the lock leg 1100 and terminates in a tip portion 1064. The tip portion 1064 may include a strike portion 1066 and a restraint portion 1068. The force indicator 1060 may also include an enlargement 1063 which protrudes from the lock leg 1100 adjacent to the tip portion 1064. The enlargement 1063 may include a strike portion 1067 and a restraint portion 1069. The enlargement 1063 may also include a relief channel 1065 to increase the mobility of the strike portion 1067 and the restraint portion 1069. In this example, the force indicator 1060 may be formed by one or more wire electrical discharge machining (wire EDM) cuts through the lock leg 1100.

The grip 1700 may have a channel 1702 formed in an elongated side of the grip and first and second holes 1704, 1706 which extend through the grip and intersect the channel. A second side 1708 of the grip 1700 opposite the channel 1700 may be broad and gently rounded to present a comfortable surface for contact by a portion of a user's hand. One or more finger rests 1710 may be formed on the grip 1700. The grip 1700 may be at least partially formed of a resilient material to increase user comfort, although stiff materials may also be used.

The lock leg sub-assembly 1020 may be assembled by sliding the grip portion 1104 into the channel 1702, inserting fastener 1072 in holes 1706, 1112, and inserting fastener 1074 in holes 1704, 1110.

Figure 24A:
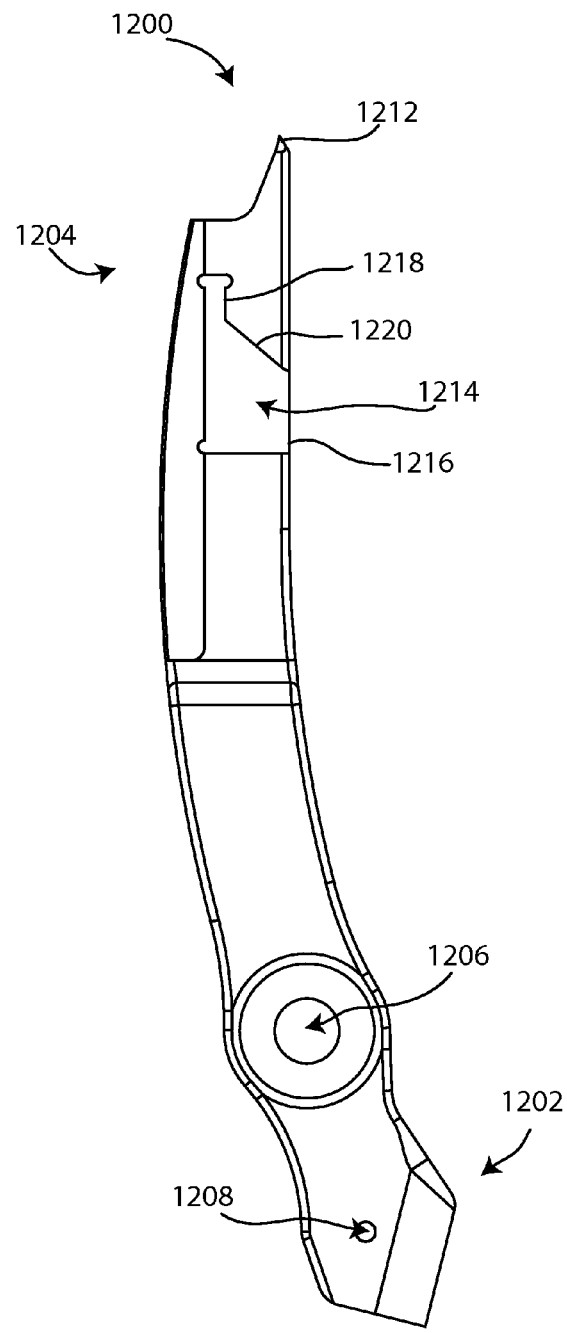
FIG. 24A is a front view of the pivot leg of FIG. 21.
Figure 24B:
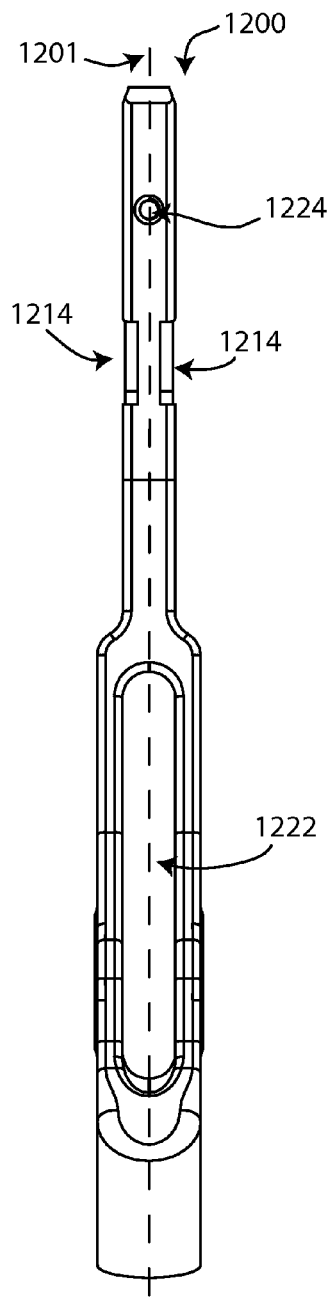
FIG. 24B is a side view of the pivot leg of FIG. 24A.

Referring to FIGS. 24A-B, the pivot leg 1200 may be an elongated member with a working portion 1202, a rear portion 1204 opposite the working portion, and a first hole 1206 between the working portion and the rear portion. The pivot leg 1200 may share some or all of the characteristics of third leg 356. The pivot leg 1200 may be bilaterally symmetric about a center plane 1201. The working portion 1202 may include a second hole 1208 parallel to hole 1206 and a third hole 1210 transverse to the holes 1206, 1208. In this example, hole 1210 is perpendicular to hole 1206, although other orientations are contemplated. The rear portion 1204 may terminate in a tooth 1212. One or more alcoves 1214 may be included in the rear portion between the tooth 1212 and the hole 1206. The alcoves 1214 may also be described as recesses or indentations. Each alcove 1214 may include a wide portion 1216 and a narrow portion 1218. The wide and narrow portions 1216, 1218 may be connected by a transition portion 1220. The wide portion 1216 may break through a side wall of the pivot leg 1200, as may be best appreciated in FIG. 21. In this example, the pivot leg 1200 includes bilateral alcoves 1214 with the narrow portions 1218 closer to the tooth 1212 and with tapered transition portions 1220. The rear portion 1204 may also include a blind hole 1224 proximate the tooth 1212 and transverse to the holes 1206, 1208. The lock leg 1100 may include an aperture 1222 transverse to the holes 1206, 1208. The aperture may intersect the hole 1206.

Figures 25A, 25B:
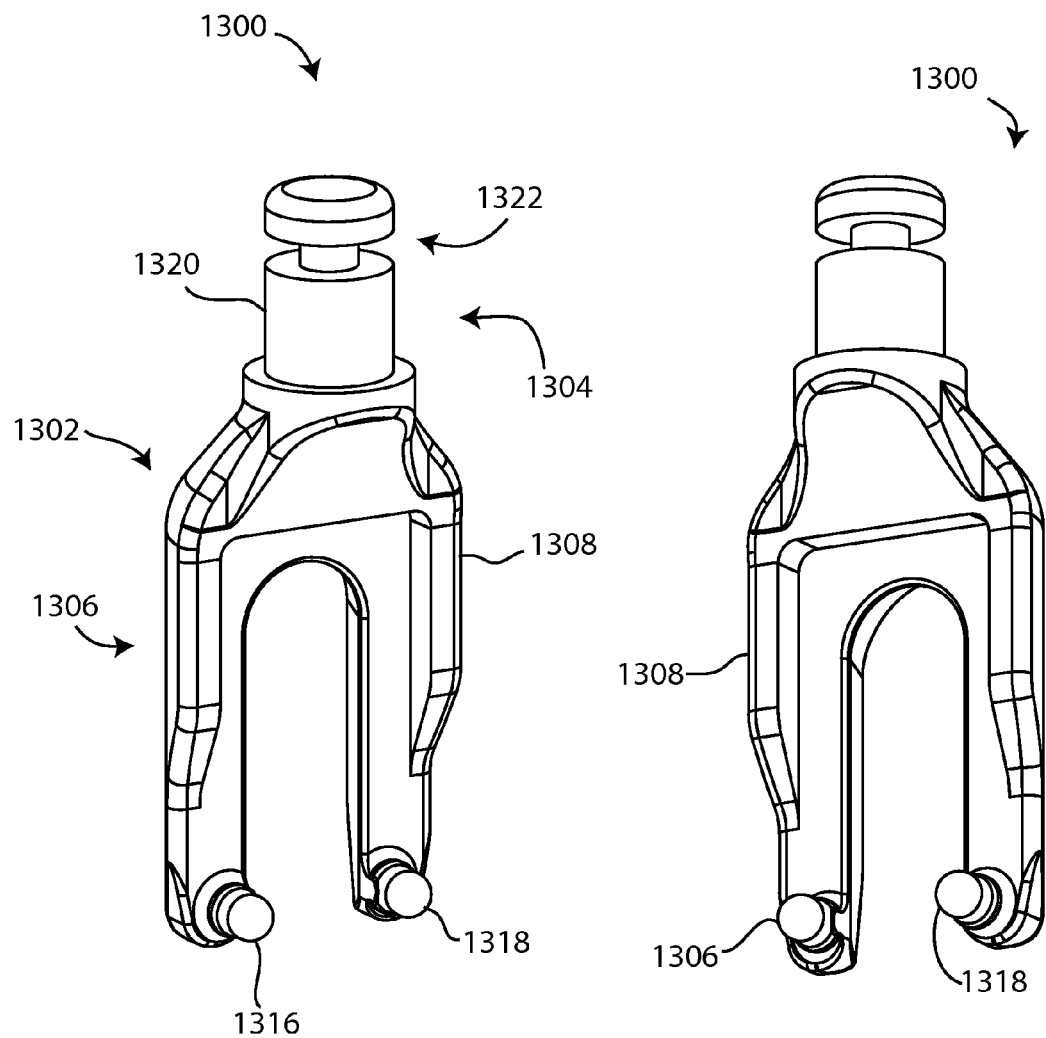
FIG. 25A is a perspective view of the pivot head of FIG. 21.
FIG. 25B is another perspective view of the pivot head of FIG. 25A from a different angle.

Referring to FIGS. 25A-B, the pivot head 1300 may be a forked member with a working portion 1302 and a shaft portion 1304. The pivot head 1300 may resemble the third leg working end 366. The working portion 1302 may also be described as a jaw. The working portion 1302 may include a fork 1306, which may also be described as a bifurcation. The working portion 1302 may be wider than the shaft portion 1304. Ribs 1308 may extend along each prong of the fork 1306. The working portion 1302 may also include one or more spherical protrusions 1316. For example, two spherical protrusions 1316, 1318 are positioned near each free end of the fork 1306 on the same side as the ribs 1308. In this example, a line or axis may be drawn through the spherical centers of the protrusions 1316, 1318 generally perpendicular to the direction in which the spherical protrusion 1316 extends. The shaft portion 1304 may include a shaft 1320. A groove 1322 may be incised around the outside diameter of the shaft 1320. A center longitudinal axis of the shaft 1320 may extend generally perpendicular to the direction in which the spherical protrusion 1316 extends, and to the line or axis through the spherical centers of the protrusions 1316, 1318.

The short spring 1600 may be an elongated ribbon-like member with a first portion 1602 and a second portion 1604. The short spring 1600 may include a through hole 1606 located proximate a free end of the first portion 1602. A free end of the second portion 2104 may include a narrow neck 1608 terminating in an enlarged tab 1610.

The pivot leg sub-assembly 1030 may be assembled by inserting shaft 1320 into hole 1210 and inserting fastener 1078 into hole 1208 so that fastener 1078 rests in groove 1322. Fastener 1076 may be inserted through hole 1606 and into hole 1224 to secure short spring 1600 to the pivot leg 1200 so that tab 1610 is proximate hole 1808. Short spring 1600 may be pre-curved during fabrication or bent during assembly so that tab 1610 curves away from pivot leg 1200. While the illustrated example provides a single axis of rotation between the pivot leg 1200 and the pivot head 1300, other examples which provide two or more axes of rotation are contemplated.

Referring to FIGS. 26A-C, the selector body 1400 may include a first portion 1402, a second portion 1404, and a middle portion 1406. The first portion 1402 may present a textured protruding surface for contact with a portion of a user's hand, such as a fingertip. The first portion 1402 may also include an arrow 1408 or other indicia. The middle portion 1406 may form a base for the first portion 1402. The middle portion 1406 may include a blind hole 1410 on a side opposite the first portion 1402. The second portion 1404 may include a tall protrusion 1412 extending from the middle portion 1406 beside the hole 1410. A blind hole 1414 may be included in a free end of the tall protrusion 1412. In this example, a second blind hole 1416 is also present. The second portion 1404 may include a short protrusion 1418 extending from the middle portion 1406 beside the hole 1410 and across from the tall protrusion 1412. The short protrusion 1418 may terminate in a reduced tip portion 1420. Tip portion 1420 may be resemble a trapezoid and may be oriented with a short side 1422 proximate the hole 1410 and a long side 1424 opposite the short side 1422. At least one tapered side 1426 may be present.

Referring to FIGS. 27A-C, the selector back plate 1500 may include a body portion 1502. A first protrusion 1512 may extend from the body portion 1502, and may share an exterior side with the body portion. A blind hole 1514 may be included in a free end of the first protrusion 1512. In this example, a second blind hole 1516 is also present. A second protrusion 1518 may extend beside the first protrusion 1512, and may share a second exterior side with the body portion 1502, the second exterior side opposite the first exterior side. The second protrusion 1518 may terminate with a reduced tip portion 1520. Tip portion 1520 may be resemble a trapezoid and may be oriented with a short side 1522 proximate the first protrusion 1512 and a long side 1524 opposite the short side 1522. At least one tapered side 1526 may be present.

The lock/pivot leg sub-assembly 1010 may be assembled by inserting rear portion 1204 of the pivot leg sub-assembly 1030 into aperture 1120 of the lock leg sub-assembly 1020 so that working portion 1102 nests within fork 1306 and spherical protrusions 1316, 1318 are opposite short spring 1600. The clamp/lock selector sub-assembly may then be assembled around the lock leg sub-assembly 1020 and the pivot leg sub-assembly 1030. Ball detent 1080 may be inserted into hole 1410 and the short protrusion 1418 may be positioned between the arm 1062 and the rest of the lock leg 1100 so that tip portion extends into alcove 1214, ball detent engages groove 1122, and the tall protrusion 1412 is opposite the arm 1062. Second protrusion 1518 may be similarly positioned on a contralateral side of the lock leg 1100. Fastener 1802 may be inserted through hole 1514 and into hole 1414, and fastener 1804 may be inserted through hole 1516 and into hole 1416 to secure the selector back plate 1500 to the selector body 1400.

Figures 28A, 28B:
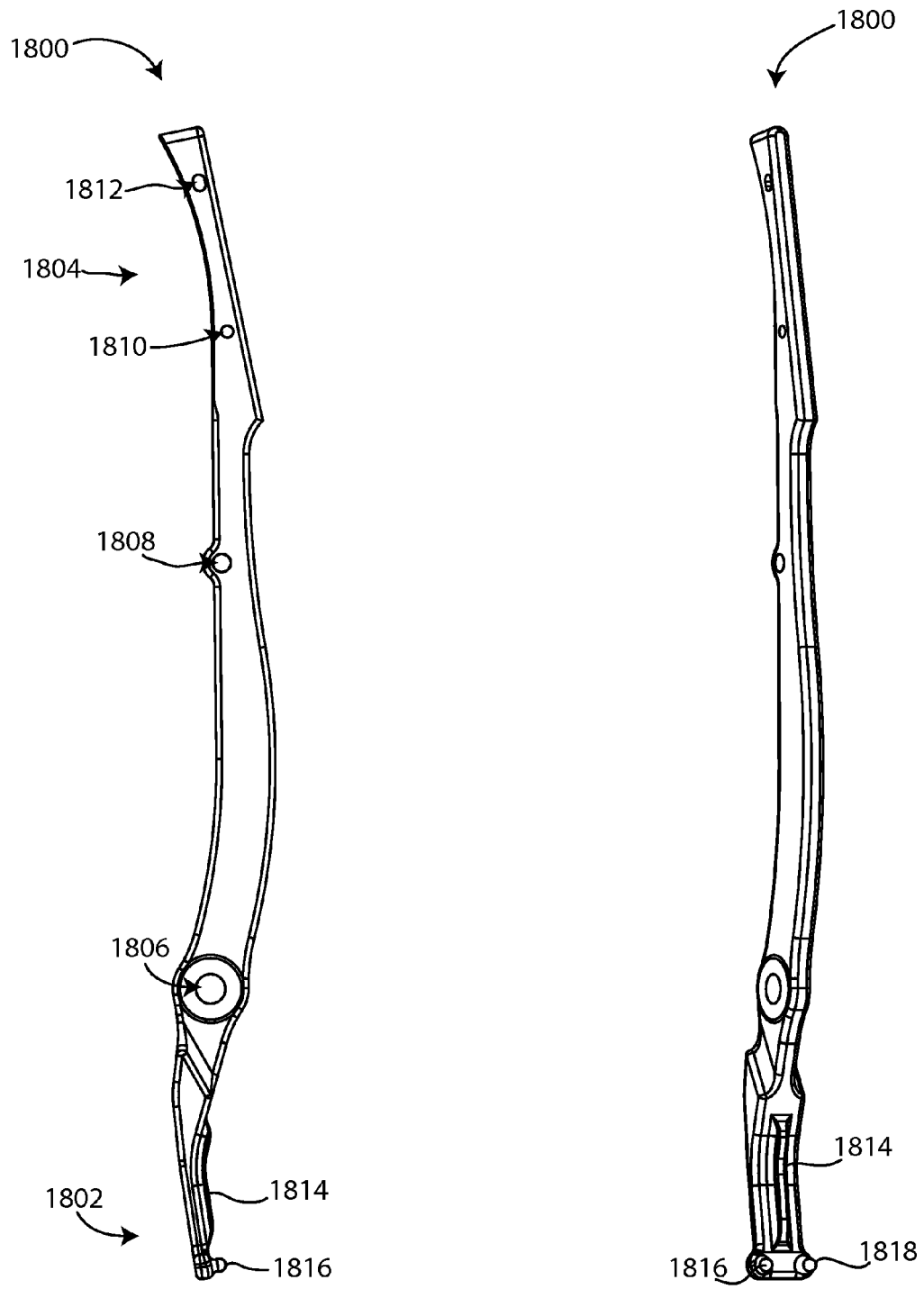
FIG. 28A is a front view of the rigid leg of FIG. 22.
FIG. 28B is a perspective view of the rigid leg of FIG. 28A.

Referring to FIGS. 28A-B, the rigid leg 1800 may be an elongated member with a working portion 1802, a grip portion 1804 opposite the working portion, first and second holes 1806, 1808 between the working portion and the grip portion, and third and fourth holes 1810, 1812 in the grip portion. The rigid leg 1800 may resemble first leg 352. The working portion 1802 may also be described as a jaw. The grip portion 1804 may also be described as a handle portion. The working portion 1802 may be thicker than the grip portion 1804, at least in a direction parallel to the holes 1806, 1808, 1810, 1812. The working portion 1802 may also include a rib 1814 centrally located in the thickness. The working portion 1802 may also include one or more spherical protrusions 1816. For example, two spherical protrusions 1816, 1818 are positioned near a free end of the working portion 1802 on the same side as the rib 1814 and extending generally perpendicular to a center longitudinal axis of hole 1806. In this example, a line or axis through the spherical centers of the protrusions 1816, 1818 is parallel to the axis of hole 1806, although other orientations are contemplated. The rigid leg 1800 may include a blind hole 1820 in a side opposite the spherical protrusions, as may be seen best in FIG. 32. Hole 1820 may be proximate hole 1808.

Figure 29A:
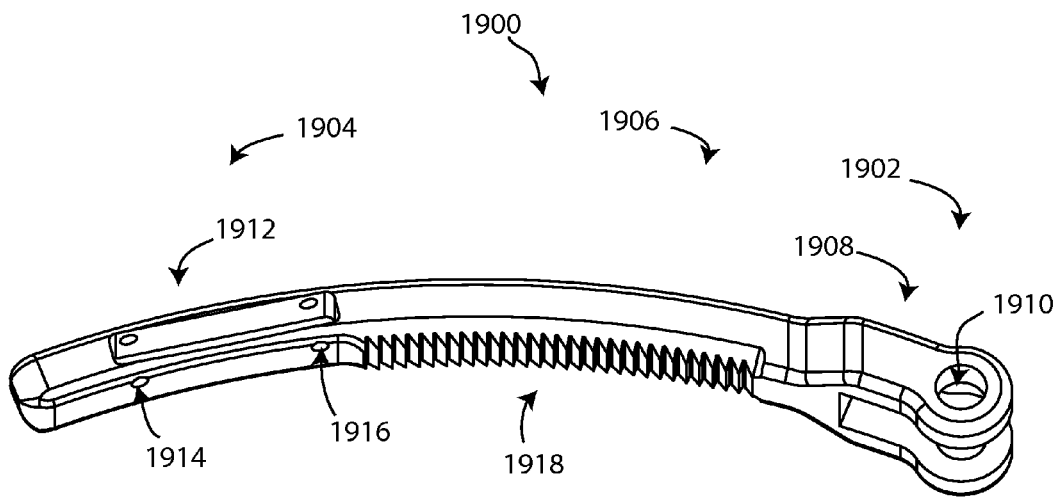
FIG. 29A is a perspective view of the ratchet arm of FIG. 22.
Figure 29B:
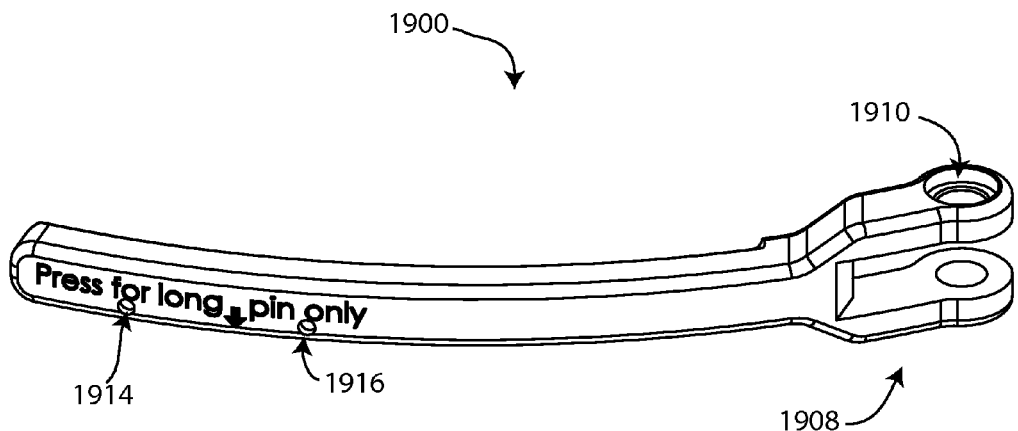
FIG. 29B is another perspective view of the ratchet arm of FIG. 29A from a different angle.

Referring to FIGS. 29A-B, the ratchet arm 1900 may be an elongated member with a first portion 1902, a second portion 1904, and a middle portion 1906. The ratchet arm 1900 may share some or all of the characteristics of ratchet arm 372. The first portion 1902 may form a clevis 1908, which may also be described as a bifurcation or fork. A hole 1910 may extend through the ratchet arm 1900 and across the clevis 1908. The second portion 1904 may include a pocket 1912. First and second holes 1914, 1916 may extend through the ratchet arm and across the pocket 1912. The middle portion 1906 may include a plurality of serrations 1918 on a side adjacent to the pocket 1912.

Figure 30A:
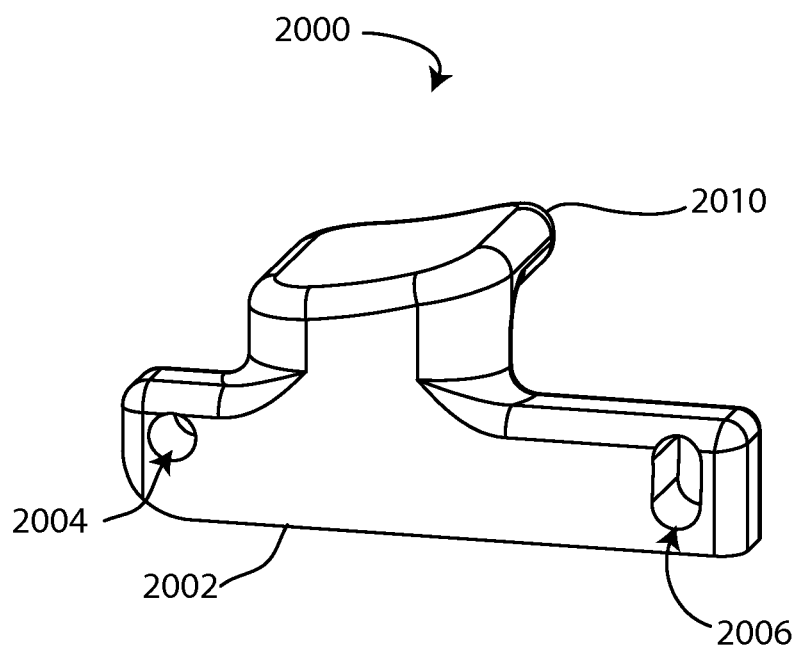
FIG. 30A is a perspective view of the button of FIG. 22.
Figure 30B:
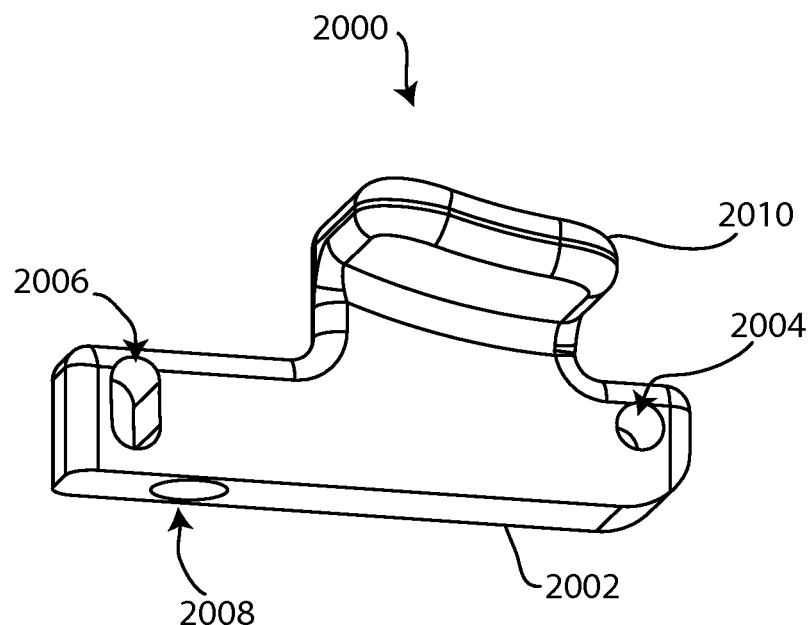
FIG. 30B is another perspective view of the button of FIG. 30A from a different angle.

Referring to FIGS. 30A-B, the button 2000 may include a generally rectangular rail 2002. A hole 2004 may extend through a first end of the rail 2002 and a slot 2006 may extend through a second end opposite the first end. The rail 2002 may include a second hole 2008 in a side adjacent to the hole 2004 and slot 2006. In this example, the hole 2008 is a blind hole between the hole 2004 and the slot 2006, closer to the slot 2006. The button 2000 may also include a tab 2010 which extends from a side of the rail 2002 opposite the blind hole 2008. The tab 2010 may provide an enlarged surface for contact with a portion of a user's hand, such as a fingertip.

The long spring 2100 may share some of the characteristics of the short spring 1600. The long spring 2100 may be an elongated ribbon-like member with a first portion 2102 and a second portion 2104. The long spring 2100 may include a through hole 2106 located between the first and second portions 2102, 2104. A hook 2108 may be included on a free end of the first portion 2102. A slot 2110 may be included proximate a free end of the second portion 2104. An enlargement 2112 may be included on the free end of the second portion 2104, at least in a direction transverse to the length of the long spring 2100 and a center longitudinal axis of the hole 2106. Note that the long spring 2100 is shown in its free state, i.e., undeflected, throughout this application. One of skill in the art will appreciate that the long spring 2100 will deflect to adapt to the constraints imposed by neighboring components.

The grip 2200 may have a channel 2202 formed in an elongated side of the grip and first and second holes 2204, 2206 which extend through the grip and intersect the channel. A second side 2208 of the grip 2200 opposite the channel 2200 may be broad and gently rounded to present a comfortable surface for contact by a portion of a user's hand. One or more finger rests 2210 may be formed on the grip 2200. The grip 2200 may be at least partially formed of a resilient material to increase user comfort, although stiff materials may also be used.

The rigid leg sub-assembly 1040 may be assembled by inserting fastener 1094 through hole 2106 and into hole 1820 to secure long spring 2100 to the rigid leg 1800 so that hook 2108 is proximate hole 1808 and facing away from hole 1808. Long spring 2100 may be pre-curved during fabrication or bent during assembly so that hook 2108 and enlargement 2112 curve away from rigid leg 1800. The portion of rigid leg 1800 surrounding hole 1810 may then be inserted into clevis 1908 so that hook 2108 faces into the bottom of the clevis, and fastener 1088 may be inserted through holes 1910, 1810 to secure the ratchet arm 1900 to the rigid arm 1800. The spring 1086 may be inserted into hole 2008 and the rail 2002 may be inserted into the pocket 1912. Fastener 1090 may be inserted through holes 1914, 2004 and fastener 1092 may be inserted through hole 1916 and slot 2006 to secure button 2000 to ratchet arm 1900. When the button is assembled to the ratchet arm 1900, the spring 1086 biases the button to protrude from the pocket 1912. More specifically, in this example, the second end of the rail 2002, which includes slot 2006, is biased to protrude from the pocket 1912. The grip 2200 may be assembled to the rigid leg 1800 by sliding the grip portion 1804 into the channel 2202, inserting the fastener 1096 in holes 2206, 1812, and inserting the fastener 1098 in holes 2204, 1810. In an alternate assembly method, the rigid leg sub-assembly 1040 during final assembly of the primary instrument 1000.

The primary instrument 1000 may be assembled by extending the rigid leg sub-assembly through aperture 1222 so that the spherical protrusions 1816, 1818 face the spherical protrusions 1316, 1318, the holes 1106, 1206, 1806 are concentric, and the ratchet bar 1900 extends through the aperture. Fastener 1070 may be inserted into holes 1106, 1206, 1806 to secure the lock/pivot leg sub-assembly 1010 and the rigid leg assembly 1040 together. Tab 1610 may be inserted into slot 2110 to couple the short spring 1600 to the long spring 2100.

Primary instrument 2400 may embody certain characteristics. For example, the force indicator 1060 is an integral cantilever beam feature. As another example, the lock leg 1100, pivot leg 1200, and rigid leg 1800 are centrally arranged. As yet another example, pivot leg sub-assembly 1030 permits free rotation of pivot head 1300 relative to pivot leg 1200. As yet another example, the clamp/lock selector sub-assembly 1050 slides between first and second positions along the lock/pivot leg sub-assembly 1010.

Figure 31:
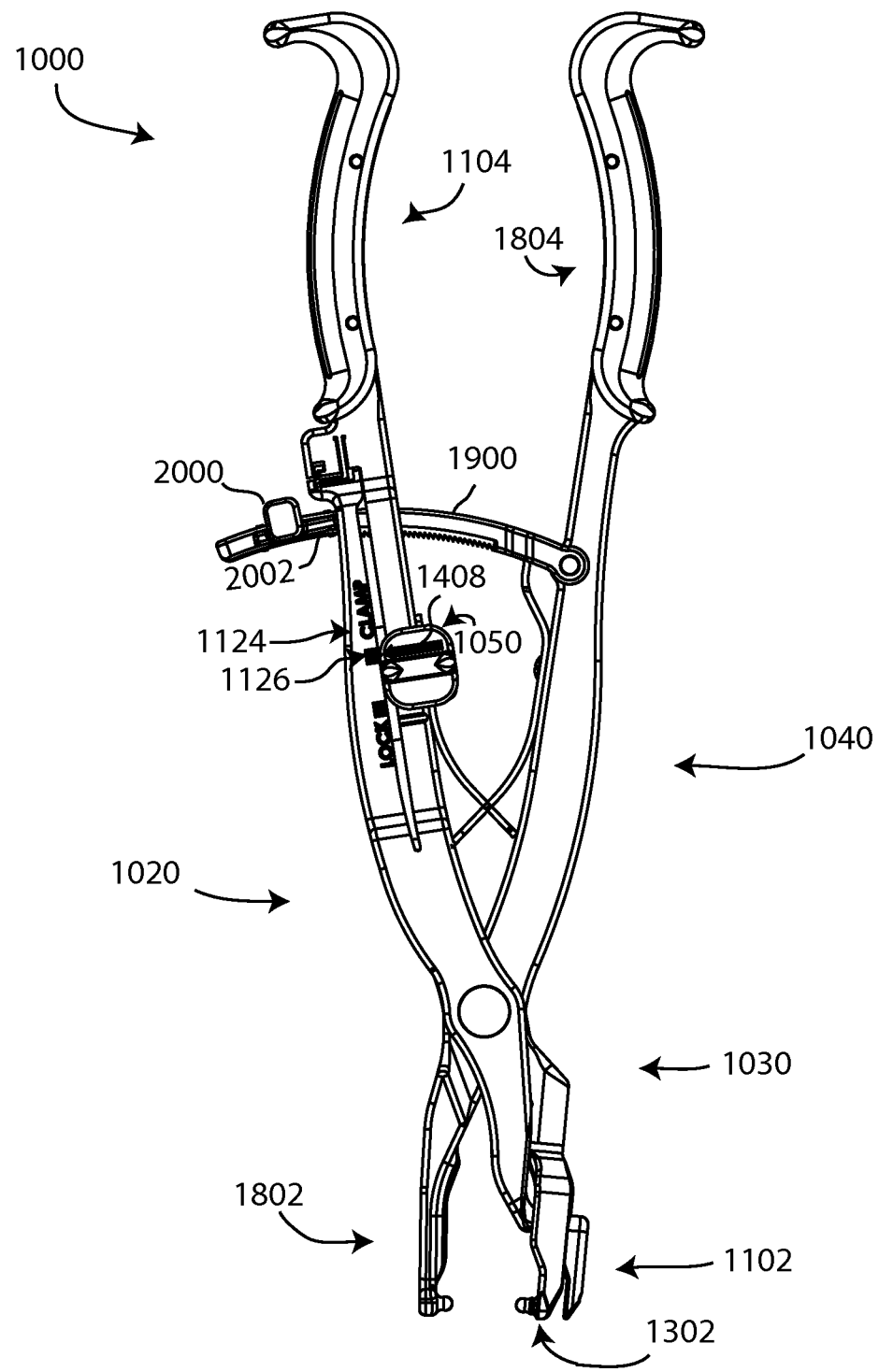
FIG. 31 is a front view of the primary instrument of FIG. 19 in a configuration in which the lock and rigid legs are open, the selector is in a clamping position, and the ratchet arm is disengaged from the pivot leg.

Referring to FIG. 31, the primary instrument 1000 is shown in a configuration in which the rigid leg grip portion 1804 is spaced apart from the lock leg grip portion 1104, the ratchet arm 1900 is spaced apart from the tooth 1212, and the selector 1050 is in a first position. It can also be appreciated that the rigid leg jaw 1802 is spaced apart from the pivot jaw 1302 in this configuration, and that the rigid leg jaw 1802 is spaced even farther apart from the lock jaw 1102. By spacing the ratchet arm 1900 apart from the tooth 1212, the grip portions 1804, 1104 may be moved apart without hindrance, at least until the second end of the rail 2002 touches the arm 1062. By depressing the button 2000, the grip portions 1804, 1104 may be moved even farther apart, as might be necessary to accommodate an implant with a long post. By positioning the selector 1050 in the first position, the lock leg sub-assembly 1020 is fixed to the pivot leg sub-assembly 1030 so that they pivot as one relative to the rigid leg sub-assembly 1040. With brief reference to FIG. 33B, it can be appreciated that tip portion 1420 is in narrow portion 1218, thus fixing the lock leg 1100 to the pivot leg 1200. FIG. 33B is a cross section view along a plane parallel to the center plane of the primary instrument 1000 and offset to pass through the selector. More specifically, the cross section plane passes through alcove 1214, as may be appreciated in FIG. 24B. The first position of the selector 1050 may be indicated by indicia 1126 aligned with the arrow 1408. The first position of the selector 1050 may also be described as the "CLAMP" position, according to the text 1124 proximate the arrow 1408. This configuration of the primary instrument 1000 may facilitate coupling the primary instrument to an implant, otherwise known as picking an implant up.

Figure 32:
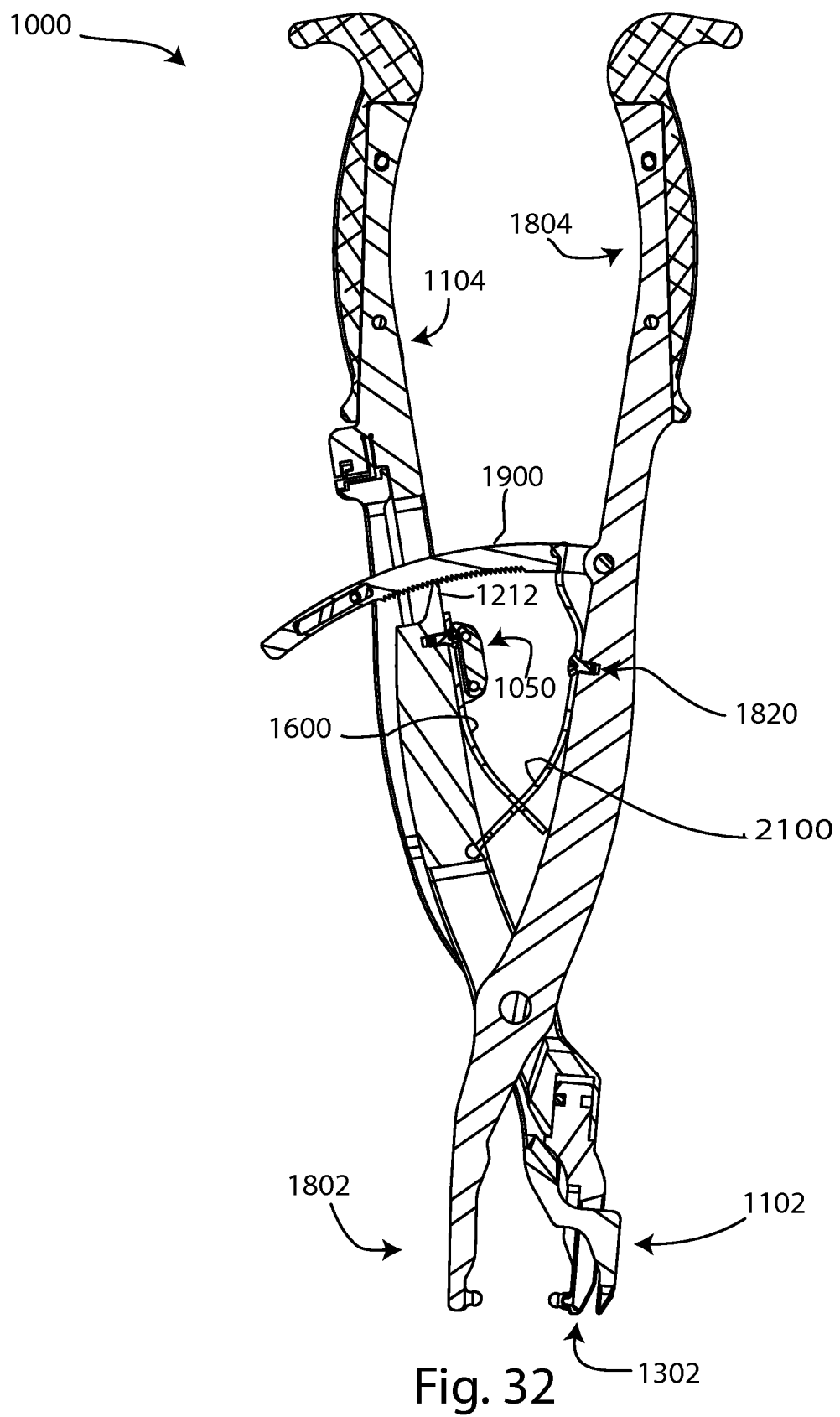
FIG. 32 is a front cross sectional view of the primary instrument of FIG. 19 in a configuration in which the ratchet arm is engaged with the pivot leg, taken along a center plane of the primary instrument.

Referring to FIG. 32, a central cross section of the primary instrument 1000 is shown in a configuration in which the rigid leg grip portion 1804 is spaced apart from the lock leg grip portion 1104, the ratchet arm 1900 is engaged with the tooth 1212, and the selector 1050 is in a first position. By engaging the ratchet arm 1900 with the tooth 1212, the grip portions 1804, 1104 may be moved closer together without hindrance, but may not be moved apart unless the ratchet arm 1900 is disengaged from the tooth 1212. This configuration of the primary instrument 1000 may also facilitate picking up an implant, or inserting the implant into an implantation site.

Figure 33A:
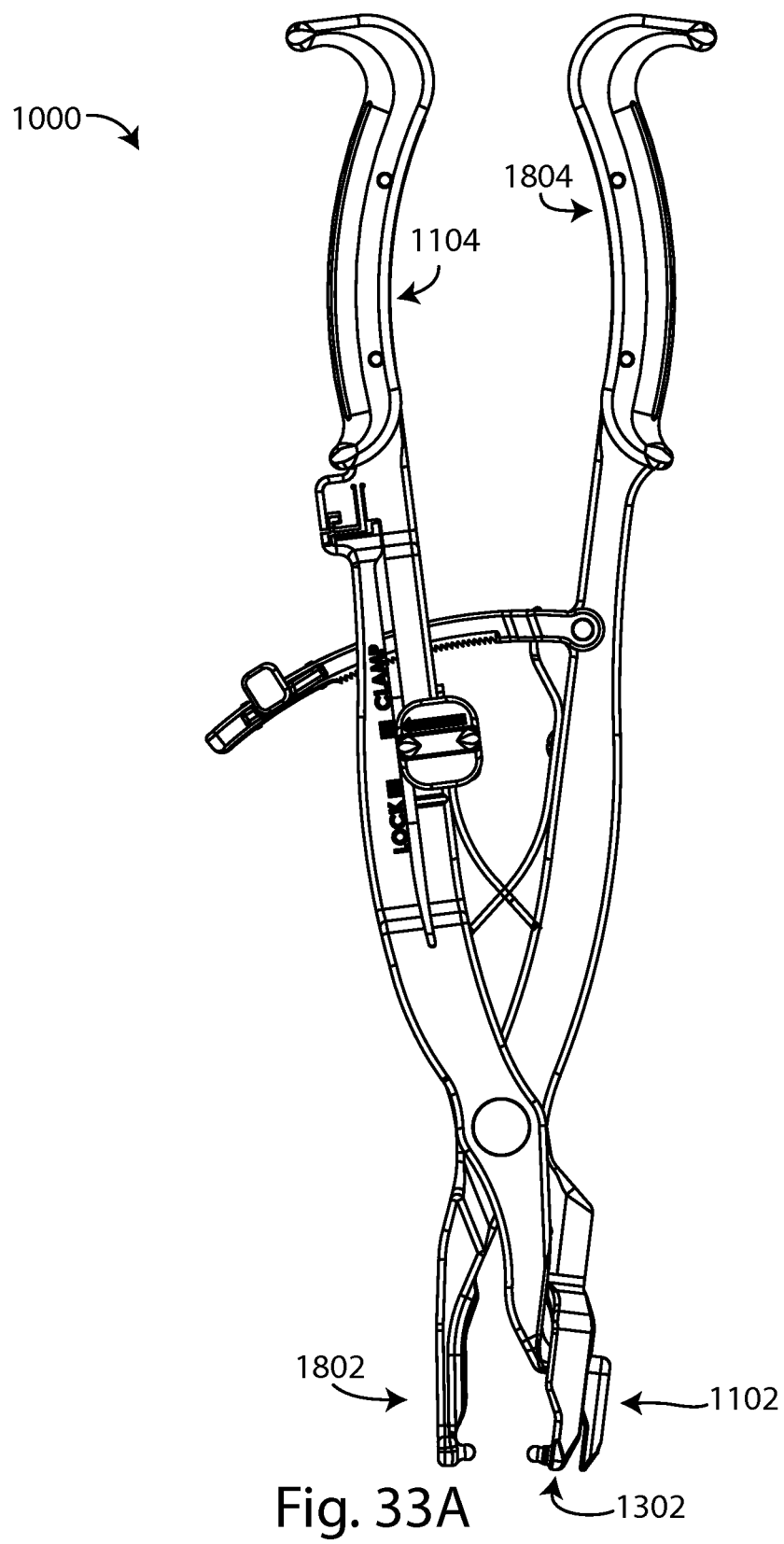
FIG. 33A is a front view of the primary instrument of FIG. 19 in a configuration in which the lock and rigid legs are partially closed.
Figure 33B:
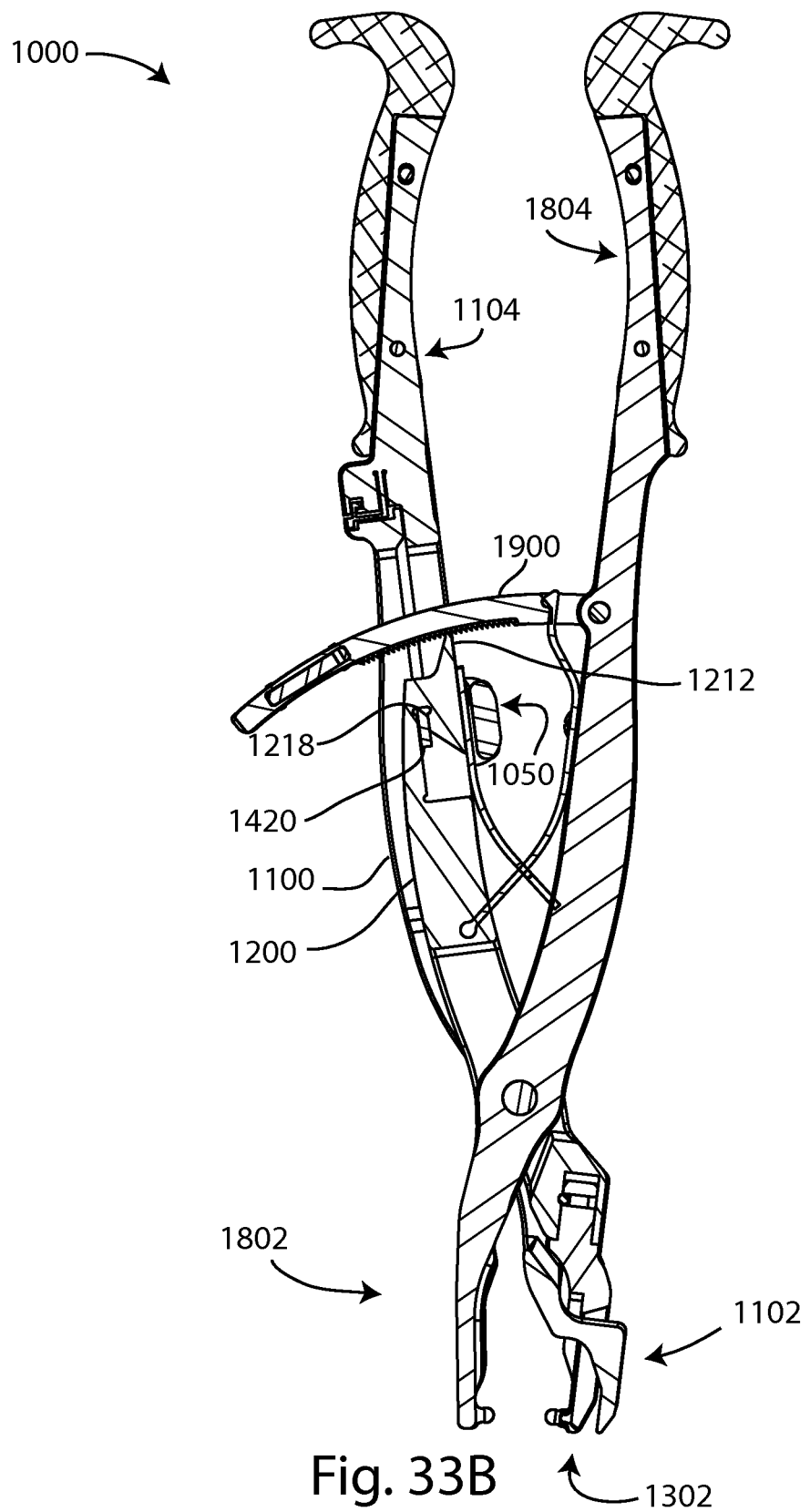
FIG. 33B is a front cross section view of the primary instrument of FIG. 33A, taken along a plane parallel to the center plane and passing through the selector.

Referring to FIGS. 33A-B, the primary instrument 1000 is shown in a configuration in which the rigid leg grip portion 1804 is closer to the lock leg grip portion 1104. It can also be appreciated that the rigid leg jaw 1802 is closer to the pivot jaw 1302 in this configuration, but the distance between the lock jaw 1102 and the pivot jaw 1302 remains fixed. This configuration may be described as a clamped configuration or a compressed configuration.

Figure 34:
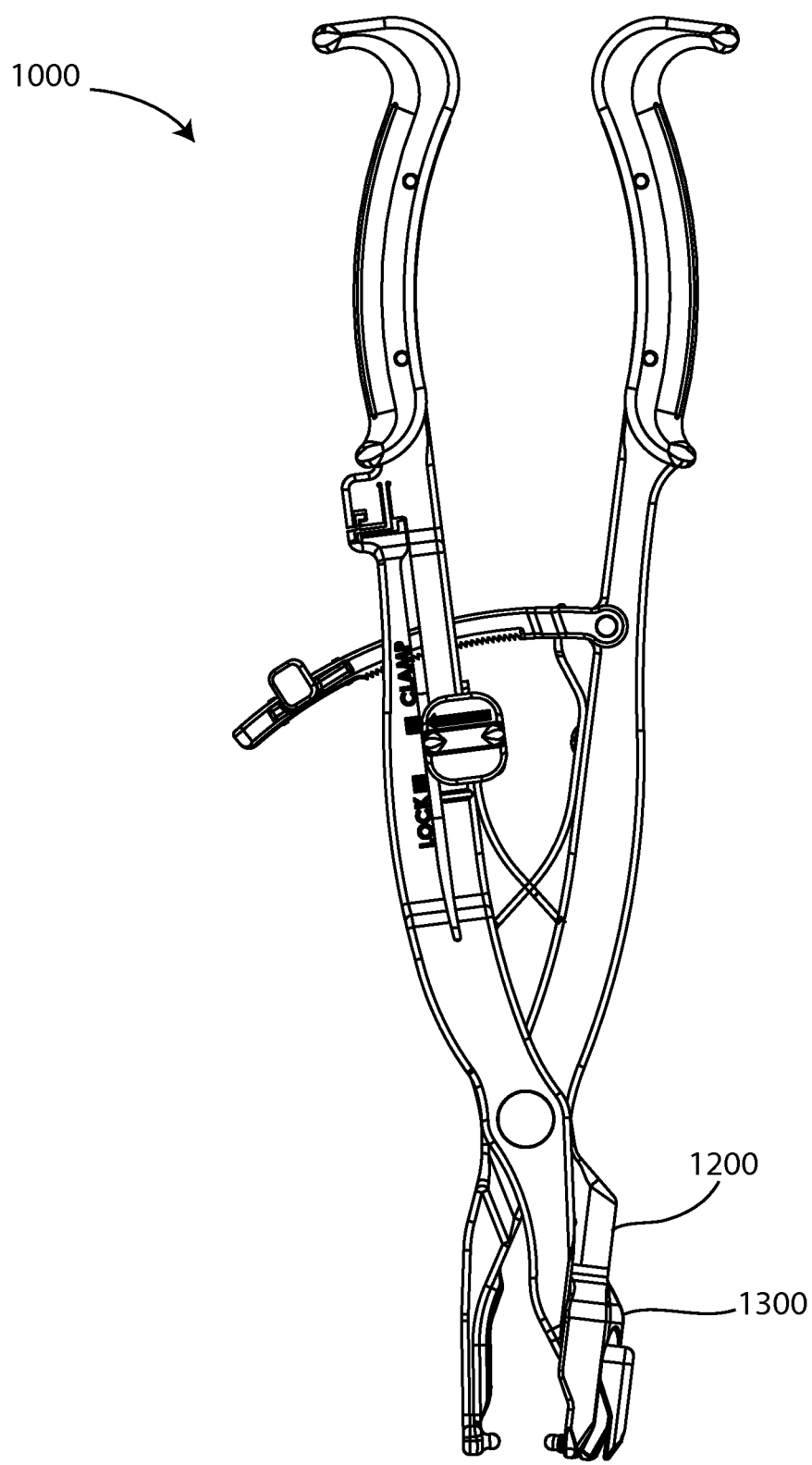
FIG. 34 is a front view of the primary instrument of FIG. 19 in a configuration in which the pivot head is rotated out of alignment with the pivot leg.

Referring to FIG. 34, the primary instrument 1000 is still shown in a clamped configuration. However, the pivot head 1300 is shown rotated out of alignment with the pivot leg 1200. In this example, the shaft 1320 has rotated about the center longitudinal axis of hole 1210.

Figure 35A:
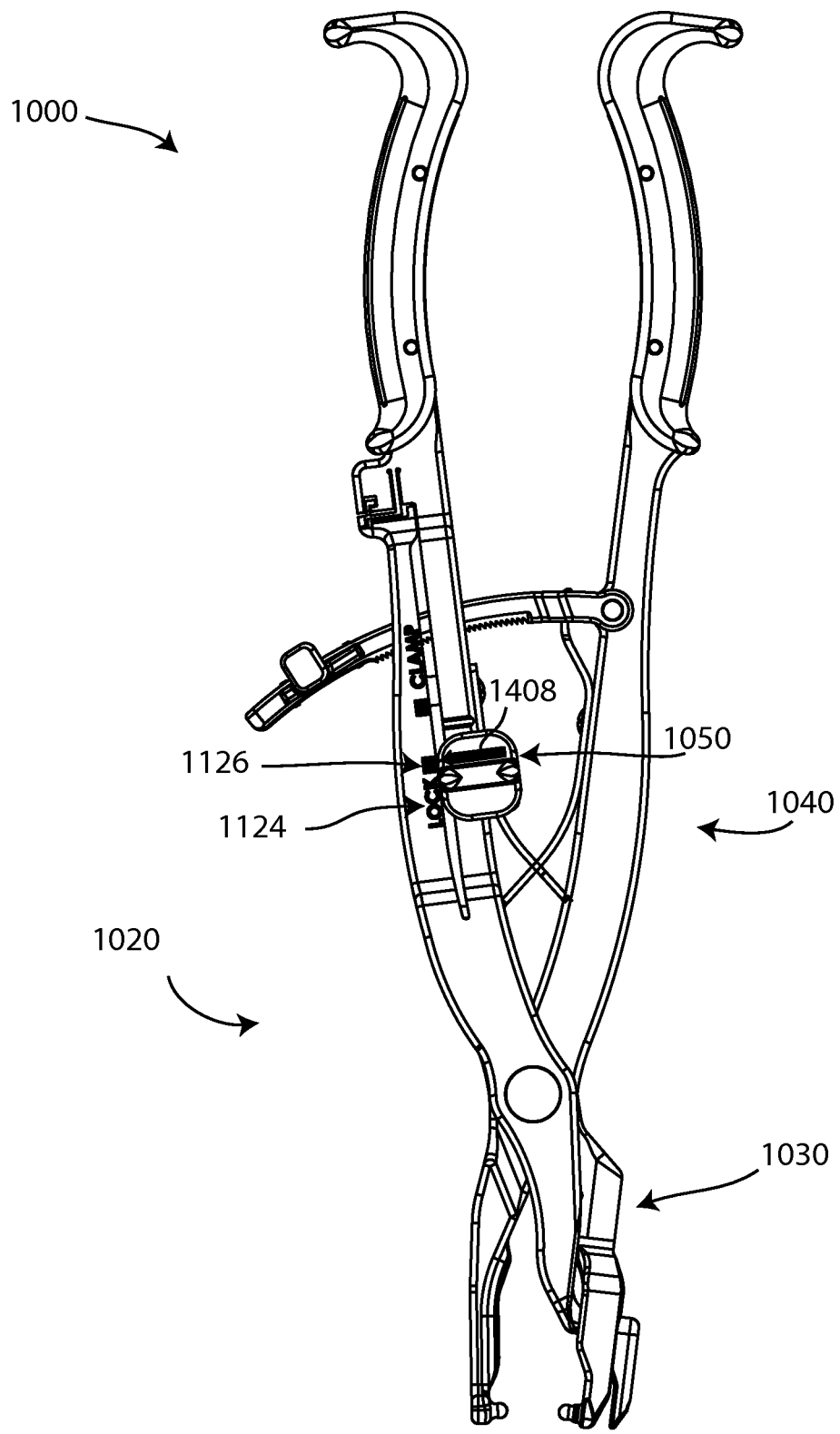
FIG. 35A is a front view of the primary instrument of FIG. 19 in a configuration in which the pivot head is realigned with the pivot leg and the selector is in a locking position.
Figure 35B:
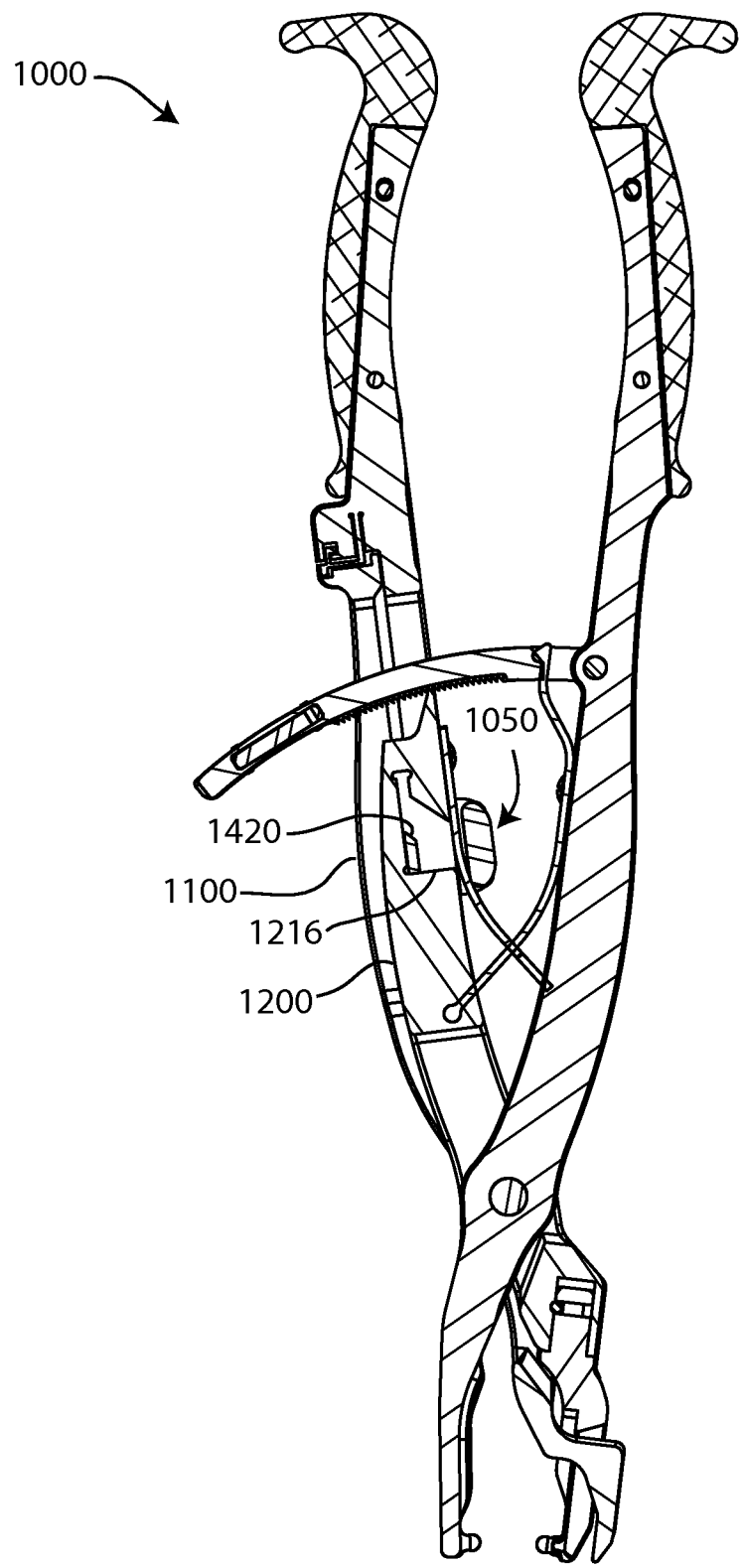
FIG. 35B is a front cross section view of the primary instrument of FIG. 35A, taken along a plane parallel to the center plane and passing through the selector.

Referring to FIGS. 35A-B, the primary instrument 1000 is still shown in a clamped configuration. However, the selector 1050 is shown in a second position. By positioning the selector 1050 in the second position, the lock leg sub-assembly 1020 is disengaged from the pivot leg sub-assembly 1030 so that each may pivot independently relative to the rigid leg sub-assembly 1040. With brief reference to FIG. 35B, it can be appreciated that tip portion 1420 is in wide portion 1216, thus permitting the lock leg 1100 to pivot about fastener 1070 toward rigid leg 1800 independently of the pivot leg 1200. Indeed, since the ratchet arm 1900 is still engaged with the tooth 1212 in this configuration, relative rotation of the pivot leg 1200 and the rigid leg 1800 is prevented by the engagement of the hook 2108 with the serrations 1918 of the ratchet bar 1900. The second position of the selector 1050 may be indicated by indicia 1126 aligned with the arrow 1408. The second position of the selector 1050 may also be described as the "LOCK" position, according to the text 1124 proximate the arrow 1408. This configuration of the primary instrument 1000 may facilitate locking an implant.

Figure 37:
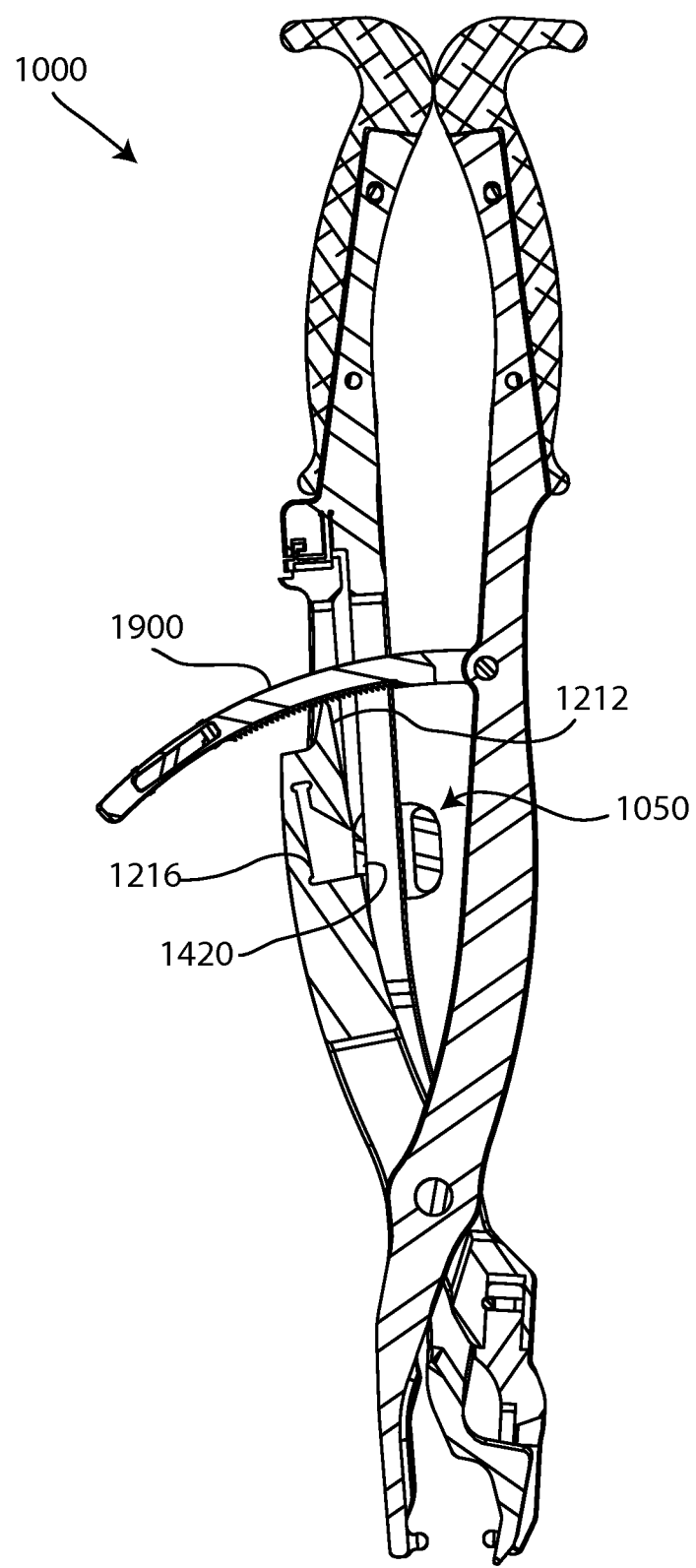
FIG. 37 is a front cross section view of the primary instrument of FIG. 36A, taken along a plane parallel to the center plane and passing through the selector.

Referring to FIGS. 36A-37, the primary instrument 1000 is shown in a configuration in which the rigid leg grip portion 1804 is very close to the lock leg grip portion 1104, the ratchet arm 1900 is still engaged with the tooth 1212, and the selector 1050 is still in the second position. It can be appreciated that tip portion 1420 is proximate the region where the wide portion 1216 breaks through the side wall of the pivot leg 1200. It can also be appreciated that the lock leg 1100 has pivoted about fastener 1070 toward rigid leg 1800 independently of the pivot leg 1200. It can also be appreciated that the distance between the rigid leg jaw 1802 and the pivot jaw 1302 is unchanged relative to FIGS. 35A-B, and that the distance between the rigid leg jaw 1802 and the lock jaw 1102 has decreased. In this configuration, the force indicator 1060 is shown in its deployed state after indicating that a predetermined force has been applied to lock an implant. This example of a force indicator relies upon cantilever beam deflection of the lock leg 1100 to trigger the force indicator. With reference to FIGS. 23A-B and 36A-B, it can be appreciated that the lock leg 1100 may deflect toward the rigid leg

1800 as increasing force is applied across the handle portions 1804, 1104 and resisted by an implant between the jaws 1802, 1102. However, arm 1062 may not deflect appreciably because it is separated from the rest of the lock leg 1100. Therefore, at a predetermined force, the lock leg 1100 may deflect enough to permit the strike portion 1066 to snap over the strike portion 1067, producing an audible and/or tactile indication that the predetermined force has been achieved. The restraint portions 1068, 1069 may interact with each other to limit the lateral protrusion of arm 1062. It can be appreciated that, as the force across the grip portions 1804, 1104 is released, the strike portions 1066, 1067 may snap back over each other to automatically return the force indicator 1060 to its free state. This configuration of the primary instrument 1000 may correspond to a locked implant.

Referring to FIGS. 38-41, a third example of a primary instrument 2400 is illustrated. Primary instrument 2400 may be used to provide insertion, compression and locking of spinal implant 100 or other related embodiments, and may resemble first instrument 350 and/or primary instrument 1000. Primary instrument 2400 may include a lock/pivot leg sub-assembly 2410, a rigid leg sub-assembly 2440, a clamp/lock selector sub-assembly 2450, a force indicator 2460, and a main pivot fastener 2470.

Figure 38:
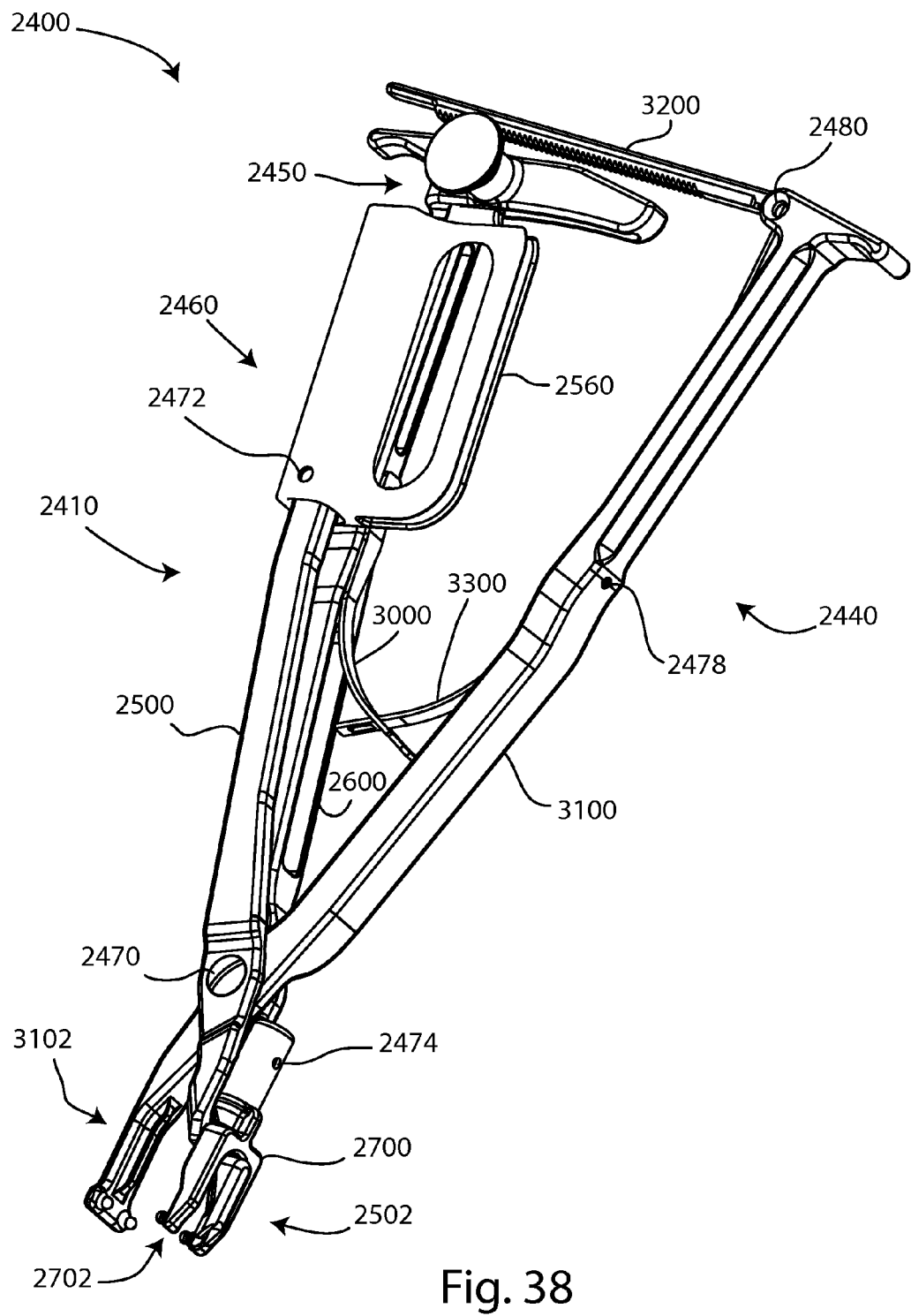
FIG. 38 is a perspective view of a third example of a primary instrument.
Figure 39:
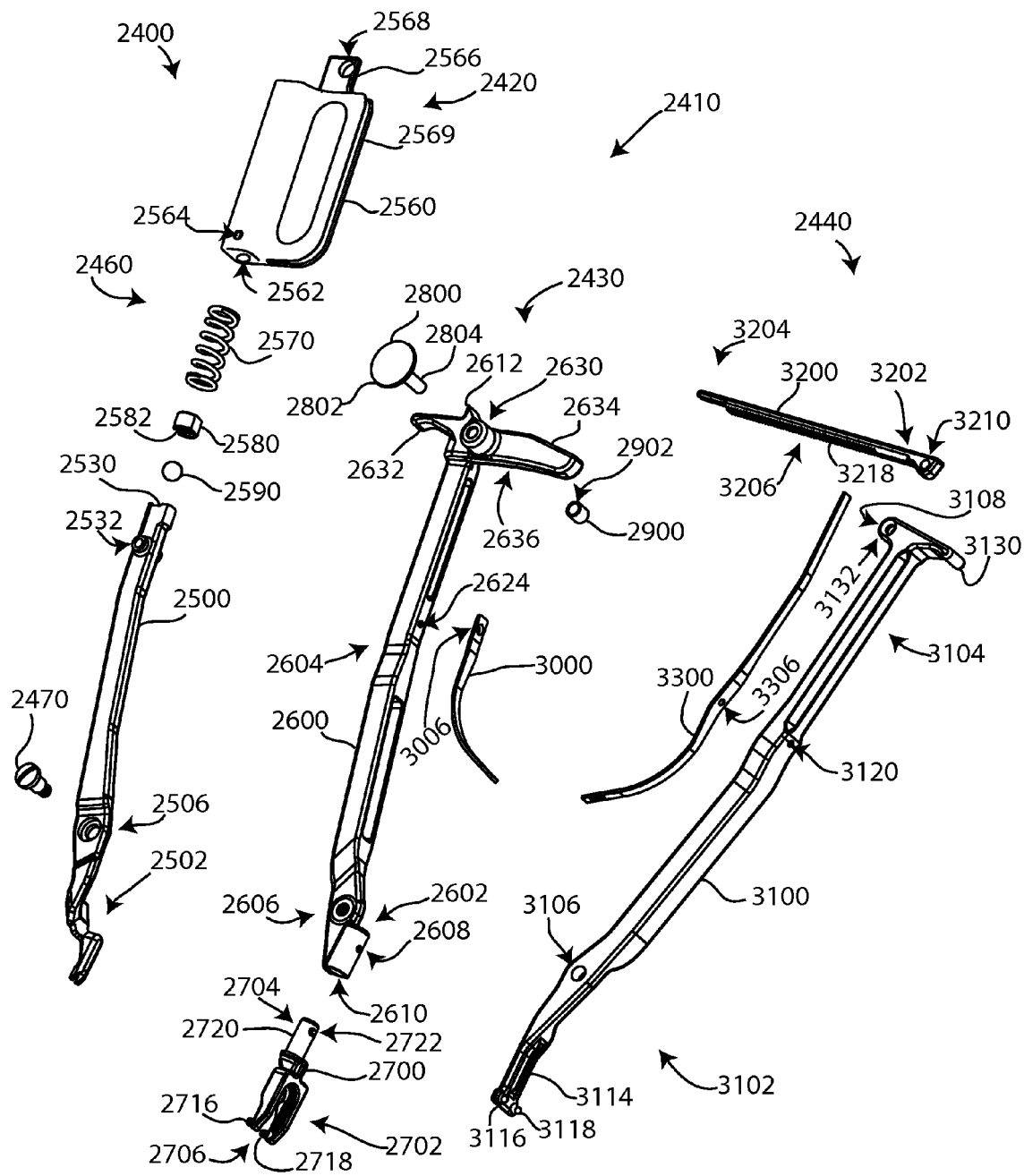
FIG. 39 is an exploded perspective view of the primary instrument of FIG. 38, illustrating a lock leg, a ball, a spring end adaptor, a spring, a housing, a pivot leg, a pivot head, a selector pin, a selector sleeve, a short spring, a rigid leg, a ratchet arm, a long spring, and a main pivot fastener.
Figure 40:
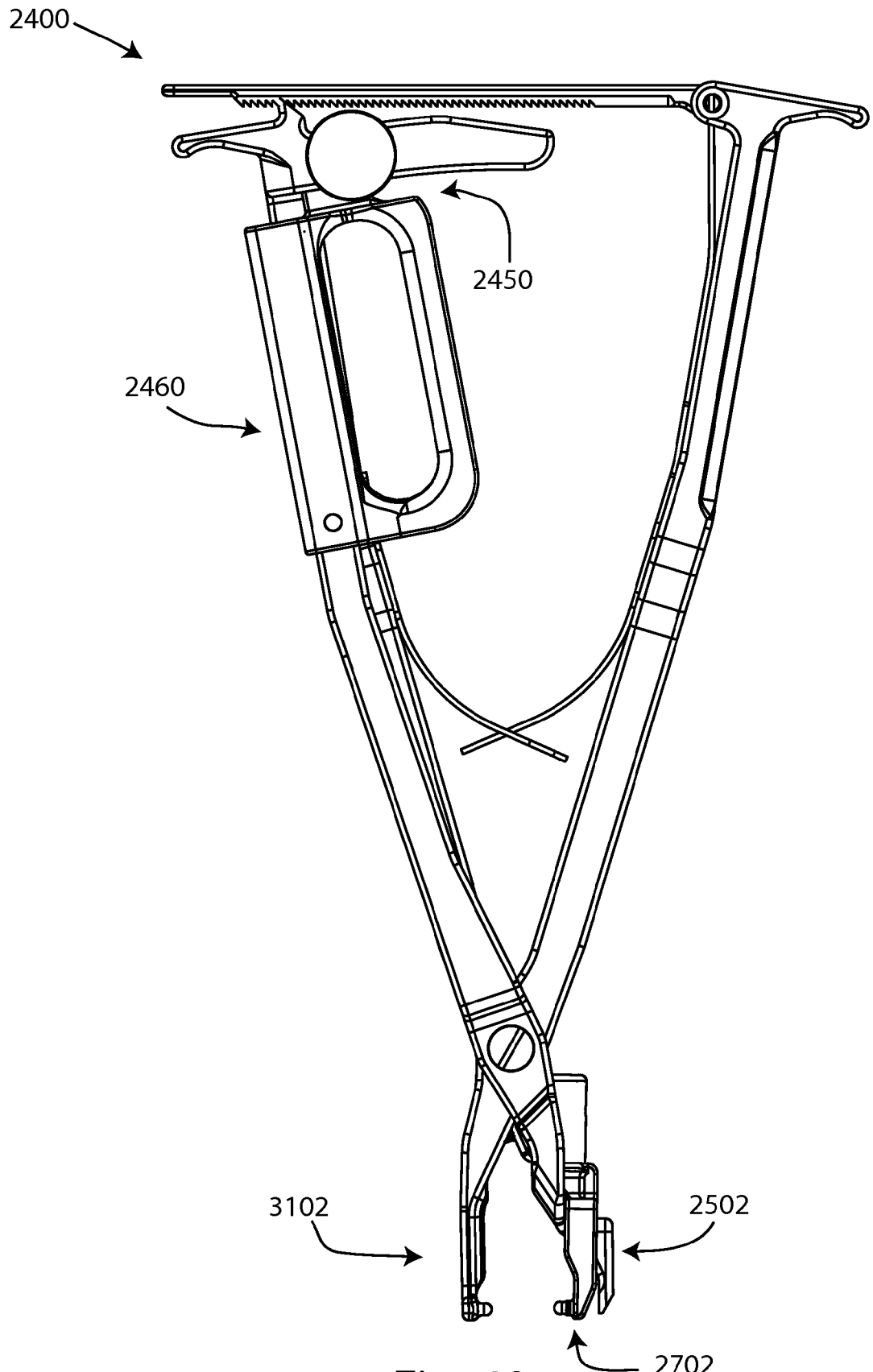
FIG. 40 is a front view of the primary instrument of FIG. 38 in a configuration in which the lock and rigid legs are open, the selector is in a clamping position, and the ratchet arm is engaged with the pivot leg.
Figure 41A:
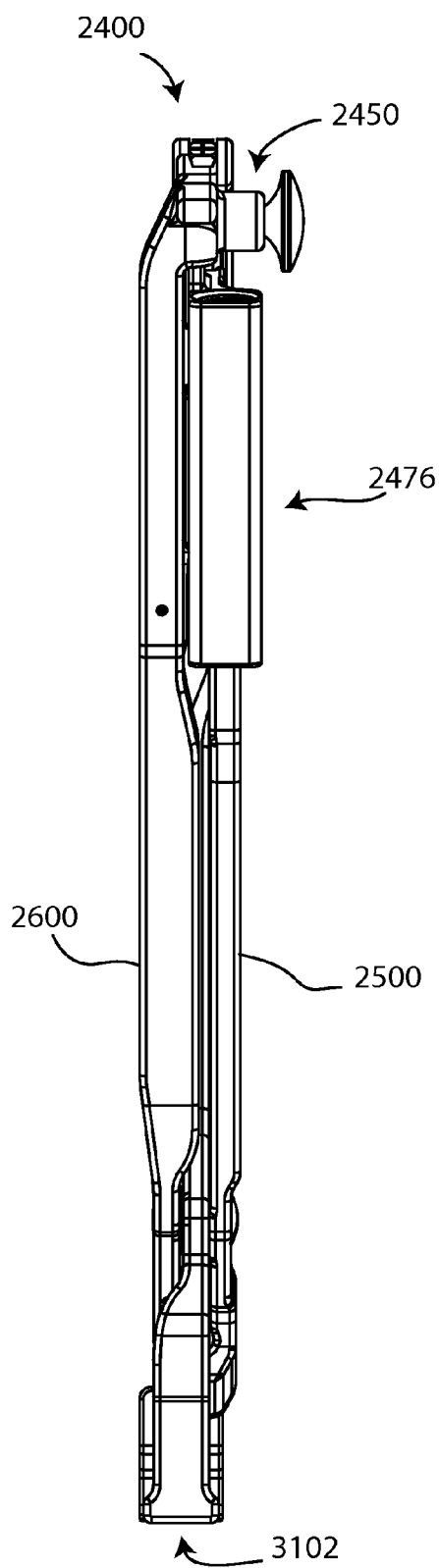
FIG. 41A is a left side view of the primary instrument of FIG. 38.
Figure 41B:
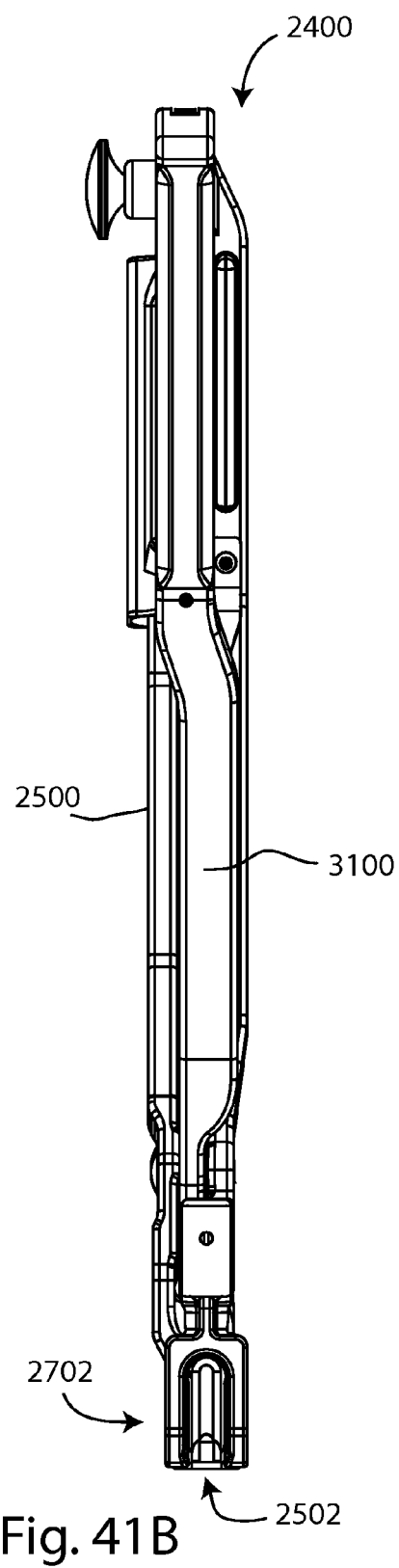
FIG. 41B is a right side view of the primary instrument of FIG. 40A.

Referring to FIGS. 38-39, the lock/pivot leg sub-assembly 2410 may include a lock leg sub-assembly 2420, a pivot leg sub-assembly 2430, the clamp/lock selector sub-assembly 2450, and the force indicator 2460.

The lock leg sub-assembly 2420 may include a lock leg 2500, the force indicator 2460, and fastener 2472 to secure the force indicator to the lock leg.

The force indicator 2460 may be a sub-assembly which includes a housing 2560, a spring 2570, a spring end adaptor 2580, and a ball 2590.

The pivot leg sub-assembly 2430 may include a pivot leg 2600, a pivot head 2700, a short spring 3000, fastener 2474 to secure the pivot head to the pivot leg, and fastener 2476 to secure the short spring to the pivot leg.

The clamp/lock selector sub-assembly 2450 may include a selector body 2800 and a selector sleeve 2900.

Referring to FIGS. 38-39, the rigid leg sub-assembly 2440 may include a rigid leg 3100, a ratchet arm 3200, a long spring 3300, fastener 2478 to secure the long spring to the rigid leg, and fastener 2480 to secure the ratchet arm to the rigid leg.

The lock leg 2500 may be an elongated member with a working portion 2502, a rear portion 2504 opposite the working portion, and a first hole 2506 between the working portion and the grip portion. The working portion 2502 may be offset to one side in this example. The rear portion 2504 may terminate in a groove 2530. A through hole 2532 may be proximate the groove and parallel to hole 2506. Hole 2532 may be for fastener 2472.

The housing 2560 may include a blind hole 2562 for spring 2570, a cross hole 2564 for fastener 2472, a tab 2566 extending opposite the hole 2562, a cross hole 2568 through the tab, and a finger loop 2569. The spring end adapter 2580 may rest between an end of the spring 2570 and the ball 2590, and may modify the interaction between the spring and ball, compared to no adapter. A groove 2582 may be included on a ball-facing side of the adapter 2580. The ball 2590 may rest in the groove 2530. Fastener may be inserted through holes 2564, 2532 to couple the force indicator 2460 to the lock leg 2500. The spring 2570 may be compressed, or preloaded, in the lock leg sub-assembly 2420 so that the force indicator 2460 remains rigidly coupled to the lock leg 2500 until a predetermined force is applied by the primary instrument 2400 to lock an implant. The predetermined force may overcome the preload, causing the force indicator 2460 to abruptly shift toward the rigid leg 3100, producing an audible and/or tactile indication that the predetermined force has been achieved. The force indicator 2460 may manually or automatically reset as the force on the primary instrument is released.

The pivot leg 2600 may be an elongated member with a working portion 2602, a rear portion 2604 opposite the working portion, and a first hole 2606 between the working portion and the rear portion. The pivot leg 2600 may share some or all of the characteristics of third leg 356. The pivot leg 2600 may be offset to one side in this example. The working portion 2602 may include a second hole 2608 and a third hole 2610. Holes 2606, 2608, and 2610 may be mutually perpendicular. The rear portion 2604 may terminate in a tooth 2612. The rear portion 2604 may also include a hole 2630 adjacent to the tooth 2612, a finger rest 2632 protruding to one side proximate the hole 2630, and a projection 2634 extending on an opposite side from the finger rest 2632. The projection 2634 may include a slot 2636 or aperture extending generally parallel to hole 2610.

The pivot head 2700 may be a forked member with a working portion 2702 and a shaft portion 2704. The working portion 2702 may include a fork 2706. The working portion 2702 may also include one or more spherical protrusions 2716. This example has a second spherical protrusion 2718. The shaft portion 2704 may include a shaft 2720. A hole 2722 may be present on the shaft 1320. Hole may be non-circular or elongated to provide clearance with fastener 2474.

The selector body 2800 may also be described as a knob, pin, or spring plunger. The selector body 2800 may include a head 2802 and a shaft 2804 extending from the head. The selector sleeve 2900 may include a hole 2902 to receive a portion of the shaft 2804.

The pivot leg sub-assembly may be assembled by inserting shaft 2720 into hole 2610 and inserting fastener 2474 through hole 2608 and into hole 2722. Fastener 2476 may be inserted through hole 3006 in the short spring 3000 and into hole 2624 of pivot leg 2600 to secure the short spring to the pivot leg.

The lock/pivot leg sub-assembly 2410 may be assembled by placing the lock leg sub-assembly 2420 and the pivot leg sub-assembly 2430 side by side so that the lock jaw 2502 nests within the fork 2706 of the pivot jaw 2702 and the tab 2566 is in the slot 2636. The shaft 2804 may be inserted through holes 2630, 2568 and coupled with selector sleeve 2900.

The rigid leg 3100 may be an elongated member with a working portion 3102, a grip portion 3104 opposite the working portion, first hole 3106 between the working portion and the grip portion, and second hole 3108 proximate a free end of the grip portion 3104. At least a portion of the rigid leg 3100 may be offset to one side in this example. The working portion 1802 may include a central rib 3114 and a spherical protrusion 3116. This example also has a second spherical protrusion 3118. The grip portion 3104 may form a clevis 3132 incorporating the hole 3108. A finger rest 3130 may extend from the grip portion 3104 adjacent to the hole 3108.

The ratchet arm 3200 may be an elongated member with a first portion 3202, a second portion 3204, and a middle portion 3206. The ratchet arm 3200 may share some or all of the characteristics of ratchet arm 372. The first portion 3202 may include a through hole 3210. The middle portion 3206 may include a plurality of serrations 3218 on one side of the ratchet arm 3200.

The rigid leg sub-assembly 2440 may be assembled by inserting fastener 2478 through holes 3306, 3120 to secure long spring 3300 to rigid leg 3100 so that at least a portion of long spring 3300 rests in clevis 3132. The first portion 3202 may be inserted into clevis 3132 and fastener 2480 may be inserted through holes 3210, 3108 to secure ratchet arm 3200 to rigid leg 3100.

The primary instrument 2400 may be assembled by extending the rigid leg sub-assembly 2440 between the lock leg 2500 and the pivot leg 2600 so that the spherical protrusions 3116, 3118 face the spherical protrusions 2716, 2718, the holes 2506, 2606, 3106 are concentric, and the ratchet bar 3200 extends toward the tooth 2612. Fastener 2470 may be inserted into holes 2506, 2606, 3106 to secure the lock/pivot leg sub-assembly 2410 and the rigid leg assembly 2440 together. The short spring 1600 may be coupled to the long spring 2100.

Primary instrument 2400 may differ from first instrument 350 and/or primary instrument 1000 in certain regards. For example, the force indicator 2460 is a spring-loaded breakaway mechanism. As another example, the lock leg 2500, pivot leg 2600, and rigid leg 3100 are arranged side by side with offsets in or near the working portions to centralize the jaws. As yet another example, pivot leg sub-assembly 2430 limits the rotation of pivot head 2700 relative to pivot leg 2600 through the interaction of fastener 2474 in hole 2722. As yet another example, clamp/lock selector sub-assembly 2450 is spring biased to remain in the first position unless the selector body 2800 is pulled to overcome the bias to move the clamp/lock selector sub-assembly 2450 to the second position.

Figure 42:
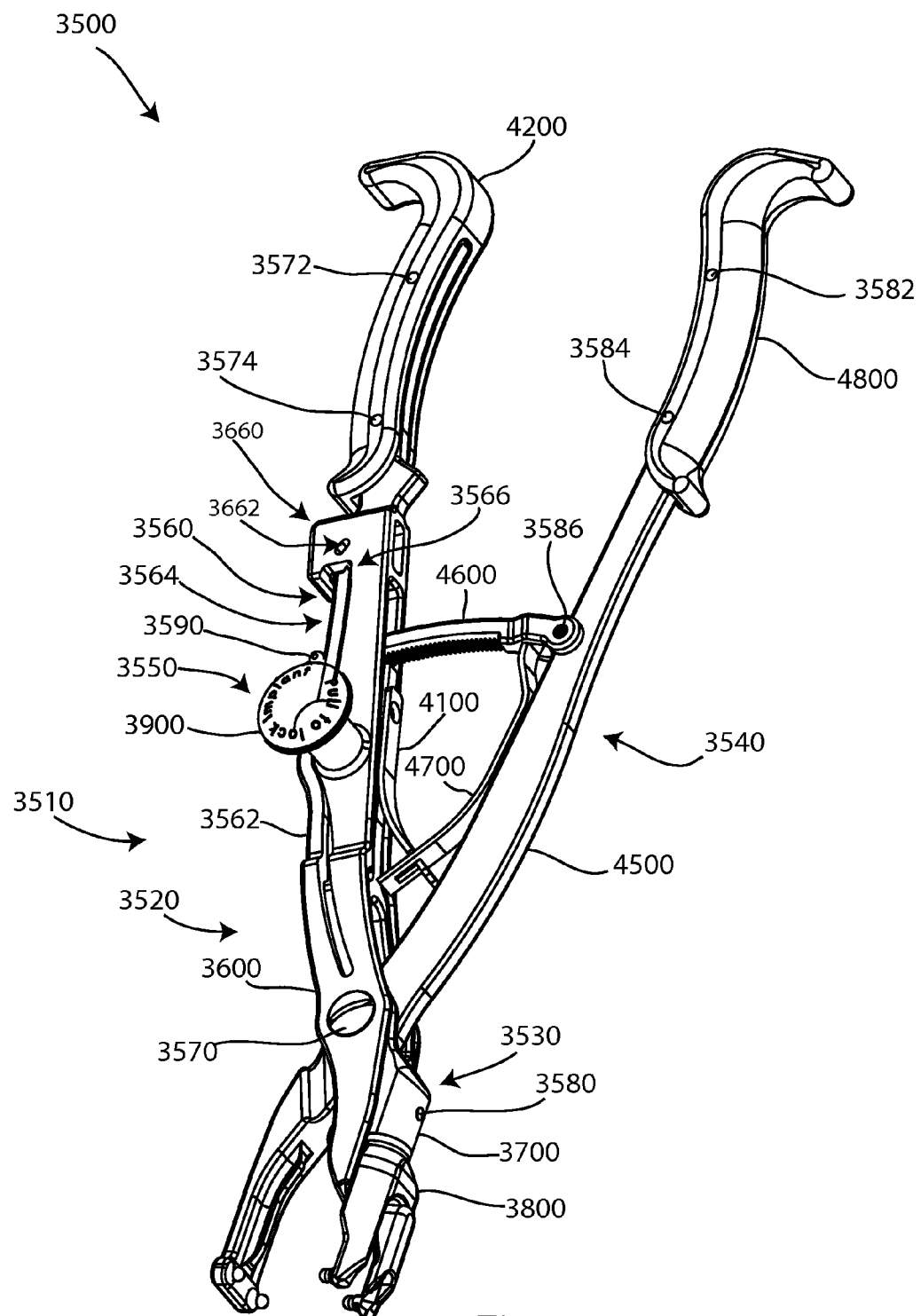
FIG. 42 is a perspective view of a fourth example of a primary instrument.
Figure 43A:
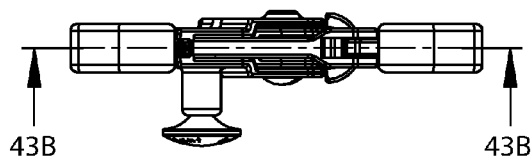
FIG. 43A is a top view of the primary instrument of FIG. 42.
Figure 43B:
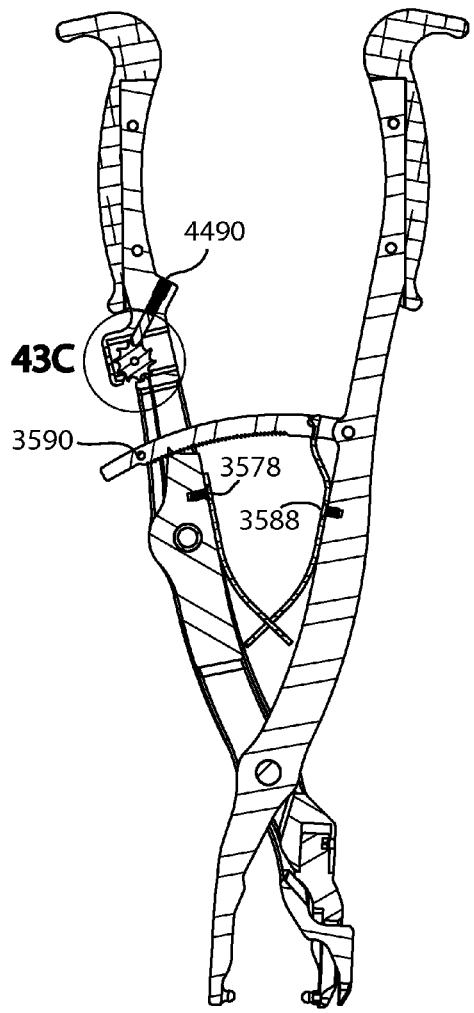
FIG. 43B is a front cross section view of the primary instrument of FIG. 43A, taken along a center plane of the primary instrument, as indicated by section line 43B-43B in FIG. 43A.
Figure 43C:
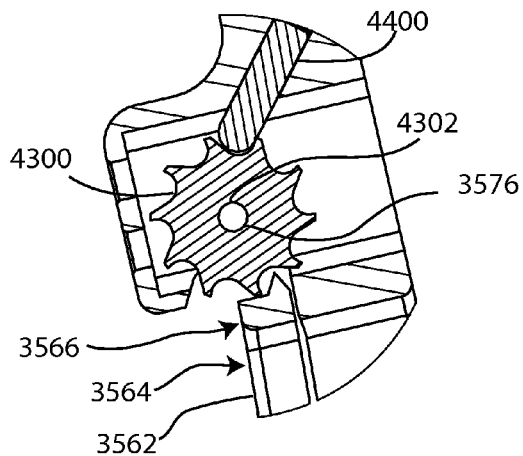
FIG. 43C is an enlarged detail cross section view of a portion of the primary instrument, as indicated by the circle 43C in FIG. 43B.

Referring to FIGS. 42-43C, a fourth example of a primary instrument 3500 is illustrated. Primary instrument 3500 may be used to provide insertion, compression and locking of spinal implant 100 or other related embodiments, and may resemble first instrument 350, primary instrument 1000, and/or primary instrument 2400. Primary instrument 3500 may include a lock/pivot leg sub-assembly 3510, a rigid leg sub-assembly 3540, a clamp/lock selector sub-assembly 3550, a force indicator 3560, and a main pivot fastener 3570.

The lock/pivot leg sub-assembly 3510 may include a lock leg sub-assembly 3520, a pivot leg sub-assembly 3530, the clamp/lock selector sub-assembly 3550, and the force indicator 3560. The lock leg sub-assembly 3520 may include a lock leg 3600, a grip 4200, the force indicator 3560, and fasteners 3572, 3574. The force indicator 3560 may be a sub-assembly which includes a housing 3660, a wheel 4300, a plunger 4400, a spring 4490, and a fastener 3576 to secure the force indicator to the lock leg. The pivot leg sub-assembly 3530 may include a pivot leg 3700, a pivot head 3800, a short spring 4100, and fasteners 3578, 3580. The clamp/lock selector sub-assembly 3550 may include a selector body 3900 and a selector sleeve 4000. The clamp/lock selector sub-assembly 3550 may resemble clamp/lock selector sub-assembly 2450.

The rigid leg sub-assembly 3540 may include a rigid leg 4500, a ratchet arm 4600, a long spring 4700, a grip 4800, and fasteners 3582, 3584, 3586, 3588, 3590.

The lock leg 3600 may include another example of an arm 3562 which is integrally formed as part of the lock leg. A free end of the arm 3562 may terminate in a tip portion 3564. The tip portion 3564 may terminate in a strike portion 3566 which may also be described as a tooth. The lock leg 3600 may also include the housing 3660, which may be adjacent to the strike portion 3566. A slot 3662 may extend through the housing 3660.

The wheel 4300 may resemble a star or pinwheel with a central hole 4302. The plunger 4400 may be a rod, such as a dowel pin. The spring 4490 may fit into the housing 3660, followed by the plunger 4400 and the wheel 4300. A fastener 3576 may be inserted through slot 3662 and hole 4302 to secure the force indicator 3560 to the lock leg. In this arrangement, the spring 4490 may press the plunger 4400 against the wheel 4300. The spring 4490 may be compressed, or preloaded, in the lock leg sub-assembly so that the force indicator 3560 remains rigidly coupled to the lock leg 3600 until a predetermined implant locking force is applied by the primary instrument 3500. The predetermined force may overcome the preload, causing the wheel 4300 to abruptly turn, producing an audible and/or tactile indication that the predetermined force has been achieved. In other words, the predetermined force may cause the lock leg 3600 to deflect, thus urging the housing 3660 and wheel 4300 across the strike portion 3566 against the resistance of the plunger 4400 and spring 4490. When the resistance is overcome, the wheel 4300 may abruptly turn. The force indicator 3560 may automatically reset as the force on the primary instrument 3500 is released. For example, the plunger 4400 may automatically press against the wheel 4300.

The pivot leg 2600 may include a hole 3714 to receive a portion of the selector body 2800. In other respects, the pivot leg 2600 may resemble the pivot leg 1200.

The ratchet arm 3200 may receive fastener 3590 in a free end of the ratchet arm. Fastener 3590 may serve as a fixed stop or limit when opening the primary instrument 3500, similar to the function of button 2000 with ratchet arm 1900.

Primary instrument 3500 may differ from first instrument 350, primary instrument 1000, and/or primary instrument 2400 in certain regards. For example, the force indicator 3560 is a spring-loaded pinwheel mechanism incorporating an arm 3562 which may be integrally formed with the lock leg 3600. The clamp/lock selector sub-assembly 3550 resembles the clamp/lock selector sub-assembly 2450, but is located between the ratchet arm 4600 and the main pivot 3570. The ratchet arm 4600 bears a fixed stop, fastener 3590, instead of a button 2000.

Figure 44:
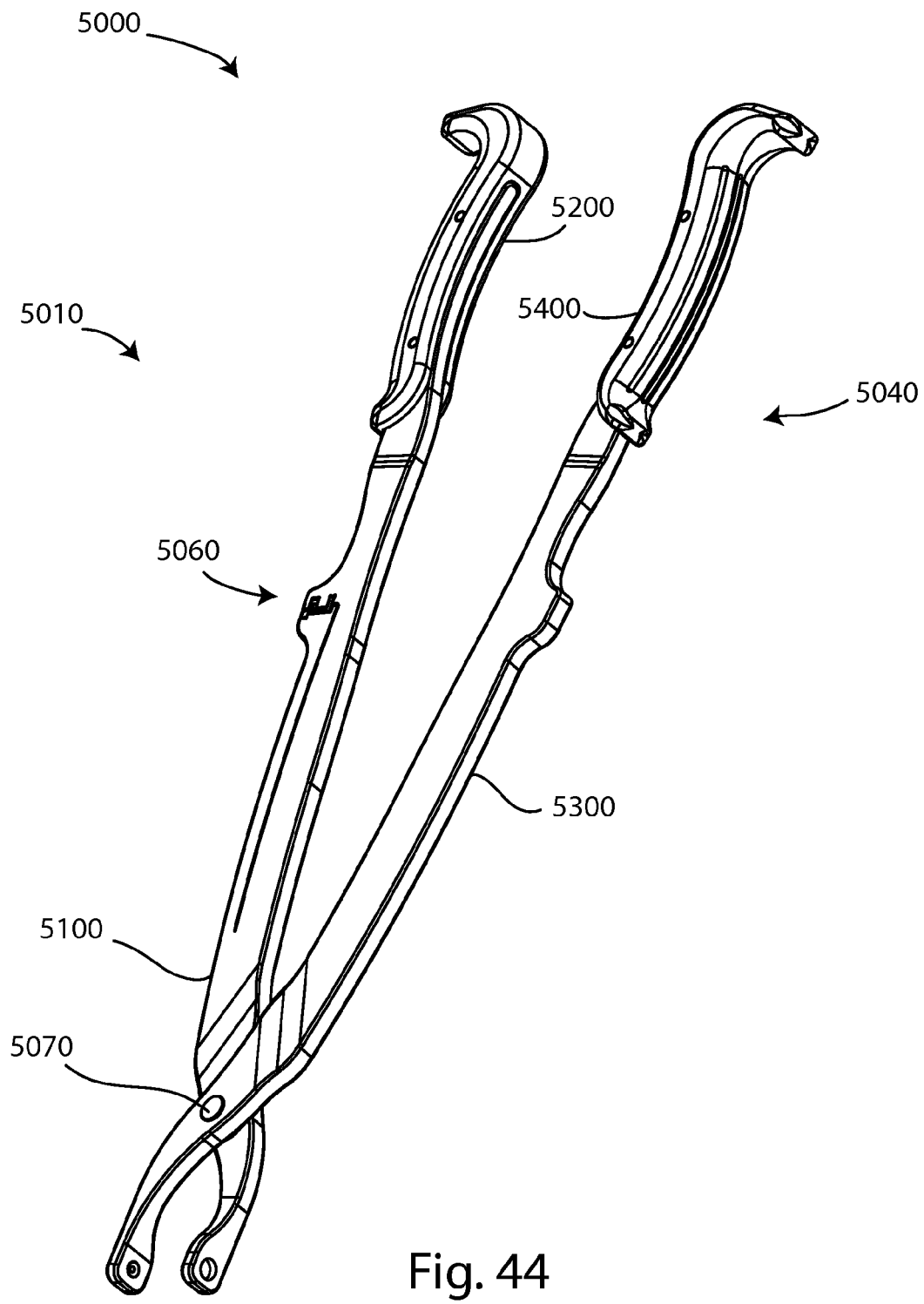
FIG. 44 is a perspective view of a second example of a secondary instrument.
Figures 45A, 45B:
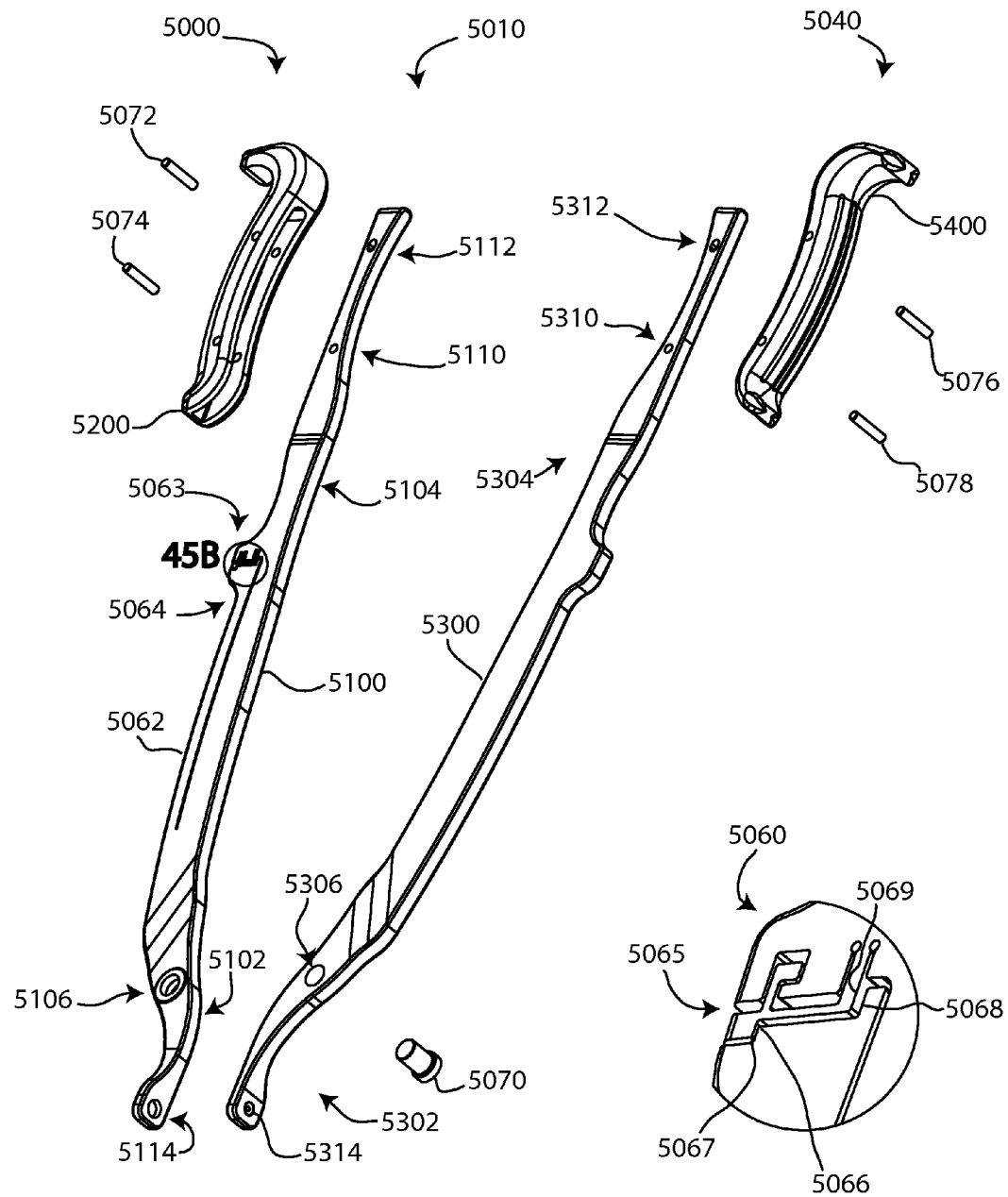
FIG. 45A is an exploded perspective view of the secondary instrument of FIG. 44, illustrating a force indicator leg, a rigid leg, a pair of grips, and a main pivot element.
FIG. 45B is an enlarged detail view of a portion of the force indicator leg, as indicated by the circle 45B in FIG. 45A.

Referring to FIGS. 44-45B, a second example of a secondary instrument 5000 is illustrated. Secondary instrument 500 may be used to provide locking of the locking mechanism 108 and may resemble second instrument 380. Secondary instrument 5000 may include a force indicator arm sub-assembly 5010, a rigid leg sub-assembly 5040, a force indicator 5060, and a main pivot fastener 5070.

The force indicator arm sub-assembly 5010 may include a force indicator leg 5100, a grip 5200, the force indicator 5060, and fasteners 5072, 5074.

The rigid leg sub-assembly may include a rigid leg 5300, a grip 5400, and fasteners 5076, 5078.

The force indicator leg 5100 may be an elongated member with a working portion 5102, a grip portion 5104 opposite the working portion, a first hole 5106 between the working portion and the grip portion, and second and third holes 5110, 5112 in the grip portion. The working portion 5102 may also be described as a jaw. The grip portion 5104 may also be described as a handle portion. The working portion 5102 may include a through hole 5114 proximate a free end of the working portion.

In this example, the force indicator leg 5100 includes an integrally formed force indicator 5060 similar to force indicator 1060, although other force indicators may be substituted. The force indicator 5060 may include at least one arm 5062 which protrudes from the lock leg 5100 and terminates in a tip portion 5064. The tip portion 5064 may include a strike portion 5066 and a restraint portion 5068. The force indicator 5060 may also include an enlargement 5063 which protrudes from the lock leg 5100 adjacent to the tip portion 5064. The enlargement 5063 may include a strike portion 5067 and a restraint portion 5069. The enlargement 5063 may also include a relief channel 5065 to increase the mobility of the strike portion 5067 and the restraint portion 5069. In this example, the force indicator 5060 may be formed by one or more wire electrical discharge machining (wire EDM) cuts through the lock leg 5100.

The grip 5200 may be similar or identical to the grip 1700, and may be assembled to the force indicator leg 5100 with fasteners 5072, 5074 in like manner to form the force indicator leg sub-assembly 5010.

The rigid leg 5300 may be an elongated member with a working portion 5302, a grip portion 5304 opposite the working portion, a first hole 5306 between the working portion and the grip portion, and second and third holes 5310, 5312 in the grip portion. The working portion 5302 may also be described as a jaw. The grip portion 5304 may also be described as a handle portion. The working portion 5302 may include a dimple 5314 or recess proximate a free end of the working portion.

The grip 5400 may be similar or identical to the grip 2200, and may be assembled to the rigid leg 5300 with fasteners 5076, 5078 in like manner to form the rigid leg sub-assembly 5040.

The secondary instrument 5000 may be assembled by placing the force indicator leg sub-assembly 5010 and the rigid leg sub-assembly 5040 side by side and crossing so that the dimple 5314 faces the hole 5114 and the holes 5106, 5306 are concentric. Fastener 5070 may be inserted through holes 5106, 5306 to secure the force indicator leg sub-assembly 5010 and the rigid leg sub-assembly 5040 together. When assembled, the secondary instrument 5000 opens and closes like a pair of pliers or scissors.

Figure 46:
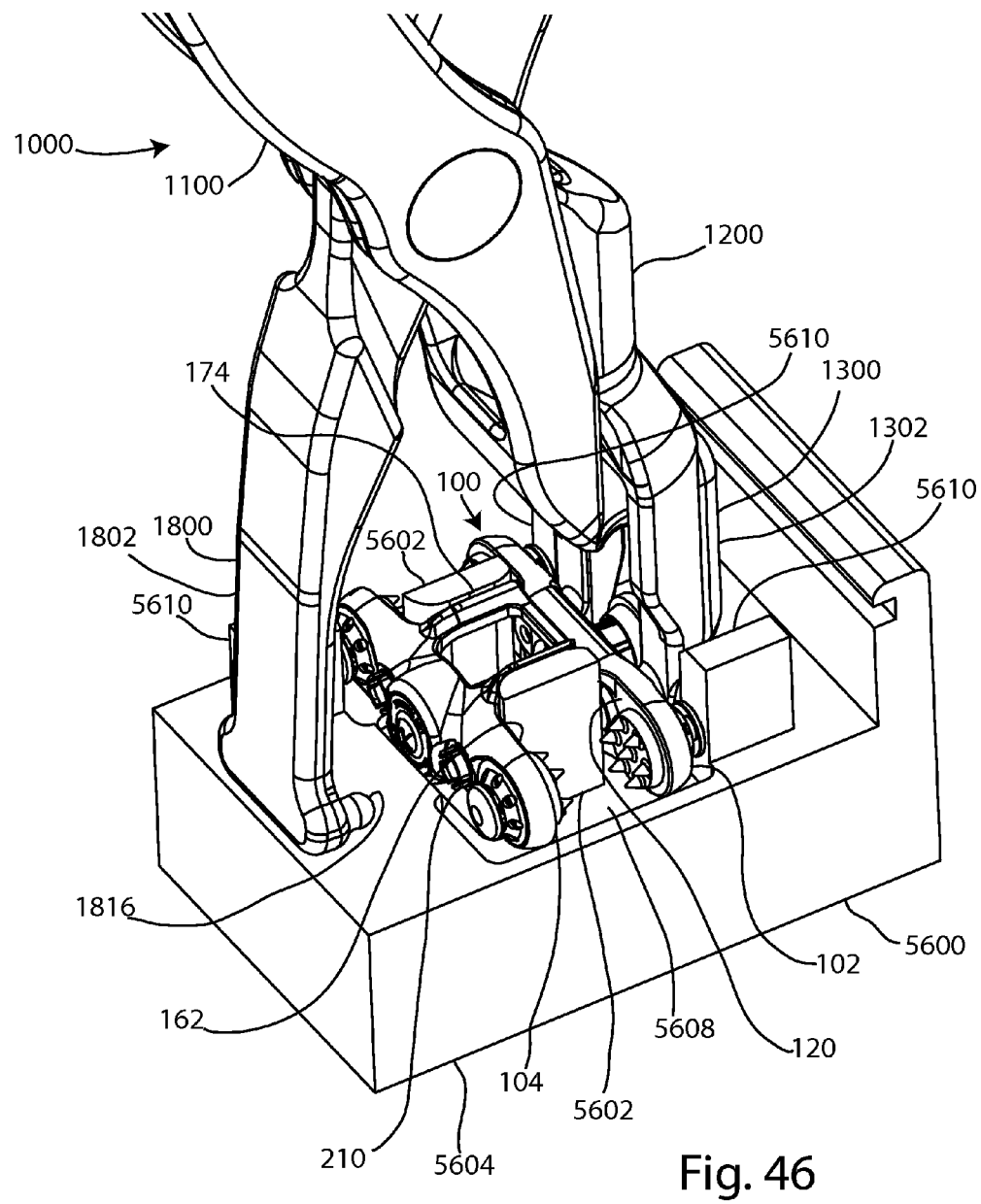
FIG. 46 is a perspective view of the primary instrument of FIG. 19 partially coupled to the spinal implant of FIG. 1, which is resting in a caddy.

Referring to FIG. 46, the implant is shown resting in a caddy 5600. The caddy 5600 may include one or more tabs 5602 projecting from a base 5604. In this example, the caddy 5600 includes two tabs 5602. The base 5604 may include a pocket 5608 surrounding the tabs 5602. One or more additional tabs 5610 may also extend from the base 5604 lateral to the tab 5602.

The implant 100, assembled as shown in FIG. 1, may rest in the caddy so that the tabs 5602 are between obverse sides 120, 162, the first and second walls 174, 176 are between the tabs, and the second wall 176 is adjacent to the base 5604. At least a portion of the assembled implant 100 may rest in the pocket 5608. For example, the second wall 176 may extend into the pocket 5608.

The caddy may be configured to hold multiple implants in an orderly arrangement. For example, the caddy may be configured to hold three rows of implants, each row including five implants. The arrangement of implants in the caddy may convey information about the size or style of each implant relative to those surrounding it. For example, a centrally located implant may represent an average configuration, with progressively smaller implants to the left and/or top, and progressively larger implants to the right and/or bottom. The caddy may be included in a sterilization tray or a packaging system.

Referring to FIGS. 46-54, steps in a method of use of the primary instrument 1000, secondary instrument 5000, and spinal implant 100 are illustrated.

Figure 47:
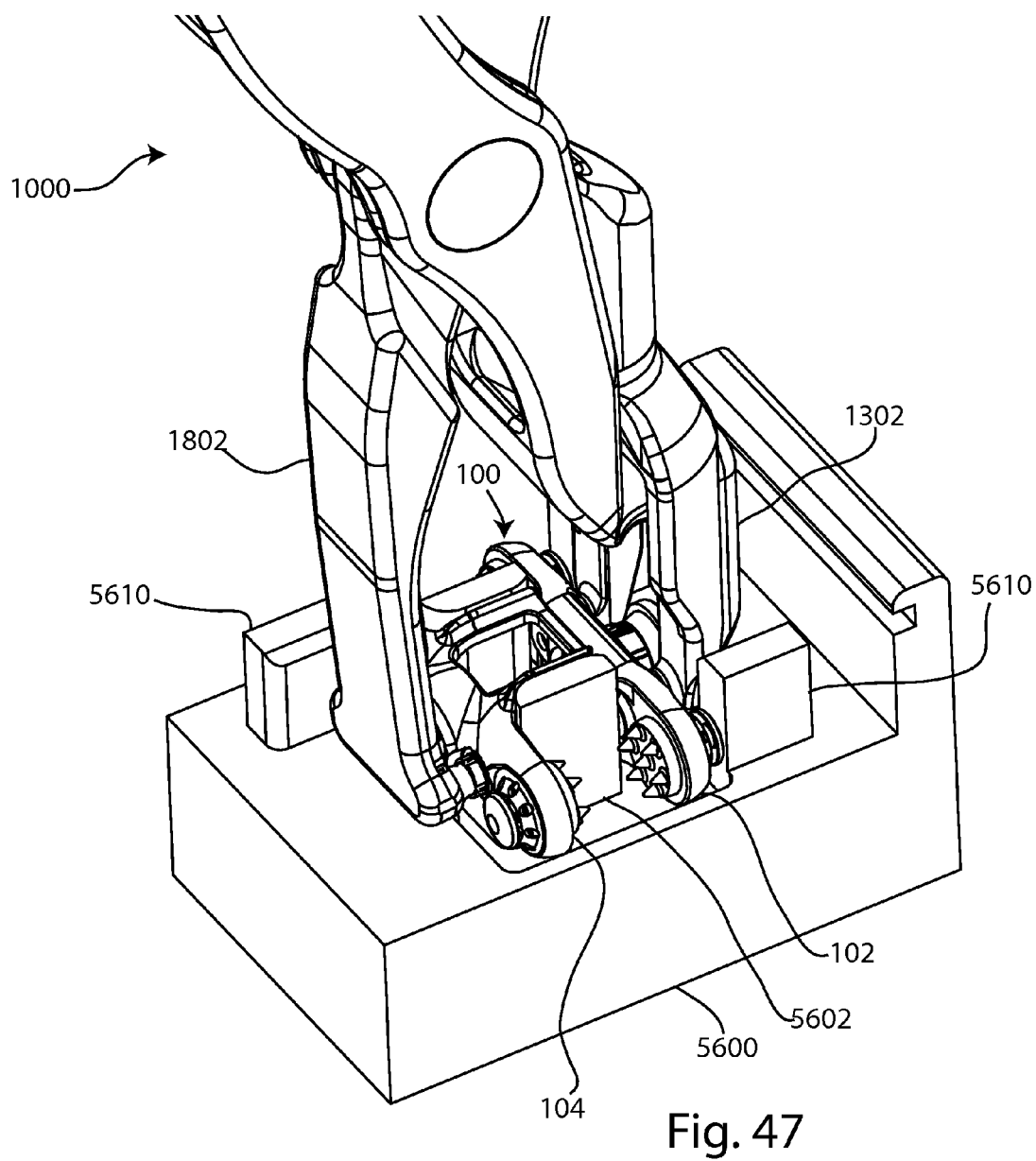
FIG. 47 is a perspective view of the primary instrument, spinal implant, and caddy of FIG. 46, with the primary instrument fully coupled to the implant.

In a first step, the primary instrument 1000 may be connected to the implant 100 while the implant 100 rests in the caddy 5600. The primary instrument 1000 may be prepared for this step by positioning the selector 1050 in the "CLAMP" position. Optionally, the ratchet arm 1900 may be lifted and/or the button 2000 pressed so that the handles 1804, 1104 may be widely separated. The ratchet arm 1900 may then be lowered to re-engage the tooth 1212. The primary instrument 1000 may be positioned with the rigid jaw 1802 proximate the extension plate 104 and the pivot jaw 1302 proximate the plate 102. The pivot jaw 1302 may be inserted between tabs 5610, if present. Tabs 5610 may guide pivot jaw 1302 into a favorable alignment with plate 102 to facilitate connection of spherical protrusions 1316, 1318 with instrument connection features 150. The rigid jaw 1802 may also be guided into alignment with plate 104 by additional tabs 5610, to facilitate connection of spherical protrusions 1816, 1818 with instrument connection elements 210. The number, size, and spacing of tabs 5602, 5610 may permit the implant 100 to be positioned in a preferred way relative to the caddy 5600, or the primary instrument 1000 to be positioned in a preferred way relative to the implant 100. Once the pivot jaw is aligned with plate 104, the spherical protrusions 1316, 1318 may be engaged with the connection features 150. FIG. 46 shows the primary instrument 1000, implant 100, and caddy 5600 after engagement of the spherical protrusions 1316, 1318 with the connection features 150. FIG. 47 shows the primary instrument 1000, implant 100, and caddy 5600 after engagement of the spherical protrusions 1816, 1818 with the connection elements 210.

Figure 48:
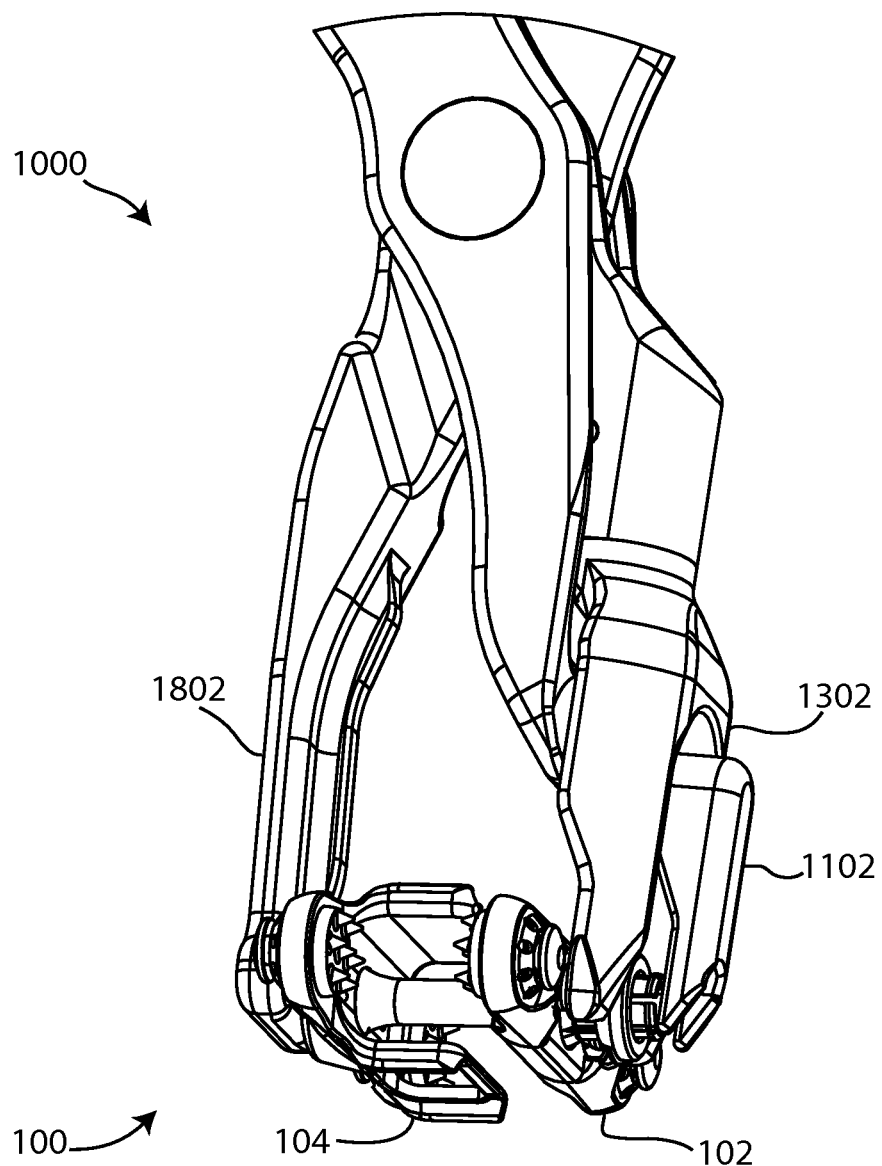
FIG. 48 is an enlarged detail perspective view of the primary instrument of FIG. 19 coupled with the spinal implant of FIG. 1, with the primary instrument in a configuration in which the lock and rigid legs are open, the selector is in a clamping position, and the ratchet arm is engaged with the pivot leg.
Figure 49:
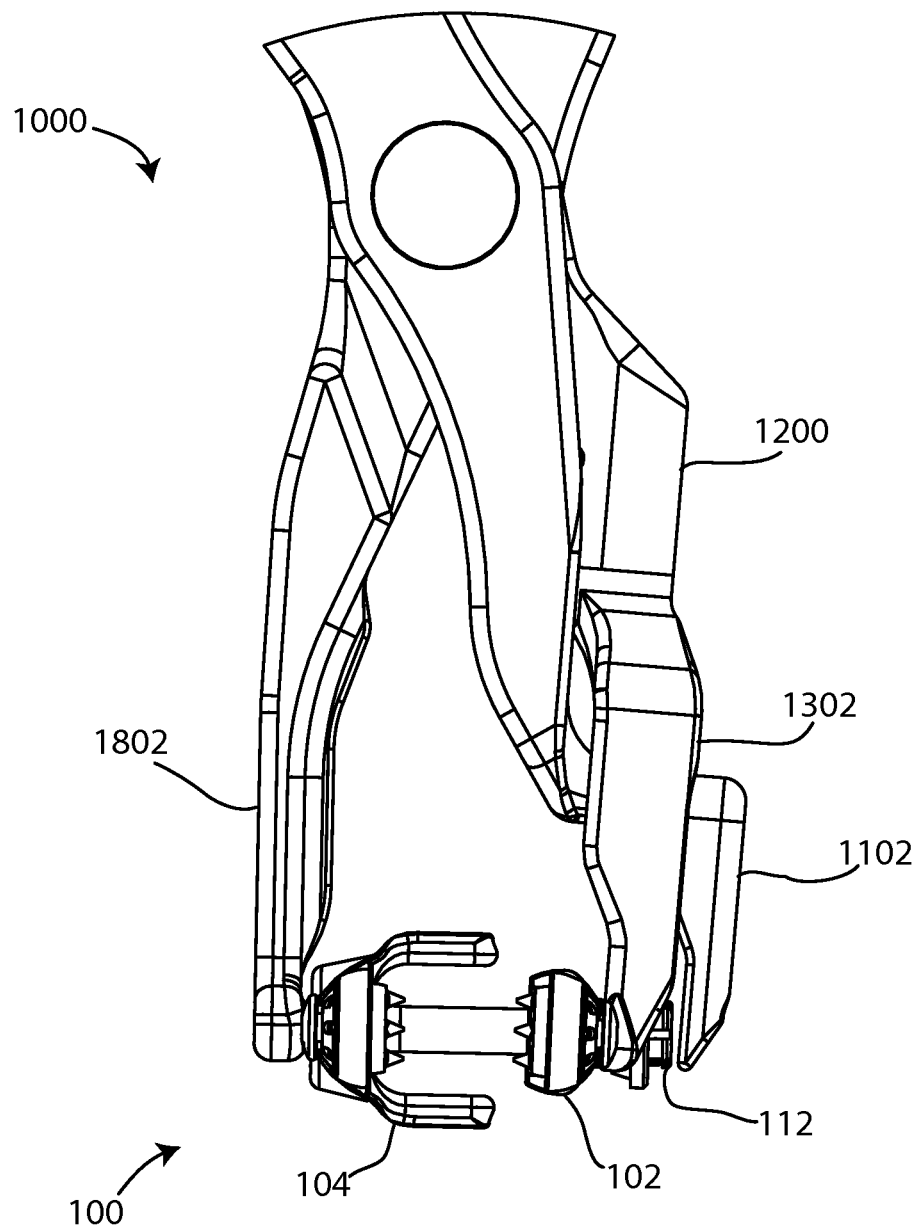
FIG. 49 is an enlarged detail front view of the primary instrument and the spinal implant of FIG. 48.

In a second step, the primary instrument 1000 may be lifted away from the caddy 5600 in order to pick up the implant 100, as shown in FIGS. 48-49. The implant 100 may slide out of the caddy 5600 with little or no resistance. The implant 100 may be held in an open or unlocked configuration, with the plate 102 spaced apart from the plate 104, as the implant is picked up and inserted in the implantation site. In other words, the implant 100 may be picked up without compressing the handles 1804, 1104 together. Referring to FIG. 49, it can be appreciated that, at this stage in the method, the lock jaw 1102 is held apart from the implant, particularly the components of the locking mechanism 108.

In a third step, the primary instrument 1000 may then be used to position the implant 100 in an implantation site, such as between spinous processes 2, 4 as illustrated in FIG. 2. This step may also be completed without compressing the handles 1804, 1104 of the primary instrument 1000.

With continued reference to FIG. 49, certain attributes of the primary instrument 1000 and implant 100 may be set forth. The connection between the spherical protrusions 1816, 1818 and the connection elements 210 permits the plate 104 to rotate relative to the rigid jaw 1802 about an axis through the spherical centers of the protrusions 1816, 1818 (or spherical cups 154). The connection between the spherical protrusions 1316, 1318 and the connection elements 150 permits the plate 102 to rotate relative to the pivot jaw 1302 about an axis through the spherical centers of the protrusions 1316, 1318 (or spherical cups 154). The pivot head 1302 also pivots relative to the pivot leg 1200, thus permitting plate 102 to pivot about a second axis, as may be seen in FIG. 51. The plate 102 is also polyaxially rotatable relative to the sphere portion 282 of the collet 112.

Figure 50:
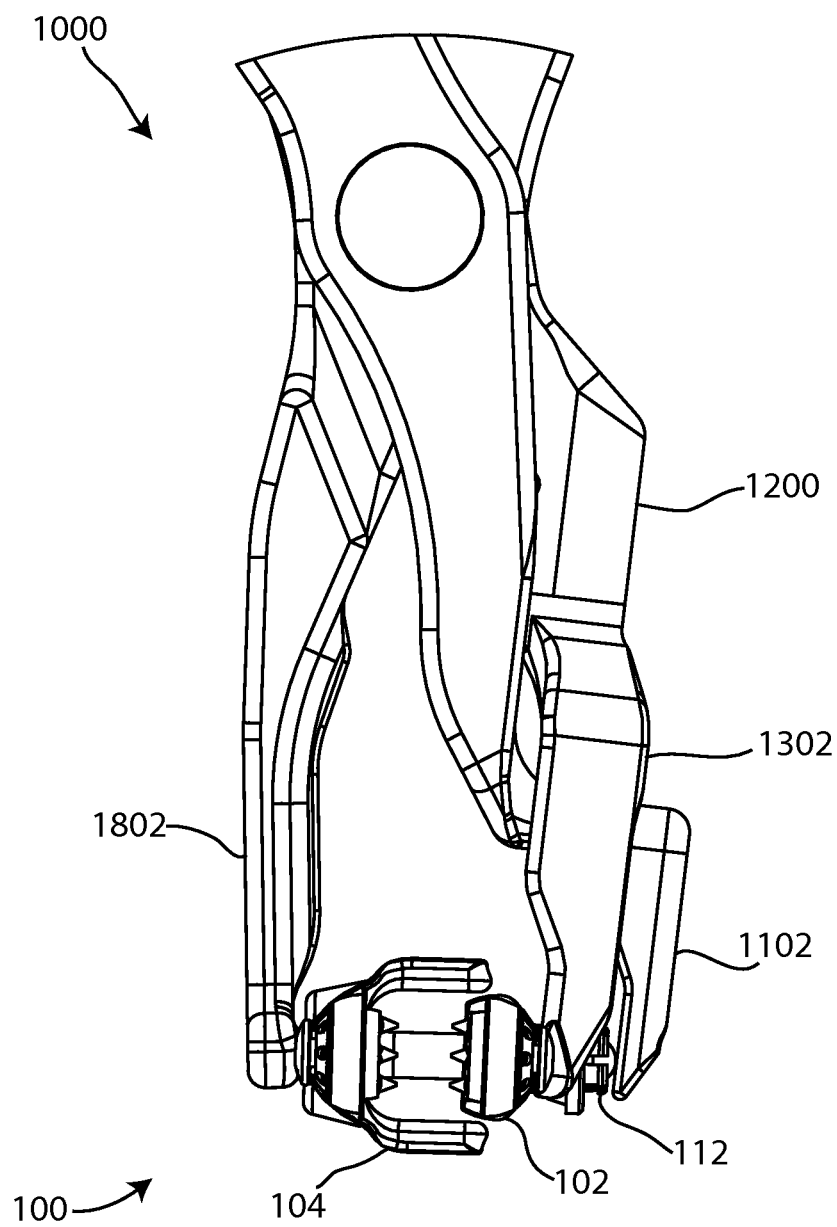
FIG. 50 is an enlarged detail front view of the primary instrument of FIG. 19 coupled with the spinal implant of FIG. 1, with the primary instrument in a configuration in which the lock and rigid legs are partially closed.
Figure 51:
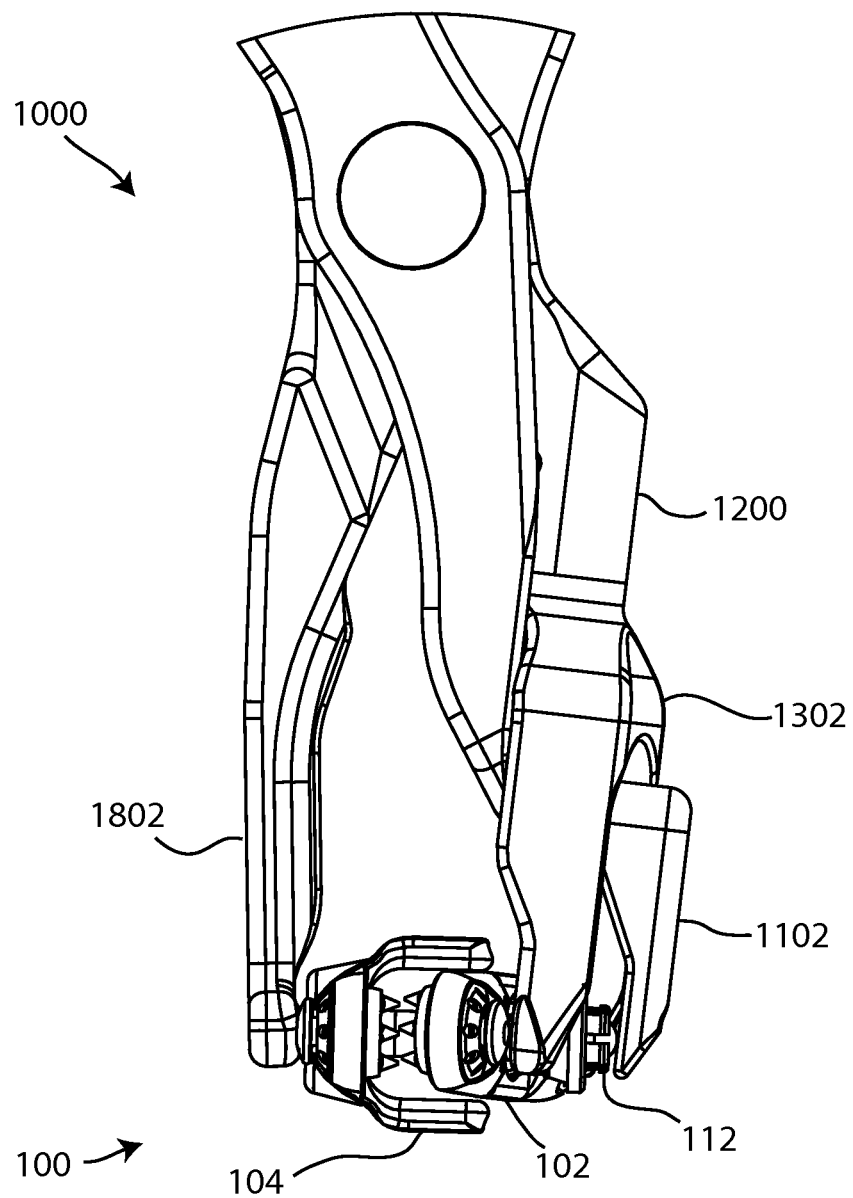
FIG. 51 is an enlarged detail front view of the primary instrument of FIG. 19 coupled with the spinal implant of FIG. 1, with the primary instrument in a configuration in which the pivot head is rotated out of alignment with the pivot leg.

In a fourth step, illustrated in FIG. 50, the handles 1804, 1104 may be compressed together to clamp the plates 102, 104 together. As the clamping step occurs, the primary instrument 1000 permits the implant 100 to automatically align itself to the anatomy present at the implantation site. FIG. 51 illustrates an implant 100 which has pivoted during clamping. As the clamping force increases, a first force sufficient to deform the spacers 250 may be reached, followed by a second force sufficient to lock the pads relative to the plates 102, 104. However, during this step, no compressive force is applied by the lock jaw 1102 to the locking mechanism 108. As the clamping step occurs, the ratchet arm 1900 permits the handles 1804, 1104 to be compressed together, but resists opening. The user may release the handles 1804, 1104, yet the primary instrument 1000 will maintain compression across the plates 102, 104. The user may also apply a series of compressions to the implant 100 if desired.

Figure 52:
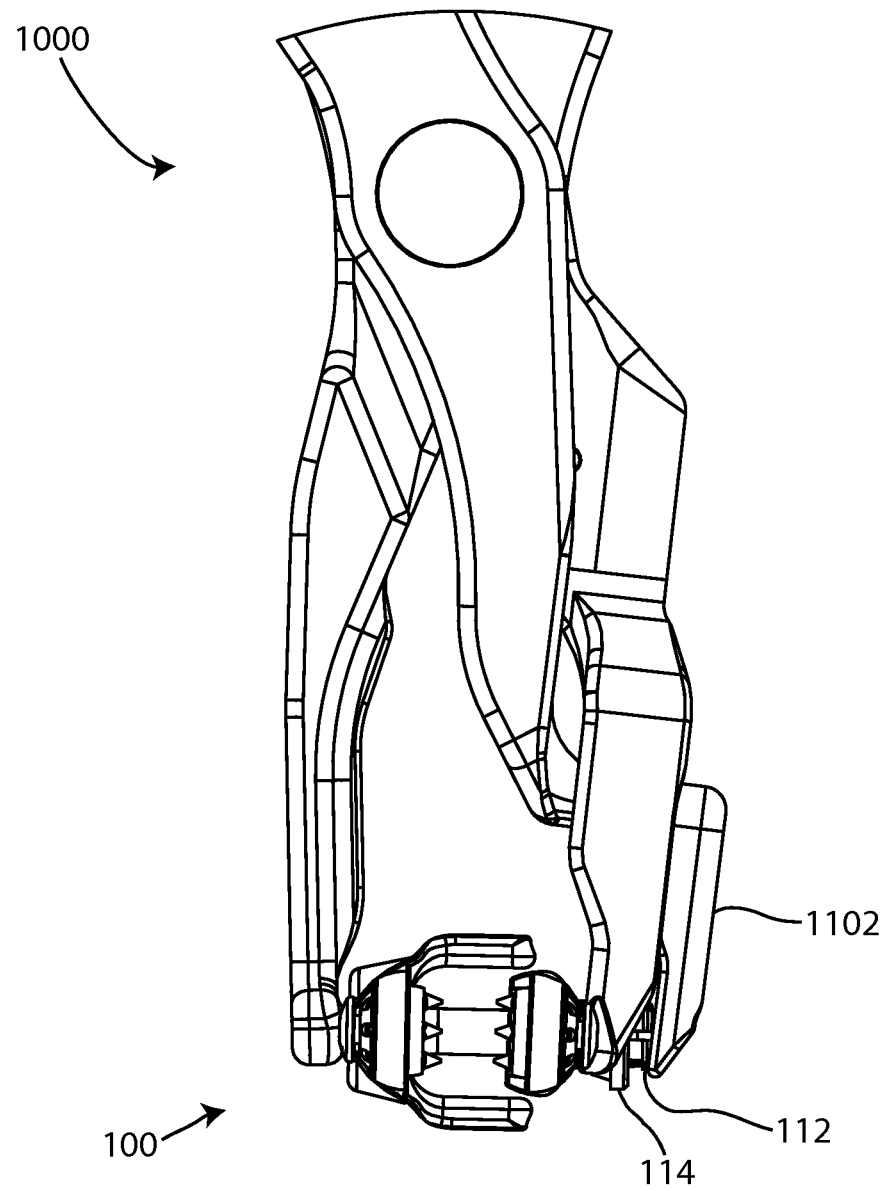
FIG. 52 is an enlarged detail front view of the primary instrument of FIG. 19 coupled with the spinal implant of FIG. 1, with the primary instrument in a configuration in which the pivot head is realigned with the pivot leg, the selector is in a locking position, and the lock and rigid legs are closed.

In a fifth step, illustrated in FIG. 52, after the implant has been appropriately compressed or clamped, the selector 1050 may be moved to the "LOCK" position. Further compression of the handles 1804, 1104 moves the lock jaw 1102 into contact with the collet 112. Still further compression of the handles 1804, 1104 causes the lock jaw 1102 to push the collet 112 into the frustoconical surface 138 to lock the implant. FIG. 13 illustrates the forces involved in this step. At a predetermined compressive load, the force indicator 1060 may react to indicate that an adequate locking force has been applied to the implant 100. During this step, the ratchet arm 1900 may connect the rigid leg 1100 to the pivot leg 1200 so that there is no relative movement between the rigid jaw 1102 and the pivot jaw 1302, and thus no relative movement or additional compression between the plates 102, 104.

After the locking step is complete, the primary instrument 1000 may be disconnected from the implant 100 by releasing the handles 1804, 1104, lifting the ratchet arm 1900 to release the connection between the rigid leg 1100 and the pivot leg 1200, and disengaging the spherical protrusions 1316, 1318 and 1816, 1818 from the connection features 150, 210.

Figure 53:
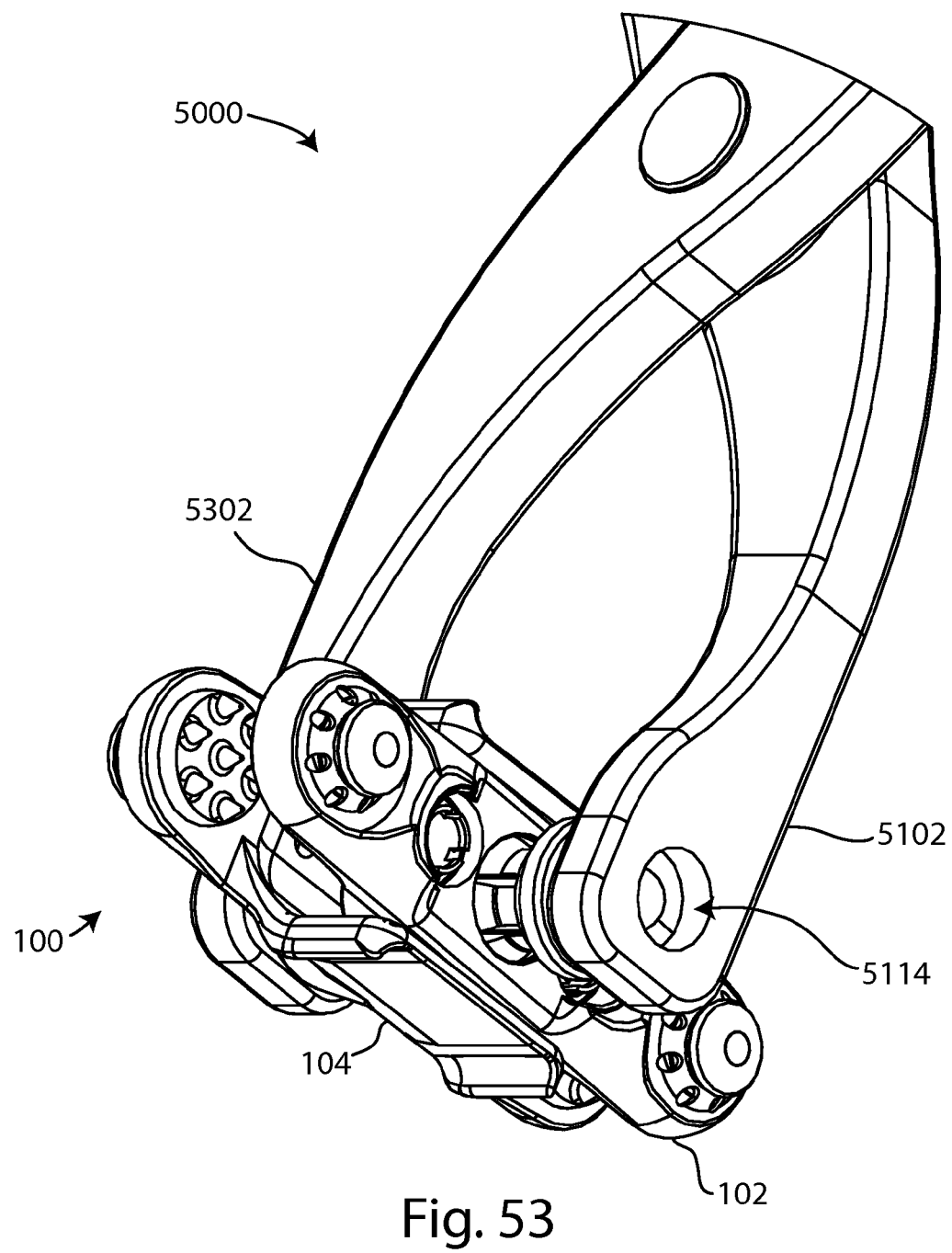
FIG. 53 is an enlarged detail perspective view of the secondary instrument of FIG. 44 coupled with the spinal implant of FIG. 1, with the secondary instrument in a configuration in which the force indicator and rigid legs are open.
Figure 54A:
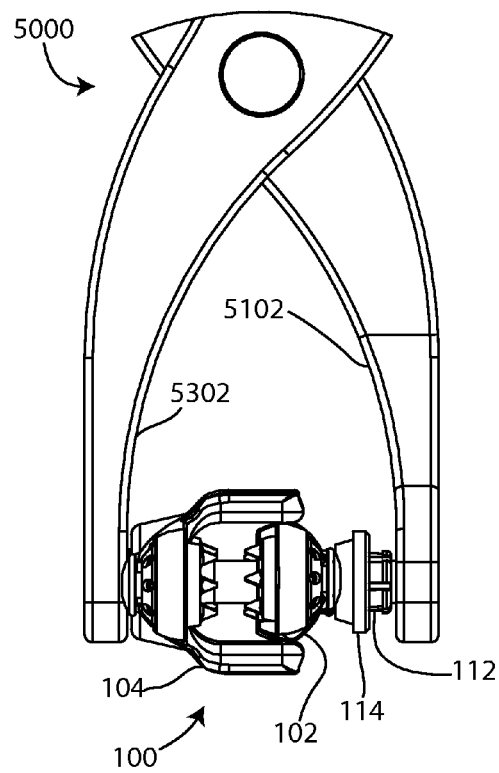
FIG. 54A is an enlarged detail front view of the secondary instrument and the spinal implant of FIG. 53.
Figure 54B:
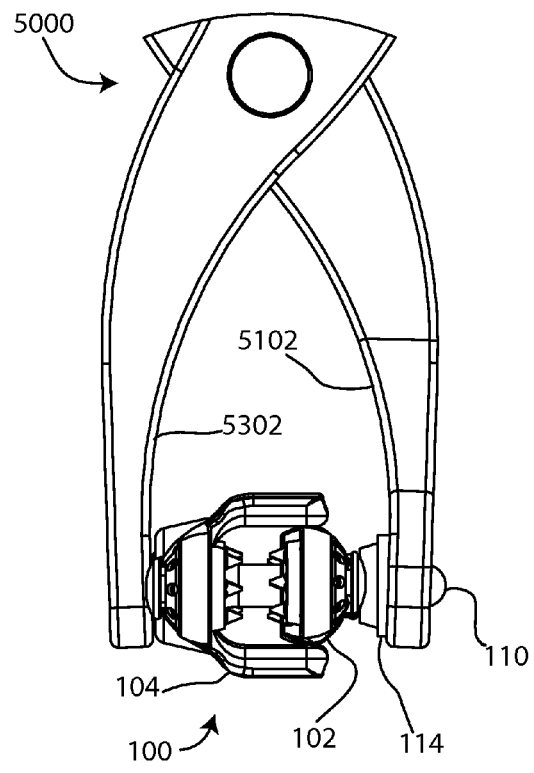
FIG. 54B is an enlarged detail front view of the secondary instrument of FIG. 44 coupled with the spinal implant of FIG. 1, with the secondary instrument in a configuration in which the force indicator and rigid legs are closed.

Referring to FIGS. 53-54B, the secondary instrument 5000 may be coupled to the implant by inserting the first end of the post 110 into the hole 5114 and engaging a portion of post head 264 in dimple 5314.

A compressive force may be applied to the handles 5104, 5304 of the secondary instrument to close the jaws 5102, 5302. It can be appreciated that the secondary instrument 5000 applies a compressive force through the locking mechanism 108 in this arrangement. The rigid jaw 5302 supports the post 110 and the force indicator jaw 5102 presses against the ring 114. No compressive force is applied to the plates 102, 104. FIG. 14 illustrates the forces involved in this step. As the handles 5104, 5304 are compressed together, the ring 114 is forced along the conical taper of the collet 112 until the collet 112 becomes wedged between the ring 114 and the post 110. At a predetermined compressive load, the force indicator 5060 may react to indicate that an adequate locking force has been applied to the implant 100.

The secondary instrument 5000 may be disconnected from the implant 100 by opening the handles 5104, 5304 and sliding the jaw 5102 off the post 110.

It is appreciated that in alternate embodiments of the invention, the features and capabilities of the first 350 and second 380 instruments may be combined on a single instrument, or found on separate instruments. For example, a first instrument may provide force for locking of polyaxial pads or feet of an implant, a second instrument may provide force for a provisional lock of a locking mechanism, while a third instrument may provide force for a final lockout of a locking mechanism. It is also appreciated that first 350 and second 380 instruments may be used for providing insertion, compression and/or locking of other plate systems, implants or locking mechanisms.

The individual components above may be provided separately or in combinations or kits. The implant may be provided in a variety of sizes to allow a practitioner to select a size appropriate for the patient's anatomy and/or desired outcome. Any component may vary in overall size or selected individual dimension. For example, the post, ring and/or collet may each be available in a variety of lengths and/or radii. The plates may be available in a variety of lengths and widths, and with varying numbers of polyaxial connection features. The instruments may be individually sized to fit a particular plate size, or may be available in a 'one size fits all' configuration in which one instrument can connect with any size plate due to the strategic placement of instrument connection features on the plates. An embodiment of a kit may include an implant and instrumentation for implantation, compression, and locking. Another embodiment of a kit may include only implants in a variety of sizes, and another embodiment may include only instrumentation.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system, comprising:
    an implant, wherein the implant comprises:
        a first portion,
        a second portion opposite the first portion, and
        a locking mechanism coupling the first portion to the second portion; and
    a primary instrument;
    wherein the system has an insertion configuration, a clamped configuration, and a first locked configuration;
    wherein, in the insertion configuration, the primary instrument holds the first portion apart from the second portion;
    wherein the primary instrument urges the first portion toward the second portion to change the system from the insertion configuration to the clamped configuration, wherein the primary instrument permits the first portion to polyaxially rotate relative to the second portion as the first portion is urged toward the second portion;
    wherein, in the clamped configuration, the primary instrument holds the first portion fixed relative to the second portion;
    wherein the primary instrument maintains the first portion fixed relative to the second portion as a first component of the locking mechanism is urged from an unlocked position to a first locked position to change the system from the clamped configuration to the first locked configuration;

wherein, in the first locked configuration, the first component maintains the first portion fixed relative to the second portion;

wherein the primary instrument comprises a selector, wherein, in the insertion and clamped configurations, the selector is in a first position, wherein, in the first locked configuration, the selector is in a second position, wherein, when the selector is in the first position, the system is prevented from changing to the first locked configuration, wherein, when the selector is in the second position, the system is permitted to change to the first locked configuration.

2. The system of claim 1, wherein the primary instrument comprises first and second opposing jaws, wherein the first jaw is pivotable relative to the second jaw about first and second axes, wherein the second axis is perpendicular to the first axis, wherein the first jaw holds the first portion, wherein the first portion is pivotable relative to the first jaw about a third axis, wherein the third axis is perpendicular to the second axis, wherein the second jaw holds the second portion, wherein the second portion is pivotable relative to the second jaw about a fourth axis, wherein the fourth axis is parallel to the first axis.

3. The system of claim 1, wherein the primary instrument comprises a force indicator, wherein the force indicator indicates when a predetermined locking force has been applied by the primary instrument to urge the first component from the unlocked position to the first locked position.

4. The system of claim 1, wherein the primary instrument avoids contact with the locking mechanism in the insertion configuration and the clamped configuration.

5. The system of claim 4, wherein the primary instrument contacts at least the first component in the first locked configuration.

6. The system of claim 1, comprising:
a secondary instrument;
wherein the system has a second locked configuration;
wherein the secondary instrument urges at least a second component of the locking mechanism from an unlocked position to a second locked position to change the system from the first locked configuration to the second locked configuration, wherein the secondary instrument avoids contact with the first and second portions as the second component is urged from the unlocked position to the second locked position;
wherein, in the second locked configuration, the first and second components of the locking mechanism maintain the first portion fixed relative to the second portion.

7. The system of claim 6, wherein the secondary instrument comprises a force indicator, wherein the force indicator indicates when a predetermined locking force has been applied by the secondary instrument to urge the second component from the unlocked position to the locked position.

8. A system, comprising:
an implant, wherein the implant comprises first and second plates coupled together by a locking mechanism, wherein the second plate faces the first plate; and
a primary instrument releasably securable to the implant, wherein the primary instrument comprises rigid and pivot jaws hinged together at a main pivot element so that the pivot jaw is rotatable relative to the rigid jaw about a center longitudinal axis of the pivot element, wherein the rigid jaw faces the pivot jaw, wherein the pivot jaw is releasably connected to the rigid jaw, wherein the connection permits one way motion of the pivot jaw toward the rigid jaw, wherein the pivot jaw is rotatable relative to the rigid jaw about a second axis, wherein the second axis forms a non-zero angle with the center longitudinal axis;
wherein the primary instrument remains continuously secured to the implant while the implant is picked up, inserted in an implantation site, compressed, and locked;
wherein the primary instrument comprises a lock jaw hinged at the main pivot element so that the rigid, pivot, and lock jaws are independently rotatable about the center longitudinal axis, wherein the rigid jaw faces the lock jaw, wherein the lock jaw is releasably fixed to the pivot jaw, wherein the pivot jaw is rotatable relative to the lock jaw about the second axis, wherein the lock jaw applies no compressive force to the implant when the lock jaw is releasably fixed to the pivot jaw while the primary instrument compresses the first and second plates together.

9. The system of claim 8, wherein the first plate is releasably securable to the pivot jaw and the second plate is releasably securable to the rigid jaw.

10. The system of claim 9, wherein the first plate and second plate each comprise cup shaped pockets, wherein the pivot jaw and the rigid jaw each comprise spherical tips, wherein the cup shaped pockets releasably receive the spherical tips, wherein the cup shaped pockets are pivotable on the spherical tips.

11. The system of claim 8, comprising:
a caddy, wherein the caddy supports the implant with the first plate separated from the second plate;
wherein the primary instrument is releasably securable to the implant while the implant is supported by the caddy;
wherein the primary instrument picks the implant up out of the caddy after the primary instrument is releasably secured to the implant.

12. The system of claim 8, wherein the primary instrument holds the first plate separated from the second plate while the implant is inserted into an implantation site.

13. The system of claim 8, wherein the lockjaw applies a compressive force to the implant when the lock jaw is released from the pivot jaw while the primary instrument locks the first and second plates together.

14. A system comprising:
an implant, wherein the implant comprises a first portion, a second portion opposite the first portion, and a locking mechanism coupling the first portion to the second portion; and
a primary instrument, wherein the primary instrument comprises rigid and pivot jaws hinged together at a main pivot element, wherein each jaw is independently rotatable about a center longitudinal axis of the pivot element, wherein the rigid jaw faces the pivot jaw, wherein the pivot jaw is rotatable about a second axis, wherein the second axis is nonparallel to the center longitudinal axis of the pivot element, wherein the primary instrument further comprises a lock jaw hinged at the main pivot element and releasably fixed to the pivot jaw, the lock jaw configured to apply a compressive force to the implant when the lock jaw is released from the pivot jaw while the primary instrument locks the first and second portion in a fixed relationship;
wherein the primary instrument remains continuously connected to the implant as the implant is positioned in an implantation site, the second portion is compressed toward the first portion, and the locking mechanism is actuated to lock the implant in a fixed relationship.

15. The system of claim 14, wherein the primary instrument comprises a first setting, in which the pivot jaw is free to rotate relative to the rigid jaw, and a second setting, in which the rigid jaw is fixed relative to the pivot jaw;

wherein the primary instrument connects to the implant, positions the implant in the implantation site, and compresses the second portion toward the first portion while the primary instrument is in the first setting; wherein the primary instrument actuates the locking mechanism while the primary instrument is in the second setting.

16. The system of claim 14, wherein the primary instrument comprises a releasable connection between the pivot jaw and the rigid jaw, wherein the connection permits rotation of the pivot jaw toward the rigid jaw and prevents rotation of the pivot jaw away from the rigid jaw.

17. The system of claim 14, wherein the first portion is releasably securable to the pivot jaw and the second portion is releasably securable to the rigid jaw;

wherein the first portion and second portion each comprise cup shaped pockets, wherein the pivot jaw and the rigid jaw each comprise spherical tips, wherein the cup shaped pockets releasably receive the spherical tips, wherein the cup shaped pockets are pivotable on the spherical tips.

18. The system of claim 14, comprising:

a caddy, wherein the caddy supports the implant with the first plate separated from the second plate;

wherein the primary instrument is releasably securable to the implant while the implant is supported by the caddy;

wherein the primary instrument picks the implant up out of the caddy after the primary instrument is releasably secured to the implant.

\* \* \* \* \*

UNITED STATES PATENT AND TRADEMARK OFFICE
CERTIFICATE OF CORRECTION

PATENT NO. : 8,721,686 B2  
APPLICATION NO. : 13/188325  
DATED : May 13, 2014  
INVENTOR(S) : Charles R. Gordon et al.

Page 1 of 1

It is certified that error appears in the above-identified patent and that said Letters Patent is hereby corrected as shown below:

In the Specification:
    At column 1, line number 30, delete "their & entirety" and replace with --their entirety--.
    At column 7, line number 20, delete "instrument a maintains" and replace with --instrument maintains--.
    At column 10, line number 2, delete "may a be" and replace with --may be--.
    At column 11, line number 8, delete "surface may" and replace with --surface 144 may--.
    At column 11, line number 13, delete "112 a may" and replace with --112 may--.
    At column 14, line number 26, delete "having a a frustoconical" and replace with --having a frustoconical--.
    At column 14, line number 66, delete "range 9 from" and replace with --range from--.
    At column 15, line number 33, delete "extension a plate" and replace with --extension plate--.
    At column 16, line number 45, delete "can a occur" and replace with --can occur--.
    At column 17, line number 10, delete "other a metals" and replace with --other metals--.
    At column 19, line number 24, delete "be a bilaterally" and replace with --be bilaterally--.

Signed and Sealed this  
Fifth Day of August, 2014

Michelle K. Lee  
*Deputy Director of the United States Patent and Trademark Office*